US012729367B2

(12) United States Patent
Singec et al.

(10) Patent No.: US 12,729,367 B2
(45) Date of Patent: Sep. 8, 2026

(54) RADIAL GLIA AND ASTROCYTE DIFFERENTIATION FROM HUMAN PLURIPOTENT STEM CELLS

(71) Applicant: The United States of America, as represented by the Secretary, Dept. of Health and Human Services, Bethesda, MD (US)

(72) Inventors: Ilyas Singec, Gaithersburg, MD (US); Vukasin Jovanovic, Rockville, MD (US); Anton Simeonov, Bethesda, MD (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 699 days.

(21) Appl. No.: 17/796,044

(22) PCT Filed: Feb. 19, 2021

(86) PCT No.: PCT/US2021/018659
§ 371 (c)(1),
(2) Date: Jul. 28, 2022

(87) PCT Pub. No.: WO2021/168171
PCT Pub. Date: Aug. 26, 2021

(65) Prior Publication Data

US 2023/0056533 A1 Feb. 23, 2023

Related U.S. Application Data

(60) Provisional application No. 62/979,429, filed on Feb. 21, 2020.

(51) Int. Cl.
*C12N 5/079* (2010.01)

(52) U.S. Cl.
CPC ........ *C12N 5/0622* (2013.01); *C12N 2500/36* (2013.01); *C12N 2500/38* (2013.01); *C12N 2501/13* (2013.01); *C12N 2501/135* (2013.01); *C12N 2501/155* (2013.01); *C12N 2501/2306* (2013.01); *C12N 2501/235* (2013.01); *C12N 2501/237* (2013.01); *C12N 2501/42* (2013.01); *C12N 2501/999* (2013.01); *C12N 2506/02* (2013.01); *C12N 2506/45* (2013.01); *C12N 2533/52* (2013.01); *C12N 2533/54* (2013.01)

(58) Field of Classification Search
None
See application file for complete search history.

(56) References Cited

U.S. PATENT DOCUMENTS 10,494,602 B1 12/2019 Sloan et al.

FOREIGN PATENT DOCUMENTS

| | | | | |
|---|---|---|---|---|
| EP | 3418378 A1 | 12/2018 | | |
| WO | WO 03008566 A1 | 1/2003 | | |
| WO | WO-2012135621 A2 * | 10/2012 | ............. | A61K 35/12 |
| WO | WO 2016103269 A1 | 6/2016 | | |
| WO | WO-2020077266 A1 * | 4/2020 | ........... | C12N 5/0696 |

OTHER PUBLICATIONS

Varga, B. and Nagy, A. Isolation, Propagation, and Differentiation of Radial Glia-Like Neural Progenitor Cells in Adherent Cultures, 2017, Cold Spring Harb Protoc; doi: 10.1101/pdb.prot094177 (Year: 2017).*
Corning Cell culture Vessel Guide https://www.corning.com/catalog/cls/documents/application-notes/CLS-AN-209.pdf (Year: 2023).*
Chen, et al. A Versatile Polypharmacology Platform Promotes Cytoprotection and Viability of Human Pluripotent and Differentiated Cells, Oct. 22, 2019, bioRxiv (Year: 2019).*
Gorris et al, Pluripotent Stem Cell-Derived Radial Glia-Like Cells as Stable Intermediate for Efficient Generation of Human Oligodendrocytes, Glia, 2015, 63:2152-2167 (Year: 2015).*
Blackwood, Jagged1 is essential for radial glial maintenance in the cortical proliferative zone, Neuroscience, 2019; 413:230-238 (Year: 2019).*
Bonaguldl et al, LIF and BMP signaling generate separate and discrete types of GFAP-expressing cells, Development, 2005, 132, 5503-5514 (Year: 2005).*
Walsh et al, Defined Culture Conditions Accelerate Small-molecule-assisted Neural Induction for the Production of Neural Progenitors from Human-induced Pluripotent Stem Cells, Cell Transplantation, 2017, vol. 26(12) 1890-1902 (Year: 2017).*
Kuwahara et a., Preconditioning the Initial State of Feeder-free Human Pluripotent Stem Cells Promotes Self-formation of Three-dimensional Retinal Tissue, Scientific Reports, 2019, 9:18936 (Year: 2019).*
Stupnikov et al, Jagged and Delta-like Ligands control distinct events during airway progenitor cell differentiation, eLife, 2019 (Year: 2019).*
International Search Report issued in International Application No. PCT/US2021/018659, mailed on Jun. 29, 2021 (3 pages).
Written Opinion issued in International Application No. PCT/US2021/018659, mailed on Jun. 29, 2021 (3 pages).
International Preliminary Report on Patentability issued in International Application No. PCT/US2021/018659, mailed on Aug. 23, 2022 (6 pages).
Bottenstein, J.E., “Growth and differentiation of neural cells in defined media”, Cell Culture in the Neurosciences, p. 3-43 (1985).
Brewer, et al., “Optimized survival of hippocampal neurons in B27-supplemented neurobasal™, a new serum-free medium combination,” Journal of Neuroscience Research 35:567-76 (1993).

(Continued)

*Primary Examiner* — Allison M Fox
*Assistant Examiner* — Marisol Ann O'Neill
(74) *Attorney, Agent, or Firm* — McDonnell, Boehnen Hulbert & Berghoff LLP

(57) ABSTRACT

Methods for generating multipotent radial glia-like cells and astrocyte-like cells from human pluripotent stem cells are provided along with the related compositions.

18 Claims, 15 Drawing Sheets

(56) References Cited

OTHER PUBLICATIONS

Chen, et al., "Chroman-3-amides as potent Rho kinase inhibitors", Bioorganic and medicinal Chemistry Letters, 18:6406-6409 (2008).
LoGrasso, et al, "Rho Kinase (ROCK) Inhibitors and Their Application to Inflammatory Disorders", Current Topics in medicinal Chemistry 9:704-723 (2009).
Linton, et al., "First-in-Class Pan Caspase Inhibitor Developed for the Treatment of Liver Disease", J. Med. Chem 48:6779-6782 (2005).
Sidrauski, et al., "Pharmacological brake-release of mRNA translation enhances cognitive memor", eLIFE2:e00498 (2013).
Chambers, et al., "Highly efficient neural conversion of human ES and iPS cells by dual inhibition of SMAD signaling," Nat. Biotechnol., 27:275-280 (2009).
Tchieu, et al., "FNIA is a gliogenic switch enabling rapid derivation of funcational human astrocytes from pluripotent stem cells", Nat. Biotechnol. 37:267-275 (2019).
Matrigel, https://en.wikipedia.org/wiki/Matrigel; accessed on Jul. 10, 2025.
Geltrex Flex Basement Membrane Matrices, https://www.thermofisher.com/us/en/home/life-science/cell-culture/organoids-spheroids-3d-cell-culture/extracellular-matrices-ecm/geltrex-matrix-products.html; accessed on Jul. 10, 2025.
Essential 8 Medium 500 mL, https://www.thermofisher.com/order/catalog/product/A1517001; accessed on Jul. 10, 2025.
Essential 8 Flex Medium Kit, https://www.thermofisher.com/order/catalog/product/A2858501ef_id=CjwKCAjwyb3DBhBIEiwAqZLe5O9SKk35lqstrCkSUg4TUrsdEb8_BS3QneQFLmP47n8yVnVNhR87-xoCflsQAvD_BwE:G:s&s_kwcid=AL!3652!3!721123635119!!!g!!!21905512708!173946064721&cid=bid_clb_acn_r01_co_cp0000_pjt0000_bid00000_0se_gaw_dy_pur_con&gad_source=1&gad_campaignid=21905512708&gbraid=0AAAAADxi_GSHI5sL7xQCB4OTRL8TR2s9l&gclid=CjwKCAjwyb3DBhBIEiwAqZLe5.
StemFlex Medium for Robus Feeder-Free PSC Culture, https://www.thermofisher.com/us/en/home/life-science/stem-cell-research/induced-pluripotent-stem-cells/medium-robust-feeder-free-psc-culture.html?ef_id=CjwKCAjwyb3DBhBIEiwAqZLe5G7ulSoiBolDZH5f4LF7989_MZE4ir-MJMda9u7HDw9078cRyfEvNhoCN3gQAvD_BwE:G:s&s_kwcid=AL!3652!3!721148850170!e!!g!!stemflex%20medium!21905693674.
MTeSR 1, https://www.stemcell.com/products/mtesr1.html; accessed on Jul. 10, 2025.
StemFit, https://www.ajitrade.com/stemfit/products/?psafe_param=1&gad_source=1&gad_campaignid=14882976866&gbraid=0AAAAABW-KaJK158xVcCoyNTdBMfpbbo2M&gclid=CjwKCAjwyb3DBhBIEiwAqZLe5M4pO2f1Drm0ane7JnCBHetRWewcOaUD3s-w4oAXK_9EvXUg1TxFCBoCmXsQAvD_BwE; accessed on Jul. 10, 2025.
Dulbecco's Medified Eagle Medium F12 (DMEM-F12), https://www.thermofisher.com/us/en/home/life-science/cell-culture/mammalian-cell-culture/cell-culture-media/dmem-f12.html?ef_id=CjwKCAjwyb3DBhBIEiwAqZLe5LUULilSJERZAA784W2UuF4s4x_FWkuki2tDHOTomxQvwDBAKxbqOhoCvHIQAvD_BwE:G:s&s_kwcid=AL!3652!3!733018704141!e!!g!!dmem%2Ff12!1759362858!66460962621&cid=bid_clb_cce_r01_co_cp0000_pjt0000_bid00000_0se_gaw_nt_pur_con&gad_source=1&gad_camp.
Essential 6 Medium—Differentiate PSCS into Various Lineages (E6), https://www.thermofisher.com/us/en/home/life-science/stem-cell-research/induced-pluripotent-stem-cells/essential-6-8-medium/essential-6-medium.html?ef_id=CjwKCAjwyb3DBhBIEiwAqZLe5Hmb_GJICRAE4PY9cnnCDgNHkZtaNkBvq2BC3ehgMo_6ozdtLSM18hoCdr4QAvD_BWE:G:s&s_kwcid=AL!3652!3!721148850161!e!!g!!e6%20medium!21905693674!174033104367&cid=bid_clb_scl_r01_co_cp0000_pjt0000_bid00000_0se_gaw_bt_pur_con&gad_source=1&gad_camp.
Neurobasal Medium: The Most Cited Medium for Neuronal Cell Culture,https://www.thermofisher.com/us/en/home/brands/gibco/neurobasal-products.html?ef_id=CjwKCAjwyb3DBhBIEiwAqZLe5KN3zGXd42UO1WXqXtH7RZpdK_IDVe-_gqRP18mK2GhEai03RyxhiBoCt4QQAvD_BWE:G:s&s_kwcid=AL!3652!3!721025882313!e!!g!! neurobasal%20medium!21905512711!.
Kopan, et al., "The Canonical Notch Signaling Pathway: Unfolding the Activation Mechanisn", Cell, 137:216-233 (2009).
Engers, et al., "Synthesis and and structure-activity relationships of a novel and selective bone morphogenetic protein receptor (BMP) inhibitor derived from the pyrazolo [1.5-a]pyrimidine scaffold of Dorsomorphin: The discovery of ML347 as an ALK2 versus ALK3 selective MLPCN probe", Bioorg. Med. Chem. Lett., 23:3248-3252 (2013).
Zhang, et al., "BMP signaling and stem cell regulation", Developmental Biology, 284:1-11 (2005).
Androutsellis-Theotokis, et al., "Notch signalling regulates stem cell Nos. in vitro and in vivo", Nature, 442:823-826 (2006).
Ali, et al., "Bone morphogenetic proteins and their antagonists: current and emerging clinical uses", British Journal of Pharmacology, 171:3620-3632 (2014).
Carvalho, et al., "ALK2 inhibitors display beneficial effects in preclinical models of ACVR1 mutant diffuse intrinisic pontine glioma", Communications Biology, 156:1-10 (2019).
Hong, et al., "Applications of small molecule BMP inhibitors in physiology and disease", Cytokine Growth Factor Rev., 20:1-25 (2009).

* cited by examiner

FIG. 1A

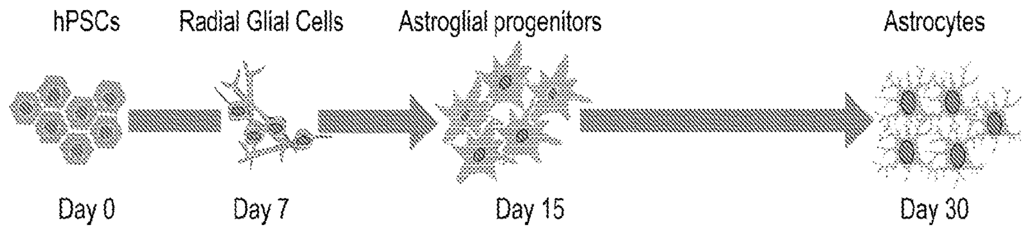

FIG. 1B

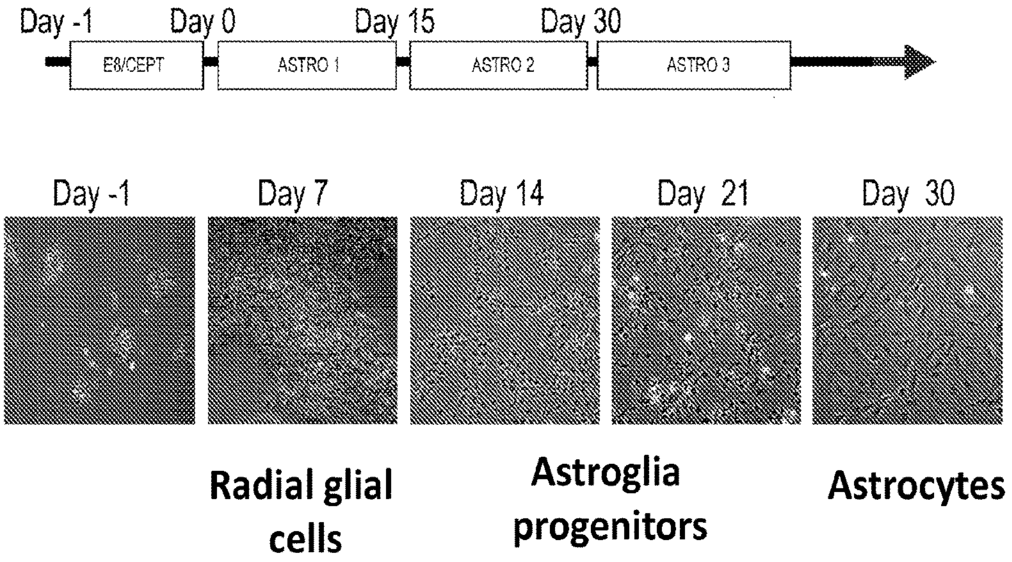

Day -1: plate human pluripotent stem cells (hPSCs) at 10.000 cells/cm$^2$ on vitronectin coated vessels in E8 medium with CEPT cocktail for cytoprotection after cell dissociation and consistent cell survival

Day 0-15: Astro 1 medium; daily medium change, passage when plates are fully confluent in 1:3 ratio (4-5 passages total)

Day 15-30: Astro 2 medium; daily medium change, cell proliferation decreases; passage once around Day 23 in 1:2 ratio

Beyond Day 30: Astro 3 medium; maintenance and maturation medium; change medium every 3 days

FIG. 2A

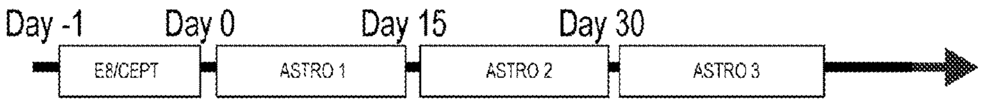

Astro 1 Medium for Day 0-15:

- LDN-193189 100 nM
- Jagged1 10 ng/mL
- DLL1 10 ng/mL
- PDGF-AA 10 ng/mL
- ONCOSTATIN M 10 ng/mL
- CNTF 10 ng/mL
- LIF 10 ng/mL Base medium: DMEM/F12 + N2 supplement + B27 supplement (without vitamin A)

FIG. 2B

Astro 2 Medium for Day 15-30 (components):

- Fetal Bovine Serum 2% or lipid concentrate 2%
- Jagged1 10 ng/mL
- DLL1 10 ng/mL
- ONCOSTATIN M 10 ng/mL
- CNTF 10 ng/mL
- LIF 10 ng/mL Base medium: DMEM/F12 + N2 supplement + B27 supplement (complete)

FIG. 2C

Astro 3 Medium after Day 30:

- Fetal Bovine Serum 2% or lipid concentrate 2%
- CNTF 10 ng/mL
- LIF 10 ng/mL

Base medium: DMEM/F12 + N2 supplement + B27 supplement (complete)

FIG. 2D

Astrocytes protect motor neurons from glutamate toxicity

Human Astrocytes (Day 30)

FIG. 13A

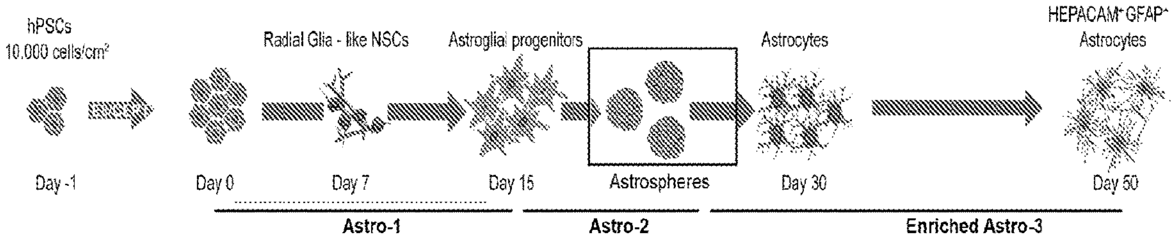

FIG. 13B

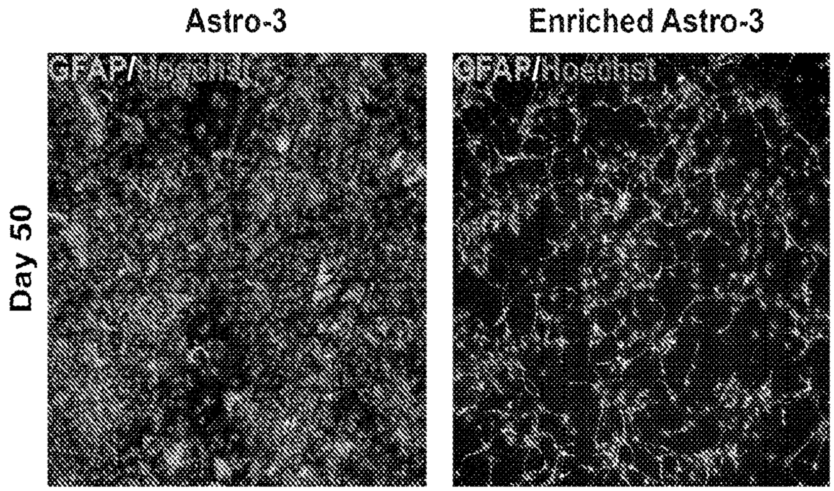

FIG. 13C

Enriched Astro 3 Medium between Day 22-50:

Base medium: DMEM/F12 + N2 supplement + B27 supplement (complete) - Fetal Bovine Serum 2% or lipid concentrate 2%

- CNTF 10 ng/mL
- LIF 10 ng/mL

Plus the following reagents to generate enriched Astro-3 medium:

- Jagged 1 (10 ng/ml)
- DLL-1 (10 ng/ml)
- Triiodothyronine (also known as T3 is a thyroid hormone) (40 ng/ml)
- Phorbol ester (200 nM)
- Forskolin 2 uM
- Neuregulin-1 (20 ng/ml)
- Ascorbic acid (200 uM)

RADIAL GLIA AND ASTROCYTE DIFFERENTIATION FROM HUMAN PLURIPOTENT STEM CELLS

CROSS-REFERENCE TO RELATED APPLICATIONS

This application is the U.S. National Stage Application of International Application No. PCT/US2021/018659, filed on Feb. 19, 2021, which claims the benefit of the U.S. Provisional Application No.: 62/979,429, filed Feb. 21, 2020, the disclosures of each of which are explicitly incorporated by reference herein in their entirety.

GOVERNMENT LICENSE RIGHTS

This invention was made with Government support awarded by NIH Regenerative Medicine Program of the National Institutes of Health (NIH Common Fund) and National Center for Advancing Translational Sciences (NCATS). The Government has certain rights in the invention.

BACKGROUND OF THE INVENTION

Field of the Invention

This disclosure relates fields of biochemistry, cell biology, bioengineering, drug development and stem cell biology, as well as related fields, and to compositions and methods useful for culturing and differentiating pluripotent stem cells.

Description of Related Art

Pluripotency is a remarkable cellular state that allows differentiation of stem cells into any cell type of the human body. Vertebrate pluripotent stem cells, including embryonic stem cells (ESCs) and induced pluripotent stem cells (iPSCs), undergo extensive self-renewal and have the potential to differentiate into all somatic cell types. Generating desired cell types from pluripotent stem cells hold enormous potential for drug discovery, disease modeling and regenerative medicine. For instance, development of new therapeutic agents for human use as well as neuroscience research would greatly benefit from directed differentiation of human pluripotent stem cells (hPSCs) into relevant cells of the nervous system, such as astrocytes. Unfortunately, existing procedures of producing astrocytes from vertebrate pluripotent stem cells can be inefficient, undefined and lengthy. They also show poor reproducibility, require expensive supplements and often generate chaotic mixtures of different cell lineages. Therefore, a need exists for improved methods for generating cells exhibiting at least some characteristics of astrocytes cells from vertebrate pluripotent stem cells.

SUMMARY OF THE INVENTION

It is against the above background that the instant invention provides certain advantages over the prior art.

Described and included among the embodiments of the present invention are methods useful for production and maintenance in culture of differentiated vertebrate cells exhibiting at least some characteristics of vertebrate radial glia-like cells of central nervous system. Among other characteristics, the radial glia-like cells produced by the methods described in the present disclosure, possess the ability to differentiate into one or more cell types exhibiting the characteristics of the cells found in vertebrate nervous system, such as neurons, oligodendrocytes and/or astrocytes as described and included among the embodiments of the present invention. Also described and included among the embodiments of the present invention are methods useful for production and maintenance in culture of vertebrate cells exhibiting at least some characteristics of astrocytes. Among other things, the methods described in this document are highly efficient, cost-effective, reproducible, scalable and suitable for automation. For example, some embodiments of the methods described in the present disclosure can be performed by using an automated culture system. The methods described in this document are useful, among other things, for example, in drug discovery and development and in neuroscience research, including, but not limited to, high-throughput screening of compounds for various applications, including drug development and toxicity screening, in disease modeling and research, as well as in regenerative therapies, such as cell replacement and repair of damaged central nervous system, and cell and tissue engineering. The advantages of the compositions, kits and methods of the present invention are discussed throughout this document and illustrated in the accompanying figures.

Although this invention as disclosed herein is not limited to specific advantages or functionalities (such as, for example, methods of producing, in culture, radial glia-like cells, methods of producing a culture of astrocyte-like cells, methods of culturing astrocyte-like cells, compositions useful for culturing and differentiating pluripotent stem cells, cell cultures useful for culturing and differentiating pluripotent stem cells, compositions comprising at least one cultured radial glia-like cell detectably expressing at least one marker disclosed herein, compositions comprising at least one cultured radial glia-like cell produced by the methods disclosed herein, cell cultures comprising at least one cultured radial glia-like cell detectably expressing at least one marker disclosed herein, cell cultures comprising at least one cultured radial glia-like cell produced by the methods disclosed herein and expressing at least one marker disclosed herein compositions comprising at least one cultured astrocyte-like cell exhibiting flat, star-shaped, and/or sphere morphology detectably expressing at least one marker disclosed herein, compositions comprising at least one cultured astrocyte-like cell exhibiting flat, star-shaped, and/or sphere morphology produced by the methods disclosed herein, cell cultures comprising at least one cultured astrocyte-like cell exhibiting flat, star-shaped, and/or sphere morphology and detectably expressing at least one marker disclosed herein, cell cultures comprising at least one cultured astrocyte-like cell exhibiting flat, star-shaped, and/or sphere morphology produced by the methods disclosed herein and expressing at least one marker disclosed herein), the invention provides a method of producing, in culture, radial glia-like cells, the method comprising:

(a) plating vertebrate pluripotent stem cells on a substrate-coated surface of a culture vessel at a density of 1,000-100,000 cells/$cm^2$;
(b) incubating the plated vertebrate pluripotent stem cells in a first culture medium;
(c) replacing the first culture medium with a second culture medium comprising:
  (i) an effective amount or concentration of one or more inhibitors of BM P pathway,
  (ii) an effective amount or concentration of one or more activators of Notch pathway,
  (iii) one or more cytokines of interleukin-6 family; and
(d) culturing the plated vertebrate pluripotent stem cells in the second culture medium;

thereby producing radial glia-like cells.

In one aspect of the methods disclosed herein, the substrate comprises vitronectin, laminin 521, Matrigel, and/or Geltrex.

In one aspect of the methods disclosed herein, plating vertebrate pluripotent stem cells, comprises plating at the cell density of 2,000-90,000 cells/$cm^2$; 3,000-80,000 cells/$cm^2$; 4,000-70,000 cells/$cm^2$; 5,000-50,000 cells/$cm^2$, and/or 10,000-30,000 cells/$cm^2$.

In one aspect of the methods disclosed herein, incubating the plated vertebrate pluripotent stem cells in the first culture medium comprises incubating for 12-48 hours.

In one aspect of the methods disclosed herein, culturing the plated vertebrate pluripotent stem cells in the second culture medium comprises culturing for at least 5-20 days.

In one aspect of the methods disclosed herein, the first culture medium is a first defined culture medium, wherein the first defined culture medium is E8, E8 Flex, StemFlex, mTeSR, StemFit, or mouse embryonic fibroblast (MEF)-conditioned medium.

In one aspect of the methods disclosed herein, the first culture medium comprises an effective concentration of Chroman 1 or a derivative thereof, an effective concentration of Emricasan or a derivative thereof, an effective concentration of trans-ISRIB, and an effective concentration of polyamines comprising putrescine, spermine, and spermidine.

In one aspect of the methods disclosed herein, the effective concentration of Chroman 1 or the derivative thereof is about 4 nM to about 80 μM, the effective concentration of Emricasan or the derivative thereof is about 100 nM to about 80 μM, the effective concentration of trans-ISRIB is about 50 nM to about 80 μM, and wherein putrescine, spermine, and spermidine is each at a concentration of about 0.5 nM to 1 mM.

In one aspect of the methods disclosed herein, the first culture medium further comprises at least one inhibitor of Rho-associated protein kinase (ROCK).

In one aspect of the methods disclosed herein, the one or more ROCK inhibitors comprise one or more of Chroman 1 or a derivative thereof, Y27632, blebbistatin, or thiazovivin.

In one aspect of the methods disclosed herein, during the culturing in the second culture medium, the cells being cultured detectably express one or more radial glia cell markers at approximately 4-10 days after start of the culturing in the second culture medium.

In one aspect of the methods disclosed herein, the radial glia-like cells detectably express one or more of Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HES5), SRY-Box Transcription Factor 21 (SOX21), and PAX6 protein.

In one aspect of the methods disclosed herein, during the culturing in the second culture medium, the cells being cultured detectably express one or more astrocyte markers at approximately 5-20 days after start of the culturing.

In one aspect of the methods disclosed herein, the one or more astrocyte markers comprise S100 Calcium-Binding Protein B (S100B).

In one aspect of the methods disclosed herein, during the culturing in the second culture medium, cells being cultured detectably express one or more neural stem cell markers at approximately 2-10 days after start of the culturing.

In one aspect of the methods disclosed herein, the one or more neural stem cell markers comprise PAX6.

In one aspect of the methods disclosed herein, the radial glia-like cells are multipotent stem cells capable of differentiating into neuron-like cells, oligodendrocyte-like cells, and/or astrocyte-like cells.

In one aspect of the methods disclosed herein, the vertebrate pluripotent stem cells are induced pluripotent stem cells or embryonic pluripotent stem cells.

In one aspect of the methods disclosed herein, the vertebrate pluripotent stem cells are human pluripotent stem cells.

In one aspect of the methods disclosed herein, the second culture medium is a second defined culture medium, wherein the second defined culture medium is DMEM-F12, E6, Neurobasal medium, or minimal essential medium (MEM).

In one aspect of the methods disclosed herein, the second defined culture medium comprises N2 supplement and/or B27 supplement without vitamin A.

In one aspect of the methods disclosed herein, the one or more inhibitors of the Bone Morphogenetic Proteins (BMP) pathway comprise one or more of LDN-193189, LDN-214117, LDN-212854, DMH2, ML 347, UK 383367, K 02288, Dorsomorphin, Noggin, Chordin, Follistatin, or Gremlin.

In one aspect of the methods disclosed herein, the effective amount or concentration of the one or more inhibitors of the BMP pathway comprise 2 nM-40 μM LDN-193189.

In one aspect of the methods disclosed herein, the second culture medium further comprises an effective amount or concentration of one or more Platelet-Derived Growth Factor protein.

In one aspect of the methods disclosed herein, the one or more Platelet-Derived Growth Factor protein is Platelet-Derived Growth Factor-AA (PDGF-AA), Platelet-Derived Growth Factor-BB (PDGF-BB), or Platelet-Derived Growth Factor-AB (PDGF-AB).

In one aspect of the methods disclosed herein, the effective amount or concentration of the one or more Platelet-Derived Growth Factor protein is about 1 ng/mL-800 ng/mL.

In one aspect of the methods disclosed herein, the effective amount or concentration of the one or more activators of Notch pathway in the second culture medium comprise one or more of Jagged 1 protein, Jagged 2 protein, and Delta-Like protein 1 (DLL1), Delta-Like protein 2 (DLL2), or Delta-Like protein 3 (DLL3).

In one aspect of the methods disclosed herein, the one or more activators of Notch pathway in the second culture medium comprise one or both of 1 ng/mL-800 ng/mL Jagged 1 protein and 1 ng/mL-800 ng/mL Delta-Like protein 1 (DLL1).

In one aspect of the methods disclosed herein, the one or more cytokines of interleukin-6 family in the second culture medium comprise one or more of Oncostatin M protein, Ciliary-Derived Neurotrophic Factor protein (CNTF) and Leukemia-Inhibitory Factor protein (LIF).

In one aspect of the methods disclosed herein, each of the one or more Oncostatin M protein, Ciliary-Derived Neurotrophic Factor protein (CNTF) and Leukemia-Inhibitory Factor protein (LIF) is present in the second culture medium in a concentration of 1 ng/mL-800 ng/mL.

In one aspect of the methods disclosed herein, the culturing in the second culture medium comprises changing the second culture medium approximately every 20-28 hours.

In one aspect of the methods disclosed herein, the culturing in the second culture medium comprises one or more steps of passaging cells being cultured when they become confluent.

In one aspect of the methods disclosed herein, the one or more steps of passaging the cells are performed at 1:3 to 1:5 ratio of confluent cell culture to fresh medium.

In one aspect of the methods disclosed herein, the culturing in the second culture medium comprises 3-7 of the passaging steps.

The invention also provides a method of producing a culture of astrocyte-like cells, comprising performing at least one of the methods disclosed herein and, after the step of generating the radial glia-like cells, culturing the radial glia-like cells for approximately 5-30 days in a third culture medium, an effective amount or concentration of one or more activators of Notch pathway, and an effective amount or concentration of one or more cytokines of Interleukin-6 (IL-6) family, thereby generating the culture of the astrocyte-like cells.

In one aspect of the methods disclosed herein, the third culture medium is a third defined culture medium.

In one aspect of the methods disclosed herein, the third defined culture medium is DMEM-F12, Neurobasal medium, minimal essential medium (MEM), or BrainPhys neuronal medium.

In one aspect of the methods disclosed herein, the third defined culture medium comprises N2 supplement and/or complete B27 supplement.

In one aspect of the methods disclosed herein, the one or more activators of Notch pathway in the third culture medium comprise one or more of Jagged 1 protein, Jagged 2 protein, and Delta-Like protein 1 (DLL1), Delta-Like protein 2 (DLL2), or Delta-Like protein31 (DLL3).

In one aspect of the methods disclosed herein, the effective amount or concentration of the one or more activators of Notch pathway in the third culture medium comprise one or both of 1 ng/mL-800 ng/mL Jagged 1 protein and 1 ng/mL-800 ng/mL Delta-Like protein 1 (DLL1).

In one aspect of the methods disclosed herein, the one or more cytokines of interleukin-6 family in the third culture medium comprise one or more of Oncostatin M protein, Ciliary-Derived Neurotrophic Factor protein (CNTF) and Leukemia-Inhibitory Factor protein (LIF).

In one aspect of the methods disclosed herein, the effective amount or concentration of each of the one or more Oncostatin M protein, Ciliary-Derived Neurotrophic Factor protein (CNTF) and Leukemia-Inhibitory Factor protein (LIF) is present in the third culture medium in a concentration of 1-800 ng/mL.

In one aspect of the methods disclosed herein, the culturing in the third culture medium comprises changing the third culture medium approximately every 24-72 hours.

In one aspect of the methods disclosed herein, the culturing in the third culture medium comprises one or more steps of passaging cells being cultured when they become confluent.

In one aspect of the methods disclosed herein, the one or more passaging steps are performed at 1:2 ratio of confluent cell culture to fresh medium.

In one aspect of the methods disclosed herein, the culturing in the third culture medium comprises 1-3 passaging steps.

In one aspect of the methods disclosed herein, the astrocyte-like cells detectably express one or more of astrocyte markers.

In one aspect of the methods disclosed herein, the one or more astrocyte markers comprise S100 Calcium-Binding Protein B (S100B), Nuclear Factor 1 A-Type Protein (NFIA), Glial Fibrillary Acidic Protein (GFAP) and vimentin (VIM).

In one aspect of the methods disclosed herein, the astrocyte-like cells exhibit flat and/or star-shaped morphology.

In one aspect of the methods disclosed herein, during the culturing in a third culture medium detectable neuron-like cells are present at 10% or less of total cells in culture.

In one aspect of the methods disclosed herein, the third culture medium further comprises a chemically defined lipid concentrate at a concentration of approximately 2%, comprising one or more of arachidonic acid, cholesterol, DL-alpha-tocopherol acetate, linoleic acid, linolenic acid, myristic acid, oleic acid, palmitic acid, palmitoleic acid, and stearic acid or fetal bovine serum at a concentration of approximately 2%.

The invention also provides a method of culturing the astrocyte-like cells, comprising performing at least one of the methods disclosed herein, and further culturing the astrocyte-like cells in a fourth culture medium and an effective amount or concentration of one or more cytokines of interleukin-6 family, thereby enhancing maturation of astrocyte-like cells.

In one aspect of the methods disclosed herein, the fourth culture medium is a fourth defined culture medium.

In one aspect of the methods disclosed herein, the fourth defined culture medium is DMEM-F12, E6, Neurobasal medium, or minimal essential medium (MEM).

In one aspect of the methods disclosed herein, the fourth defined culture medium comprises N2 supplement and/or B27 supplement.

In one aspect of the methods disclosed herein, the one or more cytokines of interleukin-6 family comprise one or both of Ciliary-Derived Neurotrophic Factor protein (CNTF) and Leukemia-Inhibitory Factor protein (LIF).

In one aspect of the methods disclosed herein, the effective amount of concentration of each of the one or both of Ciliary-Derived Neurotrophic Factor protein (CNTF) and Leukemia-Inhibitory Factor protein (LIF) is present in a concentration of 1-800 ng/mL.

In one aspect of the methods disclosed herein, the fourth medium optionally is an enriched fourth defined culture medium, comprising an effective amount or concentration of one or more activators of Notch pathway and/or one or more thyroid hormone, phorbol ester, forskolin, neuregulin, and ascorbic acid.

In one aspect of the methods disclosed herein, the thyroid hormone is triiodothyronine and the one or more activators of Notch pathway in the fourth culture medium comprise one or more of Jagged 1 protein and Delta-Like protein 1 (DLL1).

In one aspect of the methods disclosed herein, the one or more activators of Notch pathway is about 1 ng/mL to about 800 ng/mL Jagged 1 protein and 1 ng/mL to about 800 ng/mL Delta-Like protein 1 (DLL1), and the concentration of thyroid hormone is about 1 ng/Ml to about 1000 ng/mL, the concentration of phorbol ester is about 1 nM to about 1000 nM, the concentration of forskoline is about 1 μM to about 200 μM, the concentration of neuregulin is about 1 ng/mL to about 1000 ng/mL, and the concentration of ascorbic acid is about 1 μM to about 1000 μM.

In one aspect of the methods disclosed herein, the culturing in the fourth culture medium is performed for at least approximately 40-60 hours.

In one aspect of the methods disclosed herein, the culturing in the fourth culture medium comprises changing the fourth culture medium approximately every 24-96 hours.

In one aspect of the methods disclosed herein, during the culturing in the fourth culture medium the astrocyte-like cells detectably express one or more of Hepatic and Glial Cell Adhesion Molecule (HEPACAM), glial fibrillary acidic protein (GFAP), CD44 protein, and vimentin (VIM).

In one aspect of the methods disclosed herein, during the culturing in the fourth culture medium the astrocyte-like cells exhibit star-shaped morphology and/or sphere morphology.

In one aspect of the methods disclosed herein, one or more steps of the method are performed by an automated system.

In one aspect of the methods disclosed herein, the fourth culture medium further comprises a chemically defined lipid concentrate at a concentration of approximately 2%, comprising one or more of arachidonic acid, cholesterol, DL-alpha-tocopherol acetate, linoleic acid, linolenic acid, myristic acid, oleic acid, palmitic acid, palmitoleic acid, and stearic acid or fetal bovine serum at a concentration of approximately 2%.

The invention also provides a composition, comprising at least one cultured radial glia-like cell detectably expressing at least one marker, wherein the at least one marker is Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HES5), SRY-Box Transcription Factor 21 (SOX21), or PAX6 protein.

In one aspect of the compositions disclosed herein, the at least one cultured radial glia-like cell is or was cryopreserved.

In one aspect of the compositions disclosed herein, composition, comprising at least one cultured radial glia-like cell detectably expressing at least one marker, wherein the at least one marker is Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HESS), SRY-Box Transcription Factor 21 (SOX21), or PAX6 protein.

In one aspect of the compositions disclosed herein, the at least one cultured radial glia-like cell is or was cryopreserved.

In one aspect of the compositions disclosed herein, the at least one cultured radial glia-like cell is or was cryopreserved in a cryopreservation medium comprising Chroman 1 and/or a derivative thereof, Emricasan and/or the derivative thereof, trans-ISRIB and polyamines comprising putrescine, spermine and spermidine.

In one aspect of the compositions disclosed herein, in the cryopreservation medium, Chroman 1 and/or the derivative thereof is or was at a concentration of about 4 nM to about 80 μM, wherein Emricasan and/or the derivative thereof is or was at a concentration of about 100 nM to about 80 μM, wherein trans-ISRIB is or was at a concentration of about 50 nM to about 80 μM, and wherein each of putrescine, spermine and spermidine is or was at a concentration of about 0.5 μM to 1 mM.

The invention also provides a composition, comprising at least one cultured radial glia-like cell produced by the methods disclosed herein and expressing at least one marker, wherein the at least one marker is Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HES5), SRY-Box Transcription Factor 21 (SOX21), or PAX6 protein.

The invention also provides a cell culture, comprising at least one cultured radial glia-like cell detectably expressing at least one marker, wherein the at least one marker is Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HESS), SRY-Box Transcription Factor 21 (SOX21), or PAX6 protein.

In one aspect of the cell cultures disclosed herein, the cell culture is grown from previously cryopreserved cells.

In one aspect of the cell cultures disclosed herein, the previously cryopreserved cells were cryopreserved in a cryopreservation medium comprising Chroman 1 and/or a derivative thereof, Emricasan and/or the derivative thereof, trans-ISRIB and polyamines comprising putrescine, spermine and spermidine.

In one aspect of the cell cultures disclosed herein, the previously cryopreserved cells are vertebrate pluripotent stem cells.

In one aspect of the cell cultures disclosed herein, the vertebrate pluripotent stem cells are induced pluripotent stem cells or embryonic pluripotent stem cells.

In one aspect of the cell cultures disclosed herein, the vertebrate pluripotent stem cells are human pluripotent stem cells.

In one aspect of the cell cultures disclosed herein, the previously cryopreserved cells are cultured radial glia-like cells detectably expressing Brain Lipid Binding Protein (BLBP), Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HESS), SRY-Box Transcription Factor 21 (SOX21), and PAX6 protein.

The invention also provides a cell culture, comprising at least one cultured radial glia-like cell produced by the methods disclosed herein and expressing at least one marker, wherein the at least one marker is Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HES5), SRY-Box Transcription Factor 21 (SOX21), or PAX6 protein.

The invention also provides a composition, comprising at least one cultured astrocyte-like cell exhibiting flat, star-shaped, and/or sphere morphology and detectably expressing at least one marker, wherein the at least one marker is S100 Calcium-Binding Protein B (S100B), Nuclear Factor 1 A-Type Protein (NFIA), Hepatic and Glial Cell Adhesion Molecule (HEPACAM), glial fibrillary acidic protein (GFAP), CD44 protein, or vimentin (VIM).

In one aspect of the compositions disclosed herein, the at least one cultured astrocyte-like cell is or was cryopreserved in a cryopreservation medium comprising Chroman 1 and/or a derivative thereof, Emricasan and/or the derivative thereof, trans-ISRIB and polyamines comprising putrescine, spermine and spermidine.

In one aspect of the compositions disclosed herein, in the cryopreservation medium, Chroman 1 and/or the derivative thereof is or was at a concentration of about 4 nM to about 80 μM, wherein Emricasan and/or the derivative thereof is or was at a concentration of about 100 nM to about 80 μM, wherein trans-ISRIB is or was at a concentration of about 50 nM to about 80 μM, and wherein each of putrescine, spermine and spermidine is or was at a concentration of about 0.5 μM to 1 mM.

The invention also provides a composition, comprising at least one cultured astrocyte-like cell exhibiting flat, star-shaped, and/or sphere morphology produced by the methods disclosed herein and expressing at least one marker, wherein the at least one marker is S100 Calcium-Binding Protein B (S100B), Nuclear Factor 1 A-Type Protein (NFIA), Hepatic and Glial Cell Adhesion Molecule (HEPACAM), glial fibrillary acidic protein (GFAP), CD44 protein, or vimentin (VIM).

The invention also provides a cell culture, comprising at least one cultured astrocyte-like cell exhibiting flat, star-shaped, and/or sphere morphology and detectably expressing at least one marker, wherein the at least one marker is S100 Calcium-Binding Protein B (S100B), Nuclear Factor 1 A-Type Protein (NFIA), Hepatic and Glial Cell Adhesion Molecule (HEPACAM), glial fibrillary acidic protein (GFAP), CD44 protein, or vimentin (VIM).

In one aspect of the cell cultures disclosed herein, detectable neuron-like cells are present at 10% or less of total cells in culture.

In one aspect of the cell cultures disclosed herein, the cell culture is grown from previously cryopreserved cells.

In one aspect of the cell cultures disclosed herein, the previously cryopreserved cells were cryopreserved in a cryopreservation medium comprising Chroman 1 and/or a derivative thereof, Emricasan and/or the derivative thereof, trans-ISRIB and polyamines comprising putrescine, spermine and spermidine.

In one aspect of the cell cultures disclosed herein, the previously cryopreserved cells are vertebrate pluripotent stem cells.

In one aspect of the cell cultures disclosed herein, the vertebrate pluripotent stem cells are induced pluripotent stem cells or embryonic pluripotent stem cells.

In one aspect of the cell cultures disclosed herein, the vertebrate pluripotent stem cells are human pluripotent stem cells.

In one aspect of the cell cultures disclosed herein, the previously cryopreserved cells are cultured radial glia-like cells detectably expressing Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HES5), SRY-Box Transcription Factor 21 (SOX21), and PAX6 protein.

In one aspect of the cell cultures disclosed herein, the previously cryopreserved cells are astrocyte-like cell exhibiting flat, star-shaped, and/or sphere morphology and detectably expressing one or more of S100 Calcium-Binding Protein B (S100B), Nuclear Factor 1 A-Type Protein (NFIA), CD44, HEPACAM, Glial Fibrillary Acidic Protein (GFAP), and vimentin (VIM). The invention also provides a cell culture, comprising at least one cultured astrocyte-like cell exhibiting flat, star-shaped, and/or sphere morphology produced by the methods disclosed herein and detectably expressing at least one marker, wherein the at least one marker is S100 Calcium-Binding Protein B (S100B), Nuclear Factor 1 A-Type Protein (NFIA), Hepatic and Glial Cell Adhesion Molecule (HEPACAM), glial fibrillary acidic protein (GFAP), CD44 protein, or vimentin (VIM).

These and other features and advantages of the instant invention will be more fully understood from the following detailed description taken together with the accompanying claims. It is noted that the scope of the claims is defined by the recitations therein and not by the specific discussion of features and advantages set forth in the instant description.

BRIEF DESCRIPTION OF THE DRAWINGS

The following detailed description of the embodiments of the instant invention can be best understood when read in conjunction with the following drawings, where like structure is indicated with like reference numerals and in which:

FIGS. 1A-B show a schematic illustration of the procedure for differentiation of human pluripotent stem cells. FIG. 1A shows a schematic pathway for differentiation of human pluripotent stem. FIG. 1B shows a schematic illustration of the procedure for differentiation of human pluripotent stem cells into radial glia-like cells and astrocyte-like cells and media used in the procedure.

FIG. 2A-D shows a schematic illustration of the procedure for differentiation of human pluripotent stem cells into radial glia-like cells and astrocyte-like cells. FIG. 2B shows components of the Astro 1 Medium used between day 0-15. FIG. 2C shows components of the Astro 2 Medium used between day 15-30. FIG. 2D shows components of the Astro 3 Medium used after day 30.

FIG. 3A shows at "Day 5," differentiating cells expressed the neural stem cell marker Paired Box Protein Pax-6 (PAX6), followed by the radial glia marker Brain Lipid Binding Protein (BLBP) at "Day 7." At "Day 15," the astrocyte marker S100 Calcium-Binding Protein B (S100B) was widely expressed. FIG. 3B shows at "Day 30," the culture was substantially composed of large cells with flat morphologies expressing the typical astrocyte markers S100B, Nuclear factor 1 A-type (NFIA), CD44, HEPACAM, glial fibrillary acidic protein (GFAP), and vimentin (VIM). FIG. 3C shows the astrocyte-like cells generated by the differentiation procedure were cryopreserved at "Day 30" or cultured for additional 20 days and passaged two times, which led to further cell maturation indicated by star-shaped morphologies and the expression of Hepatic and Glial Cell Adhesion Molecule (HEPACAM), CD44, glial fibrillary acidic protein (GFAP), and NFIA. The label "HOECHST" indicates Hoechst counterstain, which labels cell nuclei.

FIG. 5B shows exemplary images of the cells at different time points in the differentiation procedure.

FIG. 9A shows exemplary microscopic images illustrating comparable glycogen accumulation capacity of the iPSC-derived astrocyte-like cells produced by the differentiation procedure ("SCTL iPSC Astro") and commercially available iPSC-derived astrocyte-like cells ("Commercial iPSC Astro," sourced from Fujifilm Cellular Dynamics International). FIG. 9B shows a bar graph illustrating the reduction of baseline glutamate levels in the medium after 3-hour incubation with astrocytes.

FIG. 10A shows, in top panel, the images of neuronal cells were derived from a human ESC reporter cell line (SYN1:GFP; green fluorescent protein expressed under the control of the synapsin 1 promoter) and cultured for 13 days with (+iPSC Astro) and without (iPSC Astro) the astrocyte-like cells produced by the differentiation procedure. The bottom panel of FIG. 10A shows a line plot illustrating synapsin 1 expression in the neurons. FIG. 10B illustrates the results of the multi-electrode array experiments (Axion Biosystems) performed with glutamatergic neurons sourced from Fujifilm Cellular Dynamics International co-cultured with astrocyte-like produced by the differentiation procedure described in Example 1.

FIG. 12A shows a schematic illustration of a procedure for performing an automated differentiation procedure using CEPT at every passage (exposure to CEPT for 24 hours). FIG. 12B shows a representative microscopic image of astrocyte-like cells produced by an exemplary automated procedure at "Day 30" of the procedure.

FIGS. 13A-C show GFAP expression enhanced by using 3D sphere formation and enriched Astro-3 medium. FIG. 13A shows a schematic of enhanced protocol to incorporate sphere formation stage (boxed) between day 14 and day 28 of differentiation. FIG. 13B shows photomicrographs depict increased GFAP expression by astrocytes and more mature morphology in cultures treated with enriched Astro-3 medium. FIG. 13C shows components of the enriched Astro-3 Medium used between day 22-50 for differentiation of human pluripotent stem cells into radial glia-like cells and astrocyte-like cells.

Figure 3A:
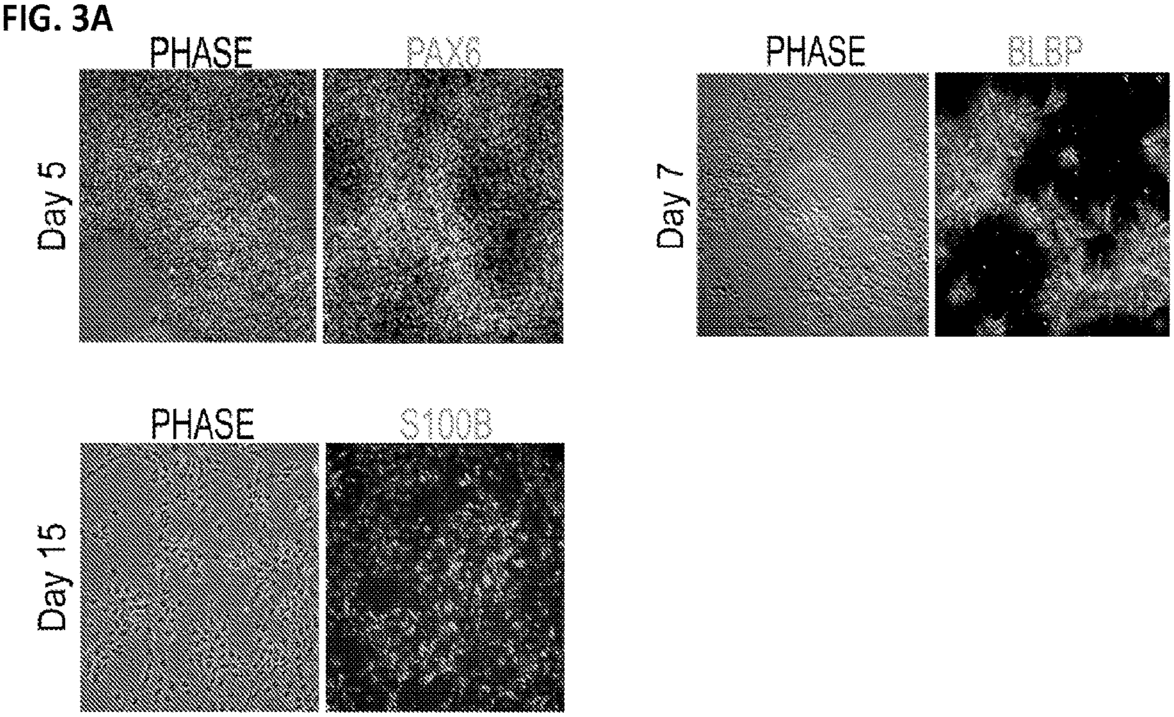
FIGS. 3A-C show representative images of the cells from different time points, indicated at the left border of each panel, of the differentiation procedure. The images labeled "PHASE" are phase-contrast microscopy images. The images labeled with the name of the specific proteins are microphotographs of the cells that were immunocytochemically stained with the indicated combinations of antibodies specific for the following proteins: TUJ1 (also known as beta-III Tubulin, neuronal marker); PAX6—neural stem cell marker PAX6; BLBP—radial glia marker Brain Lipid Binding Protein (BLBP); S100B—astrocyte marker S100 beta (S100B); NF-IA—astrocyte marker NFIA; VIM—astrocyte marker vimentin; GFAP—astrocyte marker glial fibrillary acidic protein; HEPACAM—astrocyte marker Hepatic and Glial Cell Adhesion Molecule.

Skilled artisans will appreciate that elements in the Figures are illustrated for simplicity and clarity and have not necessarily been drawn to scale. For example, the dimensions of some of the elements in the Figures can be exaggerated relative to other elements to help improve understanding of the embodiment(s) of the instant invention.

DETAILED DESCRIPTION OF THE INVENTION

All publications, patents and patent applications cited herein are hereby expressly incorporated by reference for all purposes.

Before describing the instant invention in detail, a number of terms will be defined. They are intended to facilitate the understanding of various embodiments of the invention in conjunction with the rest of the present disclosure and the accompanying figures. These terms and concepts may be further clarified and understood based on the accepted conventions in the fields of the present invention and the description provided throughout the present document and/or the accompanying figures. Some other terms can be explicitly or implicitly defined in other sections of this disclosure and in the accompanying figures and may be used and understood based on the accepted conventions in the fields of the present invention, the description provided throughout the present document and/or the accompanying figures. The terms not explicitly defined can also be defined and understood based on the accepted conventions in the fields of the present invention and interpreted in the context of the present document and/or the accompanying figures.

As used herein, the singular forms "a," "an," and "the" include plural referents unless the context clearly dictates otherwise.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the instant invention.

As used herein, the terms "invention," "the invention," "this invention" and "the present invention," are intended to refer broadly to all of the subject matter of this patent application and the claims below. Statements containing these terms should be understood not to limit the subject matter described herein or to limit the meaning or scope of the patent claims below. Covered embodiments of the invention are defined by the claims, not this summary or description. This description is a high-level overview of various aspects of the invention and introduces some of the concepts that are described and illustrated in the present document and the accompanying figures. This description is not intended to identify key or essential features of the claimed subject matter, nor is it intended to be used in isolation to determine the scope of the claimed subject matter. The subject matter should be understood by reference to appropriate portions of the entire specification, any or all figures and each claim. The present document describes and refers to various embodiments of the invention. No particular embodiment is intended to define the scope of the invention. Rather, the embodiments merely provide non-limiting examples of various methods, compositions, kits, systems etc. that are at least included within the scope of the invention. Some embodiments of the present invention are summarized below, while others are described and shown elsewhere in the present document.

For the purposes of describing and defining the instant invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, "about" or "approximately" are used herein to indicate that a value includes the inherent variation of error for the device, the method being employed to determine the value, or simply error-tolerance of a value. For example, the terms "about" or "approximately" may mean ±1%, ±5%, ±10%, ±15% or ±20% variation from a predetermined value.

As used herein, the terms "isolate," "separate" or "purify" and the related terms are not used necessarily to refer to the removal of all materials other than the components of interest from a sample. Instead, in some embodiments, the terms are used to refer to a procedure that enriches the amount of one or more components of interest relative to one or more other components present in the sample. In some embodiments, "isolation," "separation" or "purification" may be used to remove or decrease the amount of one or more components from a sample. For example, the expression "an isolated cell" can refer to a cell that has been substantially separated or purified away from other cells of a cell culture or an organism.

As used herein, the term "derived" and the related expressions referring to cells or a biological sample indicate that the cell or sample was obtained from the stated source at some point in time. For example, a cell derived from an organism can represent a primary cell obtained directly from the individual (that is, unmodified), or it can be modified, for example, by introduction of a recombinant vector, by exposure to or culturing under particular conditions, or immortalization. In some cases, a cell derived from a given source will undergo cell division and/or differentiation such that the original cell is no longer exists, but the continuing cells will be understood to derive from the same source. The term "derive," "derivation" and the related terms and expressions can also be used in this disclosure to refer to creation of a cell population from a different starting or preceding population or cell. For example, in each of the cases of a population of differentiated radial glia-like cells or astrocyte-like cells described in this disclosure, the starting population may be pluripotent stem cells, such as iPSCs. In case of a population of astrocyte-like cells described in this disclosure, the starting population may also be radial glia-like cells. Thus, astrocyte-like cells can be described as being derived from radial glia-like cell or cells and/or pluripotent stem cell or cells. Radial glia like-cells can be described as being derived from pluripotent stem cell or cells.

Throughout this specification, unless the context specifically indicates otherwise, the term "comprising" and the related terms ("comprise," "comprises," etc.), when used in this disclosure to describe various embodiments of the invention, are open-ended, meaning that they do not exclude additional elements and synonymous with terms "including," "containing" or "having." When an embodiment of the invention is described using the term "comprising," it is intended to include the embodiments, in which the term comprising is replaced with the terms "consisting" of or "consisting essentially of." In other words, the description of the embodiments of the invention described in this disclosure using the term "comprising" and the related terms also provides the description of the related embodiments that use "consisting of" or "consisting essentially of" instead of "comprising". The term "consisting of" excludes any elements (steps, ingredient etc.) not specified in the description. The term "consisting essentially of" is intended to exclude only those elements not specified in the description that do not materially affect the basic and novel characteristics of the embodiment.

As utilized in accordance with the instant disclosure, unless otherwise indicated, all technical and scientific terms shall be understood to have the same meaning as commonly understood by one of ordinary skill in the art.

Percentages disclosed herein can vary in amount by ±10, 20, or 30% from values disclosed and remain within the scope of the contemplated disclosure.

Unless otherwise indicated or otherwise evident from the context and understanding of one of ordinary skill in the art, values herein that are expressed as ranges can assume any specific value or sub-range within the stated ranges in different embodiments of the disclosure, to the tenth of the unit of the lower limit of the range, unless the context clearly dictates otherwise.

As used herein and in the drawings, ranges and amounts can be expressed as "about" a particular value or range. About also includes the exact amount. For example, "about 5%" means "about 5%" and also "5%." The term "about" can also refer to ±10% of a given value or range of values. Therefore, about 5% also means 4.5%-5.5%, for example.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z."

As used herein, the terms "culture," "cell culture" and related terms can be used to refer to a cell or a population of cells residing outside of an organism. These cells can be stem cells, primary cells isolated from an organism or obtained from a cell bank, animal, or blood bank, or secondary cells that are derived from such sources. Secondary cells can be immortalized for long-lived cell culture. A primary cell includes any cell of an adult or fetal organism apart from egg cells, sperm cells and stem cells. Examples of useful primary cells include, but are not limited to, skin cells, bone cells, blood cells, cells of internal organs and cells of connective tissue. A secondary cell is derived from a primary cell and can be immortalized for long-lived in vitro cell culture. A cell culture can be described as "pure" when it contains a sufficiently high proportion of cells of a desired types or type and sufficiently low proportion of other types of cells. It is to be understood that "pure," when used in the present disclosure in the context of cell culture and related processes, is a relative and not an absolute term. For example, a cell culture and/or cell population can be described as "pure" when it contains over 50%, over 55%, over 60%, over 65%, over 70%, over 75%, over 80%, over 85%, over 90%, over 95%, or approximately 100% (for example, at least 95%, at least 96%, at least 97%, at least 98%, at least 99%) of a desired cell type or types.

As used herein, the terms "culture," "culturing," "grow," "growing," "maintain," "maintaining," "expand," "expanding," etc., when referring to cell, tissue or organ culture or the process of culturing, can be used interchangeably to mean that a cell or a group of cells (the scope of which expression includes groups or pluralities of undifferentiated or differentiated cells, embryos, embryoid bodes, tissues or organs) is maintained outside the body (ex vivo and/or in vitro) under conditions suitable for survival, proliferation, differentiation and/or avoiding senescence. In other words, cultured cell or groups of cells are allowed to survive, and culturing can result in cell growth, differentiation, or division. In this context, the terms "growing" and "culturing" can be used interchangeably and can refer to maintaining living cells in culture under certain conditions. The terms above do not imply that all cells in the culture survive or grow or divide, as some may naturally senesce. Cells are typically cultured in media, which can be changed during the course of the culture. The so-called two-dimensional (2D) cell cultures grow on flat surfaces, typically in plastic vessels that can be coated with substrates (for example, vitronectin, laminin 521, Matrigel, Geltrex). Three-dimensional (3D) cultures are cultures in which biological cells are permitted to grow or interact with their surroundings in all three dimensions. 3D cultures can be grown in in a variety of artificial environments, such as, but not limited to, plates, flasks, bioreactors or small capsules in which the cells can grow into spheroids, spheres or neurospheres. 3D cultures include so-called scaffold-free and scaffold-based technologies. Scaffold-free methods employ, but are not limited to, the uses of low adhesion plates, hanging drop plates, micropatterned surfaces, and rotating bioreactors, magnetic levitation, and magnetic 3D bioprinting. Scaffolds are structures or materials that provide a structural support for cell attachment and, in some cases, differentiation. Scaffolds include solid scaffolds, sponges (such as cellulose sponges), protein-based scaffolds (such as collagen or gelatin-based scaffolds), hydrogels, nanofiber scaffolds, synthetic polymer scaffolds (for example, polycaprolactone or polystyrene scaffolds). In general, a culture environment includes consideration of such factors as the substrate for cell growth, cell density and cell contract, the gas phase, the medium, and temperature. Cells in culture are generally maintained under conditions known to be optimal for cell growth. Such conditions may include, for example, a temperature of approximately 37° C. and a humidified atmosphere containing approximately 5% CO2. The duration of the incubation can vary widely, depending on the desired results.

As used herein, the terms "medium," "culture medium," "culture solution," "growth medium" and the related terms and expression refer to a medium supporting the survival and/or growth of cells (including single cells and pluralities of cells), tissues, organoids, organs or parts thereof or embryonic structures (such as, but not limited to, morula, blastocoel, blastocyst or embryo). A medium is typically isotonic, and can be a liquid, a colloidal liquid, a gel, a solid and/or a semi-solid. A medium can be configured to provide a matrix for cell adhesion or support, or a separate support (such as a culture vessel surface or a scaffold) can be provided. A medium can include the components for nutritional, chemical, and structural support necessary for culturing a cell or cells. A chemically defined medium (or "defined medium") is a medium with known concentrations of all of its chemical components. In contrast, an undefined medium can contain complex biological components, such as serum albumin or serum, that do not have completely defined compositions. A conditioned medium is understood to be a previously used medium from cultured cells. It contains metabolites, growth factors, and extracellular matrix proteins secreted into the medium by the cultured cells, which can be beneficial for subsequent uses of such conditioned medium. Culture medium can be provided in a powdered form to be prepared prior to use, in a concentrated form to be diluted prior to use, or in a form to be used without further dilution. For example, a culture medium can be a sterile liquid, supplied as a "working solution" to be used without further dilution, in which case the culture medium. A working solution of culture medium can contain effective amounts or concentrations of one or more additives. In another example, a culture medium can be a gel containing effective amounts of one or more additives. When a culture medium is provided in a form requiring further preparation, such as a powder or a concentrate, one or more can be included in amounts or concentration intended to provide an effective amount or amounts after the medium is prepared. For example, a 2× concentrated medium may contain twice the effective amount or amounts of one or more additives intended to be included in the final "working" form of the medium. Culture medium typically contains one or more appropriate nutrient sources for growth and/or maintenance of cells it is intended to support, such as mammalian cells, including human cells. Culture medium maintains appropriate pH and osmolarity. Culture medium can contain natural ingredients, artificial ingredients and/or synthetic ingredients. Examples of natural ingredients are biological fluids (such as plasma, serum, lymph or amniotic fluid), tissue extracts (such as extracts of liver, spleen, tumors, leukocytes, bone marrow or animal embryos). Some examples of culture media composed of artificial ingredients ("artificial media") are MEM and DMEM. Artificial culture medium can be serum-containing culture medium, serum-free culture medium (which can contain defined qualities of purified growth factors, lipoproteins and other components provided by the serum), chemically defined culture medium or protein-free culture medium. Culture medium can comprise one or more of a buffer, one or more inorganic salt, essential amino acids, one or more carbohydrate, such as glucose, fatty acids, lipids, vitamins and trace elements. One example of a buffer is a so-called natural buffering system, in which gaseous CO2 balances with the CO32-/HCO3- content of the culture. Another example is a chemical buffering system, such as the one using 4-(2-hydroxyethyl)-1-piperazineethanesulfonic acid (HEPES), a zwitterionic buffering agent. Culture medium can contain a pH indicator, such as phenol red, which allows pH monitoring during cell growth. Inorganic salt or salts in the culture media supply sodium, potassium and calcium ions, provide osmotic balance and help regulating cell membrane potential. Essential amino acids, which cannot be synthesized by the cells, are included in the culture medium, but nonessential amino acids may also be included to improve cell growth and viability. Carbohydrates, such as glucose, galactose, maltose or fructose are included as a source of energy. Proteins and peptides, such as albumin, transferrin or fibronectin may also be included, as well as fatty acids and lipids, particularly in serum-free media. Vitamins essential for growth and proliferation of cells, such as B group vitamins, can also be included. Examples of trace elements added to culture media, particularly serum free media, are copper, zinc, and selenium. Some examples of the culture media are commercially available media, such as, but not limited to, Essential 8 Medium, CTS Essential 8 Medium, Essential 6 Medium, StemFlex Medium, CTS KnockOut SR Xeno-free Medium, KnockOut Serum Replacement, StemPro, mTeSR, mTeSR1, StemFit, Nutristem, L7 Medium, iPS-Brew, Neurobasal or BrainPhys.

In the context of cell culture, as used herein, the term "dissociating" can refer to a process of isolating cells from other cells or from a surface, such as a culture plate surface. For example, cells can be dissociated from an organ or a tissue by mechanical or enzymatic methods. In another example, cells that aggregate in vitro can be dissociated from each other. In yet another example, adherent cells are dissociated from a culture plate or other surface. Dissociation can involve breaking cell interactions with extracellular matrix (ECM) and substrates (for example, culture surfaces) or breaking the ECM between cells.

A "stem cell" is a cell characterized by the ability of self-renewal through mitotic cell division and the potential to differentiate into a tissue or an organ. Among stem cells, embryonic and somatic stem cells may be distinguished. For example, mammalian embryonic stem cells may reside in the blastocyst and give rise to embryonic tissues, whereas somatic stem cells may reside in adult tissues for the purpose of tissue regeneration and repair.

An "adult stem cell," which can also be termed "somatic stem cell," is a stem cell found, in an organism, among differentiated cells in a tissue or organ and can differentiate to yield some or all of the specialized cell times in the tissue or organ. Somatic stem cells can be grown in culture. When differentiating into specialized cells, they typically generate intermediate cells called "precursor" or "progenitor" cells. Somatic stem cells and progenitor cells can be described as "multipotent" or "oligopotent," depending on their degree of potency. Some examples of somatic stem cells are: hematopoietic stem cells that give rise to all the types of blood cells (red blood cells, B lymphocytes, T lymphocytes, natural killer cells, neutrophils, basophils, eosinophils, monocytes and macrophages); mesenchymal stem cells that include bone marrow stromal stem cells and skeletal stem cells and can give rise to bone cells (osteoblasts and osteocytes), cartilage cells (chondrocytes), fat cells (adipocytes), and stromal cells that support blood formation; neural stem cells that can give rise to nerve cells (neurons), astrocytes and oligodendrocytes; epithelial stem cells in the lining of the digestive tract that can give rise to absorptive cells, goblet cells, Paneth cells, and enteroendocrine cells; skin stem cells that occur in the basal layer of the epidermis (and can give rise to keratinocytes) and at the base of hair follicles (and can give rise to both the hair follicle and to the epidermis). A tissue-specific progenitor cell is a cell devoid of self-renewal potential that is committed to differentiate into cells of a specific organ or tissue. Certain somatic stem cell types can differentiate into cell types seen in organs or tissues other than those expected from the somatic stem cell's origin. This phenomenon is called "transdifferentiation."

As used herein, the term "stem cell" and the related terms and expressions refer to animal cells that are capable of dividing and renewing themselves for long periods, are unspecialized, and can give rise to specialized cell types. Stem cells are capable of dividing and renewing themselves for long periods. Unlike, for example, muscle cells, blood cells, or nerve cells—which do not normally replicate themselves—stem cells may replicate many times or proliferate. If the resulting cells continue to be unspecialized, like the parent stem cells, the cells are said to be capable of long-term self-renewal.

As used herein, the term "cell line" typically refers to a cell culture developed from a single cell of a multicellular organism. Cells of a cell line have a relatively uniform genetic makeup. Some cell lines originate from stem cells. Some cell lines originate from naturally occurring cancerous cells that underwent genetic modifications (such as one or more mutations or introductions of viral genes) leading to uncontrolled proliferation. Some cell lines originate from the cells that have been artificially immortalized by various methods.

As used herein, the term "self-renewal," when used in reference to cells, describes their ability to divide and generate at least one daughter cell with the self-renewing characteristics of the parent cell, although one or more of other daughter cells may commit to a particular differentiation pathway. For example, a self-renewing hematopoietic stem cell can divide and form one daughter stem cell and another daughter cell committed to differentiation in the myeloid or lymphoid pathway. Non self-renewing cells can still undergo cell division to produce daughter cells, neither of which have the differentiation potential of the parent cell type, but instead generates differentiated daughter cells.

As used herein, the terms "pluripotent," "pluripotency" and the related terms and expressions refer to animal cells or cell populations with the ability to give rise to progeny that can undergo differentiation, under appropriate conditions, into cell types that collectively demonstrate characteristics associated with cell lineages from all of the three germ layers (endoderm, mesoderm, and ectoderm). For example, the expression "pluripotent stem cell characteristics" refers to characteristics of a cell or a cell population that distinguish pluripotent stem cells or their populations from other cells. The ability to give rise to progeny that can undergo differentiation, under the appropriate conditions, into cell types that collectively demonstrate characteristics associated with cell lineages from all of the three germ layers (endoderm, mesoderm, and ectoderm) is a pluripotent stem cell characteristic. Cell morphologies as well as expression or non-expression of certain combinations of molecular markers are also pluripotent stem cell characteristics. Pluripotent stem cells (PSCs) include embryonic stem cells (ESCs) and induced pluripotent stem cells (iPSCs). Embryonic stem cells (ESCs) are derived from embryos and, under appropriate conditions, they can remain undifferentiated (unspecialized) in culture. An embryonic stem cell line is a line of ESCs cultured under the conditions that allow proliferation without differentiation for months to years. Under other conditions, for example, if the cells are allowed to clump together to form embryoid bodies, they begin to differentiate spontaneously.

As used herein, the term "radial glia cells" (singular—"radial glia cell") refers to specific cells that transiently exist during the neurogenic and gliogenic phases of brain development in the vertebrate embryo. They can also be referred to as "radial glial cells" or "radial glial progenitor cells" and can be considered multipotent stem cells. During embryonic development, the bodies of the radial glia cells are found in the ventricular zone of the developing neural tube. In vivo, radial glial cells give rise to all neurons of the cerebral cortex and also produce certain lineages of glia cells, including astrocytes and oligodendrocytes. Radial glial cells exist transiently during development and are generally not considered somatic stem cells.

As used herein, the term "astrocytes" (singular—"astrocyte), which can be referred collectively as "astroglia" are glia cells in vertebrate central nervous system. Astrocyte have a characteristic star shape. Astrocytes are known to perform many functions, including structural, biochemical and cytoprotective (for example, detoxification) support of other cells of the central nervous system, energy supply to neurons, ion balance maintenance, immunological functions, critical component of the blood-brain barrier, and a role in central nervous system repair (for example, scar formation). Astrocytes are also known to propagate intercellular calcium ion waves in response to stimulation and release transmitter. Accordingly, astrocytes may have neural signaling functions.

As used herein, the expression "induced pluripotent stem cell" (iPSC) refers to a pluripotent stem cell artificially derived from a non-pluripotent cell. For example, human iPSCs are artificially derived from a human non-pluripotent cell. iPSCs can be derived by introducing products of specific sets of pluripotency-associated genes, or "reprogramming factors," into a given cell type and/or exposing non-pluripotent cells to particular conditions.

As used herein, the term "non-pluripotent cells" refer to mammalian cells that are not pluripotent cells. Examples of such cells include differentiated cells, somatic stem cells, as well as progenitor cells. Some non-pluripotent cells maintain a degree of potency, some of the examples being somatic stem cells and progenitor cells.

As used herein, the term "cell potency" describes a cell's ability to differentiate into other cell types. A cell can be designated as a pluripotent cell, a multipotent cell (which can differentiate into several but not all cell types, for example, umbilical cord blood stem cells and mesenchymal stem cells) or an oligopotent cell (having the ability to differentiate into a few cell types, for example, lymphoid cells or vascular cells). Under current understanding, potency exists on a continuum. Thusly, the boundaries between the divisions of cells based on potency may be fluid and are not necessarily limiting.

As used herein, the terms "progenitor cell" or "precursor cell" refers to the cells that can typically differentiate to form one or more kinds of cells. A "precursor cell" or "progenitor cell" can be any cell in a cell differentiation pathway that is capable of differentiating into a more mature cell. Progenitor cells can be primary cells obtained from an organism, cells proliferated in culture or cells derived from stem cells. Progenitor cells can be an early descendant or a pluripotent stem cell or a pluripotent cell itself. Progenitor cells can also be a partially differentiated multipotent cell or reversibly differentiated cell. The term "precursor cell population" refers to a group of cells capable of developing into a more mature or differentiated cell type. A precursor cell population can comprise cells that are pluripotent, cells that are stem cell lineage restricted (cells capable of developing into less than all lineages, or into, for example, only cells of neuronal lineage), and cells that are reversibly stem cell lineage restricted. Therefore, the term "progenitor cell" or "precursor cell" may be a "pluripotent cell" or "multipotent cell."

As used herein, the terms "astrocytic progenitor" or "astrocyte progenitor" refer to cells that can generate progeny that are mature astrocytes. Generally, the cells express some of the phenotypic markers that are characteristic of the astrocyte lineage. The astrocyte marker may be expressed on the cell surface or internally. Examples of astrocyte markers include S100 beta, glial fibrillary acidic protein (GFAP), glutamine sythetase, GLAST and GLT1.

"Differentiation" is the process by which a less specialized cell becomes a more specialized cell type. For example, early development of a multicellular animal is characterized by the rapid proliferation of embryonic cells, which then differentiate to produce the many specialized types of cells that make up the tissues and organs of the multicellular animal. As cells differentiate, their rate of proliferation usually decreases. Some types of differentiated cells never divide again, but many differentiated cells are able to resume proliferation as required to replace cells that have been lost as a result of injury or cell death. Some cells divide continuously throughout life to replace cells that have a high rate of turnover in adult multicellular animals. Examples of differentiated cells include, but are not limited to, cells from a tissue selected from bone marrow, skin, skeletal muscle, fat peripheral blood. Exemplary differentiated cell types include, but are not limited to, fibroblasts, tissue and hepatocytes, cardiomyocytes, myoblasts, neurons, osteoblasts, osteoclasts, and lymphocytes.

As used herein, the terms "modified cells" and the related terms and expressions encompass all cells that have been or are derived from the cells that have been artificially modified, by any methods, as compared to the original or cells from which they are derived. Modified cells can be produced from primary cells, secondary cells, stem cells, cultured cells and/or other modified cells. Modifications include, but are not limited to, genetic modification or engineering, in which case modified cells can be referred to as "genetically modified" or "genetically engineered." Genetic modification can be accomplished by various methods that result in incorporation of foreign or heterologous nucleic acids into the cells being modified. Some examples of such methods are transduction by a virus or a viral vector, or transfection of isolated nucleic acids into cells through transient pores in the cell membrane. Other modifications include exposing the source cells to biological and non-biological molecules or factors or culture conditions. Some examples of modified cells are iPSCs, genetically modified cells, including those used for gene therapies, one example being gene-edited cells, such as those modified using CRISPR/Cas9, TALENs or ZFNs.

As used herein, the term "vessel" refers to a container, dish, plate, flask, bottle, cell culture tube, a bioreactor and the like, which can be used to culture, maintain or grow a cell, group of cells, tissue or organ ex vivo or in vitro. Suitable vessels include, for example, multi-well plates, wells of multi-well plates, dishes, tubes, flasks, bottles and reactors.

As used herein, the terms "stabilize" and the related terms and expressions used in reference to cells (for example, "stabilizing a cell") refer to reduction of negative cell responses, such as cell death or senescence. For example, stem cells and other cells can die in response to cell passaging, dissociation, isolation, freezing and/or thawing. In other words, the above conditions can reduce cell viability. Embodiments of the compositions, methods and kits described therein can mitigate the reduction of cell viability and improve cell survival, which can be described as cell stabilization.

As used herein, the term "passage," "passaging" and the related terms and expressions used in the context of cell culture refer to subculturing, which typically involves transfer of cells from a previous culture into a fresh growth medium. Passaging is performed to ensure propagation of cells in culture. Cell proliferation in culture reduced or ceases when the cells reduce the capacity of the culture vessels and/or media to support further cell growth. For example, cells in adherent cultures may occupy all the available substrate and have no room left for expansion, while cells in suspension cultures exceed the capacity of the medium to support further growth. To keep cells in a culture at an optimal density for continued growth and to stimulate further proliferation, the culture must be expanded and fresh medium supplied. To divide the culture of adherent cells, for example, a monolayer culture of cells, such as cultures of differentiating PSCs described on the present disclosure, the cells are first dissociated, for example, by enzymatic dissociation. Enzymatic dissociation can be performed by removing the incubation medium from the plates, adding to the plates a buffer, such as PBS and an enzymatic dissociation reagent, such as Accutase, TrypLE or Trypsin available from Thermo Fisher Scientific, incubating the cells with the buffer and dissociation reagent under appropriate conditions, and harvesting the resulting dissociated cells by centrifugation, sedimentation, filtering or other appropriate methods. The dissociated cells are transferred into similar or equivalent reaction vessels, such as flasks, with fresh media, to result in a lower cell density.

As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule (for example, molecules having a molecular weight of less than 10,000 AMU). When a presence, absence of amount of a marker can be experimentally observed or detected, such a marker or its amount can be described as "observable" or "detectable."

As used herein, in the context of observable or detectable markers of cell development or differentiation, "expression" refers to the production of a gene product (which can be a nucleic acid, such as RNA, or a protein) as well as the level or amount of production of a gene product. Thus, determining the expression of a specific marker refers to detecting either the relative or absolute amount of the marker (which can mean detecting expression of RNA or protein) that is expressed or simply detecting (which can mean detecting expression of RNA or protein) the presence or absence of the marker. If expression of RNA or protein corresponding to the marker is detected, the marker can be said to be "detectably expressed." For most markers described herein, the symbols provided are those developed and/or recognized by HUGO Gene Nomenclature Committee of European Bioinformatics Institute.

As used herein, the term "cryopreservation," as well as related terms and expression, refer to is a process or processes, as well as the results of such process or processes, by which cells, groups of cells or cell cultures are preserved by cooling to sub-zero temperatures.

The embodiments of the present invention were envisioned at least in part based on the discoveries discussed below. By manipulating critical cell signaling pathways at defined time points by using various additives and their combinations, the inventors discovered a procedure for converting human pluripotent stem cells in culture into cells resembling radial glia-like cells of the central nervous system. The radial glia-like cells produced by the inventors were subjected to a further differentiation procedure and produced, in a highly reproducible fashion, a homogenous population of cells resembling human astrocytes. Extensive morphological, molecular and electrophysiological characterization experiments confirmed astrocyte-like properties of the resulting differentiated cells, including expression of typical astrocyte markers.

Astrocytes play crucial roles in normal brain development, synaptic function, neurodegenerative diseases, brain injury, and various other pathological conditions (such as, but not limited to, Alzheimer's disease, amyotrophic lateral sclerosis (ALS), also known as Lou Gehrig's disease, Down syndrome, autism, intellectual disability, epilepsy, opioid addiction and aging). Among other things, the discoveries made by the inventors and described in the present disclosure resulted in processes of culturing human astrocyte-like cells from a scalable source, such as induced pluripotent stem cells (iPSCs). Such processes are highly desirable for biomedical research and development of new therapeutics, but the mechanism of astrogliogenesis, the process by which astrocytes are generated in the human brain, remains elusive, and the processes for culturing astrocyte-like cells available until now were variable, inefficient, and lengthy (lasting up to several months). Based on the their discoveries described in the present disclosure, the inventors conceived processes (methods) for producing in culture cells capable of differentiating into cells exhibiting at least some characteristics of radial glia cells (radial glia-like cells), including human radial glia-like cells, processes (methods) of producing in culture of cells exhibiting at least some characteristics of vertebrate astrocyte cells (astrocyte-like cells), including human astrocyte-like cells, as well as various compositions and kits related to the above processes.

The processes described in the present disclosure allow production of desired cell populations (for example, radial glia-like cells and/or astrocyte cells) in culture in a highly efficient, controlled, and step-wise manner. The processes described in the present disclosure overcame the scientific and technical limitations of previously published methods, such as poor efficiency, extensive length (up to 6 months and longer), requirement of cell sorting, genetic manipulation, and use of animal products, such as fetal bovine serum (FBS). Some embodiments of the processes described in the present disclosure produce cultures of radial glia-like cells from iPSCs. Some other embodiments of the processes described in the present disclosure produce cultures of astrocyte-like cells from radial glia-like cells. The processes described in the present disclosure are highly advantageous and superior to the previously known processes for various reasons. For example, the processes described in the present disclosure produce in culture substantially pure populations of radial glia-like cells and astrocyte-like cells without any genetic manipulation. In another example, the processes described in the present disclosure produce in culture substantially pure populations of radial glia-like cells and astrocyte-like cells using chemically defined conditions. Some embodiments of the processes described in the present disclosure do not require the use of undefined culture media components, such as fetal bovine serum (FBS). Such embodiments can be carried out under chemically defined conditions compatible with good manufacturing practice (GMP) approaches, clinical translation, and cell therapy. In one more example, the processes described in the present disclosure produce in culture substantially pure populations of radial glia-like cells and astrocyte-like cells in shorter periods of time than previously known methods. In yet one more example, the processes described in the present disclosure produce cultures of radial glia-like cells and astrocyte-like cells in which the proportion of desired cell types (radial glia-like cells and astrocyte-like cells) is higher than in the previously known processes.

The embodiments of the processes described in the present disclosure can be combined to produce cultures of astrocyte-like cells from iPSCs. By identifying and simultaneously manipulating key developmental pathways, some embodiments of the processes described in the present disclosure achieved derivation of astrocyte-like cells from iPSCs with over 90% efficiency (meaning that 90 out of 100 total resulting cells detectably express one or more astrocyte markers, such as S100B and/or NFIA) in less than 30 days. Remarkably, the processes described in the present disclosure produce cultures of astrocyte-like cells from iPSCs by largely bypassing the generation of neurons (neurogenesis). Astrogliogenesis (production of astrocyte-like cells) from iPSCs in culture without preceding neurogenesis has not previously been achieved. Using various methods, iPSC-derived astrocyte-like cells produced by the methods described in the present disclosure were extensively characterized (for example, based on their morphology, gene expression, protein expression, electrophysiology and biochemistry) and compared to their in vivo counterparts, which confirmed the resemblance of iPSC-derived astrocyte-like cells produced by the methods described in the present disclosure to naturally found astrocytes. Using a robotic cell culture system, the inventors automated the procedure for generating vertebrate radial glia-like cells and astrocyte-like cells from pluripotent stem cells. The inventors also conceived various applications and uses of their processes (methods), compositions and kits, including high-throughput applications and uses requiring large numbers of standardized cells of high quality. Among other things, various embodiments of the invention described in the present disclosure can be used in drug discovery and development, toxicity screenings, disease modeling and research (for example, directed to better understanding of molecular mechanisms of neurodegenerative diseases), cell and tissue engineering, cell replacement therapies (for example, cell replacement due to injury to the central, peripheral, and autonomous nervous system, stroke, hypoxia/ischemia of newborns, and other chronic diseases), cellular delivery of enzymes, compounds or genes for inherited disease or cancer therapy (for example, enzyme replacement therapy for lysosomal storage diseases, migratory astrocytes to deliver chemotherapeutic drugs or genes to brain tumor cells), and regenerative medicine.

Methods

Various methods (processes) are envisioned and included among the embodiments of the present invention. Among the methods according to embodiments of the present invention are methods of producing in culture of cells or cell cultures containing cells with at least some defined characteristics. Such methods can also be referred to "methods of cell production," "method of cell culture production," "methods of generating," "methods of culturing," "methods of differentiating," "differentiation method," "differentiation process" and by other related terms and phrases, which can be used interchangeably in reference to methods of producing cells or cell cultures. One example of such methods is a method of producing or generating multipotent cells, which are in turn capable of differentiating into cells exhibiting at least some characteristics of astrocyte cells. The multipotent cells produced by such methods exhibit at least some characteristics of radial glial cells, such as expression of one or more of Brain Lipid Binding Protein (BLBP), CD133 (Prominin 1), ASPM, BIRC5 (Survivin), FAT1, HES5, SOX21, or PAX6. Accordingly, such multipotent cells can be referred to as "cells exhibiting at least some characteristics of radial glia cells," "radial glia-like cells," "cells resembling radial glia cells" and by other related terms and expressions. Cells exhibiting at least some characteristics of radial glia cells, or radial glia-like cells, along with the relevant characteristics, are discussed further in this disclosure. One more example of a method according to embodiments of the present invention is a method of producing or generating cells exhibiting at least some characteristics of astrocyte cells, such as flat and/or star-shaped morphology, expression of one or more of S100 Calcium-Binding Protein B (S100B), Nuclear Factor 1 A-Type Protein (NFIA), Glial Fibrillary Acidic Protein (GFAP), vimentin or Hepatic and Glial Cell Adhesion Molecule (HEPACAM). Cells exhibiting at least some characteristics of astrocyte cells produced according to the embodiments of the methods of the present invention can also be referred to as "astrocyte-like cells," "cells resembling astrocytes" and by other related terms and expressions. Cells exhibiting at least some characteristics of astrocyte cells, along with the relevant characteristics, are discussed further in this disclosure. The methods according to the above embodiments of the present invention and other embodiments related to cell production are conducted in culture and can be referred to as "methods of culturing" or "culturing." Such methods typically proceed from, as starting materials or intermediate products, less differentiated cells possessing higher potency (such as pluripotent cells, progenitor cells, multipotent cells or oligopotent cells) and proceed to, as intermediate and/or end products, more differentiated cells with lower potency (such as multipotent cells, progenitor cells, oligopotent cells or differentiated cells). Accordingly, the methods can be referred to as "methods of differentiating cells," even if the end product is or contains the cells that are not completely differentiated.

In some exemplary embodiments, the methods use pluripotent stem cells (PSCs) as a starting material. Such PSCs can be vertebrate PSCs, including mammalian PSCs or human PSCs (hPSCs). PSCs used in the methods according to the embodiments of the present invention can be isolated from natural sources or artificially derived PSCs, such as induced PSCs (iPSCs). Accordingly, the methods can be referred to as "methods of differentiating PSCs," for example, methods of differentiating hPSCs, methods of differentiating PSCs, etc. PSCs can be maintained and expanded in culture, such as monolayer culture or appropriate 3D culture systems (for example, those using microcarriers) in a defined medium, such as, but not limited to, E8, E8 Flex, StemFlex, StemPro, mTeSR, mTeSR1, StemFit, Nutristem, L7 Medium or iPS-Brew. The above maintenance and/or expansion of PSCs can be conducted as a part of the methods according to the embodiments of the present invention, or outside of such methods. In other words, cell production methods according to the embodiments of the present invention are not limited by the steps or processes employed to provide PSCs used for further steps, unless such limitations are explicitly stated. For example, if PSCs are simply listed as a starting material or "provided" without further limitations, then the processes used to obtain, culture, expand or grow PSCs are not intended to be incorporated into the method. PSCs can be provided in the form of monolayer cultures exhibiting, for example, typical PSC morphology, which may include prominent nucleoli and/or high nuclear-to-cytoplasmic ratio, cell growth in colonies, and expression of pluripotency-associated markers such as, but not limited to, OCT3/4, NANOG, SSEA-4, TRA-1-60, TRA-1-81 and/or Alkaline Phosphatase. In another example, PSCs can be provided in the form of 3D cultures or attached to microcarriers.

Cell production methods according to the embodiments of the present invention can include a step of plating vertebrate pluripotent stem cells PSCs (which can be ESCs or iPSCs), such as human PSCs, for example, human iPSCs, on a vitronectin-coated surface of a culture vessel at a density of approximately 5,000-50,000 cells/$cm^2$, such as, but not limited to, a plating density of approximately 5,000-40,000 cells/$cm^2$, approximately 5,000-20,000 cells/$cm^2$, approximately 10,000-50,000 cells/$cm^2$, approximately 10,000-40,000 cells/$cm^2$, or approximately 10,000-20,000 cells/$cm^2$. Some embodiments of the cell production methods may not include the plating step. In such embodiments, the PSCs may be provided at the start of a method as an adherent monolayer culture of a specified density, for example, at a density of approximately 5,000-50,000 cells/$cm^2$, such as, but not limited to, a plating density of approximately 5,000-40,000 cells/$cm^2$, approximately 5,000-20,000 cells/$cm^2$, approximately 10,000-50,000 cells/$cm^2$, approximately 10,000-40,000 cells/$cm^2$, or approximately 10,000-20,000 cells/$cm^2$.

Cell production methods according to the embodiments of the present invention can include a step of incubating plated vertebrate PSCs (which can be ESCs or iPSCs), such as human PSCs, for example, human iPSCs, in a culture medium comprising at least one inhibitor of Rho-associated protein kinase (ROCK). It is to be understood that the above incubation step is optional, and may not be included in some embodiments of cell production methods according to the embodiments of the present invention. The culture medium for the above incubation step, which can be referred to as "first culture medium" or "incubation medium," can be a defined culture medium (in which case it can be referred to as "first defined culture medium" or "defined incubation medium"), although using other types of media is also envisioned. Some non-limiting examples of the defined media suitable for incubating PSCs are E8, E8 Flex, StemFlex, mTeSR, StemFit, or mouse embryonic fibroblast (MEF)-conditioned medium. The first culture medium contains an effective amount or concentration of at least one (one or more) ROCK inhibitor compound. Some non-limiting examples of ROCK inhibitors are Chroman 1 or its derivatives, Y27632, blebbistatin, or thiazovivin. In some embodiments, the medium for the above incubation step contains Chroman 1, and can further contain one or more of an effective concentration of Emricasan or a derivative thereof, an effective concentration of trans-ISRIB and an effective concentration of polyamines comprising putrescine, spermine and spermidine. In an exemplary embodiment, the medium contains Chroman 1 or a derivative thereof is about 4 nM to about 80 μM, Emricasan or a derivative thereof at about 100 nM to about 80 μM, trans-ISRIB at about 50 nM to about 80 μM, and putrescine, spermine and spermidine (collective referred to as "polyamines" is each at a concentration of about 0.5 nM to 1 mM. The above combination of Chroman 1 or derivative thereof, Emricasan or a derivative thereof, trans-ISRIB and polyamines can be referred to as "CEPT." In an exemplary embodiment, the medium is E8. A period of time for incubating the plated PSCs is approximately 12 to approximately 24 hours, for example, from 12 hours±1.2 hours to 24 hours±2.4 hours, such as 12, 13, 14, 15, 16, 17, 18, 19, 20, 21, 22, 23 or 24 hours.

In the embodiments of cell production methods including the above-described incubation step, after the above-described incubation step, the first culture medium in the PSC culture is replaced with a culture medium (which can be referred to as "second culture medium" or "first differentiation medium"), containing an effective amount or concentration of one or more inhibitors of the BMP pathway, an effective amount or concentration of one or more activators of Notch pathway, an effective amount or concentration of one or more cytokines of interleukin-6 (IL-6) family, and an effective amount or concentration of Platelet-Derived Growth Factor (PDGF) protein. Some examples of suitable inhibitors of the BMP pathways are LDN-193189, Dorsomorphin, Noggin, Chordin, Follistatin or Gremlin. In one example, the second culture medium comprises about 2 nM-40 μM LDN-193189. In some other examples, the second culture medium can comprise one or more of about 2 nM-40 μM LDN-193189, about 2 nM-40 μM LDN-214117, about 2 nM-40 μM LDN-212854, about 2 nM-40 μM DMH2, about 2 nM-40 μM ML 347, about 2 nM-40 μM UK 383367, about 2 nM-40 μM K 02288, about 5 nM-40 μM Dorsomorphin, about 5 ng/mL-500 ng/mL Noggin, about 5 ng/mL-500 ng/mL Chordin, about 5 ng/mL-500 ng/mL Follistatin or about 5 ng/mL-500 ng/mL Gremlin. Some examples of suitable activators of Notch pathway are Jagged 1 protein, Jagged 2 protein, and Delta-Like protein 1 (DLL1), Delta-Like protein 2 (DLL2), or Delta-Like protein 3 (DLL3). In one example, the second culture medium comprises one or both of one or both of 1 ng/mL-800 ng/mL Jagged 1 protein and 1 ng/mL-800 ng/mL Delta-Like protein 1 (DLL1). Some examples of suitable cytokines of IL-6 family are Oncostatin M protein, Ciliary-Derived Neurotrophic Factor protein (CNTF) and Leukemia-Inhibitory Factor protein (LIF). In one example, each of Oncostatin M protein, Ciliary-Derived Neurotrophic Factor protein (CNTF) and Leukemia-Inhibitory Factor protein (LIF) is present in the second culture medium in a concentration of 1-800 ng/mL. Examples of suitable PDGF proteins are Platelet-Derived Growth Factor-AA protein (PDGF-AA), Platelet-Derived Growth Factor-AB protein (PDGF-AB) or Platelet-Derived Growth Factor-BB protein (PDGF BB). The second culture medium can be a defined culture medium (in which case it can be referred to as "second defined culture medium" or "first defined differentiation medium"), although using other types of media is also envisioned. Some non-limiting examples of the suitable defined media are DMEM-F12, E6, Neurobasal medium, or minimal essential medium (MEM). In some embodiments, the second defined culture medium comprises N2 supplement and B27 supplement without vitamin A. In some embodiments, the second culture medium contains CEPT.

Vertebrate PSCs (which can be ESCs or iPSCs), such as human PSCs, for example, human iPSCs, are cultured in the second culture medium for approximately 168-360 hours, for example, from 168 hours±17 hours to 360 hours±36 hours, such as 168-396 hours, 192-396 hours, 192-396 hours, 240-396 hours, 264-396 hours, 288-396 hours, 312-396 hours, 336-396 hours, 360-396 hours, 151-360 hours, 192-360 hours, 192-360 hours, 240-360 hours, 264-360 hours, 288-360 hours, 312-360 hours, or 336-360 hours. During the culturing in the second culture medium, the medium can be changed approximately every 20-28 hours, for example, from every 20±2 hours to every 28±3 hours, such as approximately every 20, 21, 22, 23, 24, 25, 26, 27 or 28 hours. During the culturing in the second culture medium, the cells being cultured can be passaged when they become confluent. The passaging can be performed at 1:3 to 1:5 ratio (such as 1:3, 1:3.5, 1:4, 1:4.5, or 1:5 ratio) of confluent cell culture to fresh medium. The culturing in the second culture medium can include 3-7 (for example, 3, 4, 5, 6 or 7) of the passaging steps.

The culturing of vertebrate PSCs (which can be ESCs or iPSCs), such as human PSCs, for example, human iPSCs, in the second culture medium induces or initiates differentiation of the vertebrate PSCs. At the end of culturing in the second culture medium, the cell culture contains approximately 50%-100% of radial glia-like cells (approximately 50-100 out of 100 cells expressing radial glia marker BLBP). For example, at the end of culturing in the second culture medium, the culture can contain approximately 50%, approximately 60%, approximately 70%, approximately 80%, approximately 90% or over 90% (such as approximately 91%, 92%, 93%, 94%, 95%, 96%, 97%, 98%, 99%, or 100%) of radial glia-like cells. Accordingly, during the culturing in the second culture medium, it is appropriate to refer to the cells as differentiating, such as differentiating vertebrate PSCs. During subsequent step or steps (discussed elsewhere in this disclosure), radial glia-like cells produced by culturing vertebrate PSCs in the second culture medium, are capable of producing astrocyte-like cells when subjected to the method steps described further in this disclosure. Radial glia-like cells arise (appear) in the culture being cultured in the second culturing media at various time points after the start of the culturing. Radial glia-like cells appearing in the culture can be characterized by detectable expression of one or more radial glia cell markers. Expression of one or more radial glia cell markers can be detected in the differentiating cells cultured in the second culture medium at approximately 120-216 hours (for example, approximately 120 hours, approximately 144 hours, approximately 168 hours, approximately 192 hours, or approximately 216 hours after the start of the culturing). One example of a radial glia cell marker is Brain Lipid Binding Protein (BLBP). Other examples of radial glia cell markers are CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HESS), and SRY-Box Transcription Factor 21 (SOX21). Another example of a radial glia cell marker is PAX6 protein. In one embodiment, radial glia like-cells detectably express each of BLBP, CD133 (Prominin 1), ASPM, BIRC5 (Survivin), FAT1, HESS, and SOX21, and PAX6.

Neural stem cells arise (appear) in cell cultured according to some embodiments of the methods described in the present disclosure at approximately day 5 after the start of culturing of pluripotent cells in the second culture medium. Neural stem cells appearing in the culture can be characterized by detectable expression of one or more neural stem cell markers. "Neural Stem Cells" is a broad term that includes early neuroepithelial stem cells expressing only PAX6, which transition into radial glia cells, expressing PAX6, BLBP, CD133 (Prominin 1), ASPM, BIRC5 (Survivin), FAT1, HES5, and SOX21. In other words, differentiation of the cells being cultured in the second culture medium can be described as proceeding first from pluripotent cells to neural stem cells, then to radial glia-like cells. Expression of one or more neural stem cell markers can be detected in the differentiating cells cultured in the second culture medium at approximately 72-168 hours (for example, approximately 72 hours, approximately 96 hours, approximately 120 hours, approximately 144 hours, or approximately 168 hours after the start of the culturing). One example of a neural stem cell markers is PAX6. At the end of the culturing in the second culture medium, the culture can contain varying proportions of radial glia-like cells (which may be characterized by expression of BLBP) and astrocyte-like cells (which may be characterized by expression of S100 Calcium-Binding Protein B (S100B)). At the end of culturing in the second culture medium, the cell culture also contains a detectable proportion of S100B-positive glial progenitor cells, and expression of S100B increases as the cells acquire astrocyte-like characteristics. For example, at the end of culturing in the second culture medium, the culture can contain approximately 50%, approximately 60%, approximately 70%, approximately 80%, approximately 90% or over 90% of cells detectably expressing S100B.

The cells exhibiting at least some characteristics of radial glia cells (radial glia-like cells), which are capable of differentiating into the cells exhibiting the at least some characteristics of the astrocyte cells (astrocyte-like cells), as well as mixtures of cells including one or both radial glia-like cells neural stem cells can be the end product of some, but not all, of the methods according to the embodiments of the present invention. Radial glia-like cells or a cell mixture including radial glia-like cells and neural stem cells can be an intermediate of some of the methods according to embodiments of the present invention, and can also be a starting material according to some other methods according to the embodiments of the present invention. Radial glia-like cells or cell mixtures including radial glia-like cells and neural stem cells can be prepared for cryopreservation and cryopreserved. The method steps related to cryopreservation can be incorporated into the methods of cell generation according to the embodiments of the present invention. Some of the methods and compositions relevant to cryopreservation are described further in this application in the section "Cryopreservation," although is to be understood that the description provided that section is not limiting, and that other compositions and methods can be employed for cryopreservation.

The cells exhibiting at least some characteristics of radial glia cells are capable of differentiating, under appropriate conditions, into cells exhibiting at least some characteristics of astrocyte cells. Methods of producing, in culture, cells exhibiting at least some characteristics of astrocyte cells (astrocyte-like cells) are included among the embodiments of the present invention. Radial glia-like cells, or cultures including such cells can be a starting material or intermediate of such methods. In one example, cells including the cells exhibiting at least some characteristics of radial glia cells (radial glia-like cells) are cultured under conditions inducing their differentiation into cells exhibiting the at least some characteristics of the astrocyte cells (astrocyte-like cells). Accordingly, embodiments of methods of producing astrocyte-like cells can include one or more steps of producing radial glia-like cells in culture according to the embodiments of the present invention. Alternatively, embodiments of methods of producing astrocyte-like cells do not need to include steps of producing radial glia-like cells, which can simply be provided at the start of the method of producing astrocyte-like cells.

In an embodiment of a method of producing astrocyte-like cells that includes one or more steps of producing radial glia-like cells in culture according to the embodiments of the present invention, after the step of culturing in the second culture medium, the second culture medium in the culture is replaced with a culture medium (which can be referred to as "third culture medium" or "second differentiation medium") containing an effective amount or concentration of one or more activators of Notch pathway, and an effective amount or concentration of one or more cytokines of interleukin-6 (IL-6) family. Alternatively, an embodiment of a method of producing astrocyte-like cells can start with a step of culturing radial glia-like cells in the third culture medium. Some examples of suitable activators of Notch pathway are Jagged 1 protein, Jagged 2 protein, and Delta-Like protein 1 (DLL1), Delta-Like protein 2 (DLL2), or Delta-Like protein 3 (DLL3). In one example, the second culture medium comprises one or both of one or both of 1 ng/mL-800 ng/mL Jagged 1 protein and 1 ng/mL-800 ng/mL Delta-Like protein 1 (DLL1). Some examples of suitable cytokines of IL-6 family are Oncostatin M protein, Ciliary-Derived Neurotrophic Factor protein (CNTF) and Leukemia-Inhibitory Factor protein (LIF). In one example, each of Oncostatin M protein, Ciliary-Derived Neurotrophic Factor protein (CNTF) and Leukemia-Inhibitory Factor protein (LIF) is present in the third culture medium in a concentration of 1-800 ng/mL. The third culture medium can be a defined culture medium (in which case it can be referred to as “third defined culture medium” or “second defined differentiation medium”), although using other types of media is also envisioned. Some non-limiting examples of the suitable defined media are DMEM-F12, E6, Neurobasal medium, minimal essential medium (MEM), or BrainPhys neuronal medium. In some embodiments, the third defined culture medium comprises N2 supplement and B27 supplement. The third culture medium also may or may not include fetal bovine serum albumin, for example, depending on the initial PSC line used. In some embodiments, the third culture medium contains a chemically defined lipid concentrate the third culture medium contains a chemically defined lipid concentrate comprising one or more of (for example, each of) arachidonic acid, cholesterol, DL-alpha-tocopherol acetate, linoleic acid, linolenic acid, myristic acid, oleic acid, palmitic acid, palmitoleic acid, and stearic acid. In some embodiments, the third culture medium contains CEPT. The cells are cultured in the third culture medium for approximately 120-720 hours, for example, from 120 hours±12 hours to 720 hours±72 hours, such as 120-720 hours, 144-720 hours, 120-360 hours or 144-720 hours, for example, approximately 120, 144, 168, 192, 216, 240, 264, 288, 312, 336, 360, 384, 408, 432, 456, 480, 504, 528, 552, 576, 600, 624, 648, 672, 696, or 720 hours. During the culturing in the third culture medium, the cells being cultured can be passaged when they become confluent. The passaging can be performed at 1:2 ratio of confluent cell culture to fresh medium. The culturing in the second culture medium can include 1-3, for example, 1, 2 or 3, of the passaging steps.

During the culturing of the cells in the third culture medium, the cells differentiate into astrocyte-like cells. At the end of culturing in the third culture medium, the cell culture contains a detectable proportion of astrocyte-like cells, for example, approximately 50-100% cells expressing astrocytes markers S100B and NF-IA, For example, at the end of culturing in the second culture medium, the culture can contain approximately 50%, approximately 60%, approximately 70%, approximately 80%, approximately 90% or over 90% (such as approximately 91%, 92%, 93%, 94%, 95%, 96%, 97%, 98%, 99%, or 100%) of astrocyte-like cells. Radial glia-like cells arise (appear) in the culture being cultured in the second culturing media at various time points after the start of the culturing. Astrocyte-like cells appearing in the culture can be characterized by detectable expression of one or more astrocyte markers. Expression of one or more astrocyte markers can be detected in the differentiating cells cultured in the third culture medium at approximately 0-360 hours after the start of the culturing the third culture medium (for example, approximately 0 hours, approximately 6 hours, 120 hours, approximately 180 hours, approximately 240 hours, approximately 300 hours, or approximately 360 hours after the start of the culturing). One example of an astrocyte marker is S100 Calcium-Binding Protein B (S100B). Another example of an astrocyte marker is Nuclear Factor 1 A-Type Protein (NFIA). Another example of an astrocyte marker is Glial Fibrillary Acidic Protein (GFAP). Another example of an astrocyte marker is vimentin. In one embodiment, astrocyte-like cells detectably express S100B, NFIA, GFAP and vimentin. Astrocyte-like cells appearing in the culture can also be characterized by a characteristic morphology, such as flat and/or star-shaped morphology. In one embodiment, astrocyte-like cells detectably express S100B, NFIA, GFAP and vimentin, and also exhibit flat and/or star-shaped morphology. During the culturing of the cells in the third culture medium, the cells differentiate into astrocyte-like cells with high efficiency. For example, at the end of the culturing in the third culture medium, detectable neuron-like cells characterized by expression of MAP2 and/or TUJ1 (beta-III Tubulin) are present at 10% or less or 5% or less of total cells in culture.

In some embodiments, the differentiation of human pluripotent stem cells (hPSCs), including human embryonic stem cells (hESCs) and induced pluripotent stem cells (iPSCs) is performed stepwise (see e.g., Example 6 ; FIG. 13A-C), which enables the generation of radial glial cells that can be differentiated into functional astrocytes. The instant inventors were first to identify and demonstrate that the combined use of gliogenic factors and appropriate cell culture conditions promote the efficient, fast, and targeted production of radial glial cells and astrocytes.

The surprising and unexpected findings that the stepwise process largely avoids the generation of neuronal cells (neurogenesis), which during in vivo brain development always precedes the emergence of astrocytes (astrogliogenesis) is of great relevance for basic and translational research including fundamental neurobiological studies (e.g., astrocytes providing neurotrophic support to neurons in co-culture models, astrocytes supporting maturation of neurons, astrocytes promoting formation of synapses and electrical activity), disease modeling (e.g., Alzheimer's disease, Parkinson's disease, Huntington's disease, Amyotrophic Lateral Sclerosis, Alexander disease and others), high-throughput screening, drug discovery, cell therapy, and regenerative medicine.

The procedure for sphere formation to enhance astrocyte maturation is schematically illustrated in FIG. 13. In some embodiments, the entire astrocyte differentiation procedure was executed as monolayer. In some embodiments, the entire astrocyte differentiation procedure was executed to include a sphere formation stage. During these procedures, the sphere formation step at Day 14 helped to mature cells and reduces cell passaging steps. Specifically, single cell dissociation was performed at day 14 and cells were maintained for 24 h in Astro-2 medium with CEPT in suspension to form spheres (100.000 cells/well of the 96-well plate with U bottom). One day later, spheres were then transferred to a vessel with low-cell attachment surface in Astro-2 medium. Media change was performed every other day. After one week in Astro-2 medium, Astro-3 containing DMEM/F12 media supplemented with N2 B27 complete, chemically defined lipid concentrate (2%), LIF (10 ng/ml), and CNTF (10 ng/ml) or enriched Astro-3 medium were introduced. The enriched Astro-3 contained DMEM/F12 media supplemented with N2 B27 complete, chemically defined lipid concentrate (2%), LIF (10 ng/ml), and CNTF (10 ng/ml), Jagged 1 (10 ng/ml), DLL-1 (10 ng/ml), triiodothyronine (also known as T3 is a thyroid hormone) (40 ng/ml), phorbol ester (200 nM), forskolin 2 μM, neuregulin-1 (20 ng/ml), and ascorbic acid (200 μM). Spheres were cultured in Astro-3 or enriched Astro-3 medium for another week with media change every other day. At day 28, spheres were single-cell dissociated by Accutase treatment and astrocytes were maintained as monolayer culture in Astro-3 or enriched Astro-3 media until day 50.

In some embodiments of a method of producing astrocyte-like cells, after the step of culturing in the third culture medium, the third culture medium in the culture is replaced with a culture medium (which can be referred to as "fourth culture medium" or "third differentiation medium") containing an effective amount or concentration of one or more cytokines of interleukin-6 (IL-6) family. Some examples of suitable cytokines of IL-6 family Ciliary-Derived Neurotrophic Factor protein (CNTF) and Leukemia-Inhibitory Factor protein (LIF). In one example, each of Ciliary-Derived Neurotrophic Factor protein and Leukemia-Inhibitory Factor protein is present in the fourth culture medium in a concentration of 1-800 ng/mL. The fourth culture medium can be a defined culture medium (in which case it can be referred to as "fourth defined culture medium" or "third defined differentiation medium"), although using other types of media is also envisioned. Some non-limiting examples of the suitable defined media are DMEM-F12, E6, Neurobasal medium, minimal essential medium (MEM), or BrainPhys neuronal medium. In some embodiments, the third defined culture medium comprises N2 supplement and B27 supplement. In some embodiments, the fourth culture medium contains CEPT. The fourth culture medium may or may not include fetal bovine serum (FBS), which can be included at a concentration of approximately 2%. The cells are cultured in the fourth culture medium up to 1,200 hours. During the culturing in the fourth culture medium, the medium can be changed approximately every 24-96 hours, for example, from every 20±2.4 hours to every 96±9.6 hours, such as approximately every 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94 or 96 hours.

During the culturing of the cells in the fourth culture medium, a substantial proportion of the cells in the culture continues to appear as astrocyte-like cells. For example, the culture can contain approximately 50%, approximately 60%, approximately 70%, approximately 80%, approximately 90% or over 90% of astrocyte-like cells. Astrocyte-like cells appearing in the culture can be characterized by detectable expression of one or more astrocyte markers. Expression of one or more astrocyte markers can be detected in the differentiating cells cultured in the third culture medium at approximately 0-1200 hours after the start of the culturing in the fourth culture medium. One example of an astrocyte marker is S100 Calcium-Binding Protein B (S100B). Another example of an astrocyte marker is Nuclear Factor 1 A-Type Protein (NFIA). Another example of an astrocyte marker is Glial Fibrillary Acidic Protein (GFAP). Another example of an astrocyte marker is vimentin. One more example of an astrocyte marker is Hepatic and Glial Cell Adhesion Molecule (HEPACAM). One more example of an astrocyte marker is CD44 protein. In one embodiment, astrocyte-like cells detectably express S100B, NFIA, GFAP, vimentin and HEPACAM. In one more embodiment, astrocyte-like cells detectably express CD44, GFAP, vimentin and HEPACAM. Astrocyte-like cells appearing in the culture can also be characterized by a characteristic morphology, such as flat and/or star-shaped morphology. In one embodiment, astrocyte-like cells detectably express one or more of the markers discussed above and also exhibit flat and/or star-shaped morphology.

The efficiency of the methods according to the embodiments of the present invention and described in the present disclosure can be adjusted by modifying certain parameters, which include but are not limited to, cell growth conditions, additive concentrations and the timing of the steps. The method steps described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of less differentiated cells possessing higher potency (such as pluripotent cells, progenitor cells, multipotent cells or oligopotent cells) to more differentiated cells with lower potency (such as multipotent cells, progenitor cells, oligopotent cells or differentiated cells). Examples of the conversion steps that can characterized by the above degrees of efficiency are conversion of PSC to radial glia-like cells, conversion of radial glia-like cells to astrocyte-like cells, or conversion of PSCs to astrocyte-like cells. In one example, starting with 1 million PSCs, at day 1, it is possible to generate 10-100 million radial glia-like cells at day 7 of culturing in the second culture media. In another example, starting with 1 million PSCs, at day 1 it is possible to generate a mixture of 100 million-1 billion astrocyte-like cells in 30 days.

Automation

Automated methods of cell culture are included among the embodiments of the present invention. Also included among the embodiments of the present invention are systems for performing or partially performing embodiments of the automated methods of the present invention. The systems according to the embodiments of the present invention may include various stations and/or components, some examples of which are described below. As used herein, the term "station" is broadly defined and includes any suitable apparatus or assemblies, conglomerations or collections of apparatuses or components suitable for carrying out a method according to the embodiments of the present invention. The stations need not be integrally connected or situated with respect to each other in any particular way. Systems according to the embodiments of the present invention may include any suitable arrangements of the stations with respect to each other. For example, the stations need not even be in the same room. But in some embodiments, the stations are connected to each other in an integral unit.

Automated cell culture methods and system for performing various methods according to embodiments of the present invention may be used to optimize conditions of various method steps and/or and to scale up production of cells produced by the methods, such us radial glia-like cells and/or astrocyte-like cells. In general, automated methods and systems according to the embodiments of the present invention minimize human intervention needed during cell culture procedures such as feeding, passing or harvesting of cells. In addition to freeing up laboratory personnel, the disclosed automated methods and systems allow for these techniques to be carried out in a reliable and reproducible manner. For example, a system for performing various methods according to embodiments of the present invention may include a station for robotic or automated cell culture, one example of which is CompacT SelecT® (Sartorius, Wilmington, DE) system. An automated cell culture system can grow, expand, and differentiate cells by performing methods according to the embodiments of the present invention. An automated cell culture system may be able to perform one or more steps required for cryopreservation of cells. An automated cell culture system can perform one or more cell culture processes, such as, but not limited to, seeding cell culture flasks or plates, maintaining cell cultures, for example, in cell culture flasks or plates, harvesting cells, pooling cells from harvesting flasks or plates, diluting cells for sub-culturing an plating, conducting cell counts, conducting cell viability assays, etc. An automated cell culture systems can include various stations, such as, but not limited to: a station for incubating cells, which is exemplified by an automated flask incubator maintaining a controlled environment (including controlled temperature, controlled gas composition and/or aseptic environment maintenance); a station for handling of flasks and other cell culture instruments, such as pipettes, which can be exemplified by a robotic arm or other type of robotic handler); a station for reagent dispensing, such as a robotic low volume dispenser; etc.

An automated cell culture system can include various computer components. An automated cell culture system embodiment, or parts of the system, may be controlled by a computer. For example, an automated cell culture system may include a computer-based station for generating reports. An automated cell culture system may include a computer-based station or components for data analysis. An automated cell culture system may include a computer, a processor, electronic memory, software instructions etc. An automated cell culture system may include software instructions for one or more of: system operation, workflow optimization, auditing and/or tracking of cell culture flasks or plates, etc. For example, an automated cell culture system may include an application software program to run programmed protocols on the robotic liquid handling system. The software program may run on an external device (for example, a portable computer, such as a tablet computer or a smartphone) which is in communication with a controller built into the robotic liquid handling system; the software program in some embodiments may coordinate control of the robotic liquid handling system and, when present, the external robotic system as well, to implement at least some steps of the methods according to the embodiments of the present invention. The software program may be programmed to alert users, for example, using sound, light, vibration, email alerts, text alerts, when intervention is needed, either due to a fault/error or due to a procedure being completed.

Computer-Based Calculations and Tools

The methods described in this disclosure can involve computer-based calculations and tools. Tools can be advantageously provided in the form of computer programs that are executable by a general-purpose computer system (which can be called "host computer") of conventional design. The host computer may be configured with many different hardware components and can be made in many dimensions and styles (for example, desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages.

The host computer system advantageously provides an interface via which the user controls operation of the tools. In the examples described herein, software tools are implemented as scripts (for example, using PERL), execution of which can be initiated by a user from a standard command line interface of an operating system such as Linux or UNIX. Commands can be adapted to the operating system as appropriate. In other embodiments, a graphical user interface may be provided, allowing the user to control operations using a pointing device. Thus, the present invention is not limited to any particular user interface.

Scripts or programs incorporating various features of the present invention may be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

Additives

Various additives can be used in the methods of cell production according to the embodiments of the present invention and in the related compositions and kits. Some additives and/or additive components are discussed below for clarity. It is understood that other additive and/or additive components may be used, even if they are not discussed below. In the context of the embodiments of the present invention, each of the components separately or a combination of components, can be referred to as "additive," "supplement," "active agent" or by other related terms, in singular or plural. Various formulations of the additives are envisioned. For example, additives can be formulated to contain amounts of one or more active agents sufficient to provide effective concentrations or effective amounts of the respective active agent or agents upon addition to culture media. In the context of the embodiment of the present invention, effective concentrations or effective amounts are those concentrations or amounts, respectively, of the one or more active agents that elicit desired effects on the cells exposed to the compositions, such as, but not limited to, improved survival (viability), cell stabilization, improved growth, reduced cell death, reduced senescence, improved growth, improved differentiation, etc. Additives are typically formulated so that they can be readily incorporated into culture media. For example, culture media additives can be provided in powdered form, as a tablet or as a capsule readily dissolvable in aqueous culture media. In another examples, additives can be provided as concentrated solutions or as suspensions to be added to culture media.

N-2 supplement is a chemically-defined, serum-free supplement based on Bottenstein, J. E. Cell Culture in the Neurosciences, Bottenstein, J. E. and Harvey, A. L., editors, p. 3-43, Plenum Press: New York and London (1985).

B-27 Supplement is an optimized serum-free supplement described, for example, in Brewer et al. Journal of Neuroscience Research 35:567-76, 1993.

As used herein, the term "Chroman 1" refers to (3S)—N-{2-[2-(Dimethylamino)ethoxy]-4-(1H-pyrazol-4-yl)phenyl}-6-methoxy-3,4-dihydro-2H-1-benzopyran-3-carboxamide. Chroman-related compounds or derivatives are structurally-related compounds (Chroman moiety-containing ROCK inhibitors), some of which are described in Chen et al., "Chroman-3-amides as potent Rho kinase inhibitors" Bioorganic and Medicinal Chemistry Letters 18:6406-6409

(2008) and LoGrasso et al., "Rho Kinase (ROCK) Inhibitors and Their Application to Inflammatory Disorders" Current Topics in Medicinal Chemistry 9:704-723 (2009). Chroman 1, its derivatives or related compounds can be supplied as a salt or in solution. An effective concentration of Chroman 1 (or its active derivative or a related compound) can be about 4 nM to about 80 μM, about 10 nM to about 20 μM, about 20 nM to about 10 μM or about 30 nM to about 500 nM, such as about 4 nM, 5 nM, 30 nM, 55 nM, 80 nM, 105 nM, 130 nM, 155 nM, 180 nM, 205 nM, 230 nM, 255 nM, 280 nM, 305 nM, 330 nM, 355 nM, 380 nM, 405 nM, 430 nM, 455 nM, 480 nM, 500 nM. 525 nM, 550 nM, 575 nM, 600 nM, 625 nM, 650 nM, 675 nM, 700 nM, 725 nM, 750 nM, 775 nM, 800 nM, 825 nM, 850 nM, 875 nM, 900 nM, 925 nM, 950 nM, 975 nM, 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM, 21 μM, 22 μM, 23 μM, 24 μM, 25 μM, 26 μM, 27 μM, 28 μM, 29 μM, 30 μM, 31 μM, 32 μM, 33 μM, 34 μM, 35 μM, 36 μM, 37 μM, 38 μM, 39 μM, 40 μM, 45 μM, 45 μM, 50 μM, 55 μM, 60 μM, 65 μM, 70 μM, 75 μM or 80 μM.

As used herein, the term "Emricasan" refers to 3-(2-(2-tert-butylphenylaminooxalyl) aminopropionylamino)-4-oxo-5-(2,3,5,6-tetrafluorophenoxy)pentanoic acid, with the structure shown in FIG. 1 . Emricasan-related compounds or derivatives are structurally-related compounds (such as Q-VD-OPh hydrate), some of which are described in Linton et al., "First-in-Class Pan Caspase Inhibitor Developed for the Treatment of Liver Disease" J. Med. Chem. 48:6779-6782, (2005). Emricasan, its derivatives or related compounds can be supplied as a salt or in solution. An effective concentration of Emricasan (or its active derivative or a related compound) can be about 5 nM to about 100 μM, about 5 nM to about 80 μM, about 200 nM to about 30 μM, about 300 nM to about 20 μM, for example, about 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 1 μM, 1.5 μM, 2 μM, 2.5 μM, 3 μM, 3.5 μM, 4 μM, 4.5 μM, 5 μM, 5.5 μM, 6 μM, 6.5 μM, 7 μM, 7.5 μM, 8 μM, 8.5 μM, 9 μM, 9.5 μM, 10 μM, 10.5 μM, 11 μM, 11.5 μM, 12 μM, 12.5 μM, 13 μM, 13.5 μM, 14 μM, 14.5 μM, 15 μM, 15.5 μM, 16 μM, 16.5 μM, 17 μM, 17.5 μM, 18 μM, 18.5 μM, 19 μM, 19.5 μM, 20 μM, 21 μM, 22 μM, 23 μM, 24 μM, 25 μM, 26 μM, 27 μM, 28 μM, 29 μM, 30 μM, 31 μM, 32 μM, 33 μM, 34 μM, 35 μM, 36 μM, 37 μM, 38 μM, 39 μM, 40 μM, 45 μM, 45 μM, 50 μM, 55 μM, 60 μM, 65 μM, 70 μM, 75 μM, 80 μM, 85 μM, 90 μM, 95 μM or 100 μM.

As used herein, the term "trans-ISRIB," which can be used interchangeably with the terms "ISRIB" or "ISRIB (trans-isomer)" refers to N,N'-((1r,4r)-cyclohexane-1,4-diyl) bis(2-(4-chlorophenoxy)acetamide) with the structure shown in FIG. 2. As described in Sidrauski et al., "Pharmacological brake-release of mRNA translation enhances cognitive memory" eLIFE 2:e00498 (2013), trans-ISRIB is 100-fold more potent (IC50=5 nM) than cis-ISRIB (IC50=600 nM) suggesting a stereospecific interaction with the cellular target. Trans-ISRIB can be supplied as a salt or in solution. An effective concentration of trans-ISRIB can be about 5 nM to about 80 μM, about 5 nM to about 50 μM, about 100 nM to about 6.25 μM, or about 200 nM to about 6.25 μM, for example, about 50 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 1 μM, 1.25 μM, 1.5 μM, 1.75 μM, 2 μM, 2.25 μM, 2.5 μM, 2.75 μM, 3 μM, 3.25 μM, 3.5 μM, 3.75 μM, 4 μM, 4.25 μM, 4.5 μM, 4.75 μM, 5 μM, 5.25 μM, 5.5 μM, 5.75 μM, 6 μM, 6.25 μM, 6.5 μM, 7 μM, 7.5 μM, 8 μM, 8.5 μM, 9 μM, 9.5 μM, 10 μM, 10.5 μM, 11 μM, 11.5 μM, 12 μM, 12.5 μM, 13 μM, 13.5 μM, 14 μM, 14.5 μM, 15 μM, 15.5 μM, 16 μM, 16.5 μM, 17 μM, 17.5 μM, 18 μM, 18.5 μM, 19 μM, 19.5 μM, 20 μM, 21 μM, 22 μM, 23 μM, 24 μM, 25 μM, 26 μM, 27 μM, 28 μM, 29 μM, 30 μM, 31 μM, 32 μM, 33 μM, 34 μM, 35 μM, 36 μM, 37 μM, 38 μM, 39 μM, 40 μM, 45 μM, 45 μM, 50 μM, 55 μM, 60 μM, 65 μM, 70 μM, 75 μM or 80 μM.

As used herein, the term "polyamines," as used herein, refers to one or more of the polycations putrescine, spermidine and spermine, which are known to interact with negatively charged macromolecules, such as DNA, RNA and proteins. An effective concentration of spermine can be about 0.5 nM to 1 mM, for example, about 0.5 nM, 20.5 nM, 40.5 nM, 60.5 nM, 80.5 nM, 100.5 nM, 120.5 nM, 140.5 nM, 160.5 nM, 180.5 nM, 200.5 nM, 220.5 nM, 240.5 nM, 260.5 nM, 280.5 nM, 300.5 nM, 320.5 nM, 340.5 nM, 360.5 nM, 380.5 nM, 400.5 nM, 420.5 nM, 440.5 nM, 460.5 nM, 480.5 nM, 0.5 μM, 20.5 μM, 40.5 μM, 60.5 μM, 80.5 μM, 100.5 μM, 120.5 μM, 140.5 μM, 160.5 μM, 180.5 μM, 200.5 μM, 220.5 μM, 240.5 μM, 260.5 μM, 280.5 μM, 300.5 μM, 320.5 μM, 340.5 μM, 360.5 μM, 380.5 μM, 400.5 μM, 420.5 μM, 440.5 μM, 460.5 μM, 480.5 μM, 500.5 μM, 520.5 μM, 540.5 μM, 560.5 μM, 580.5 μM, 600.5 μM, 620.5 μM, 640.5 μM, 660.5 μM, 680.5 μM, 700.5 μM, 720.5 μM, 740.5 μM, 760.5 μM, 780.5 μM, 800.5 μM, 820.5 μM, 840.5 μM, 860.5 μM, 880.5 μM, 900.5 μM, 920.5 μM, 940.5 μM, 960.5 μM, 980.5 μM or 1 mM. An effective concentration of spermidine can be about 0.5 μM to 1 mM, for example, approximately 0.5 nM, 20.5 nM, 40.5 nM, 60.5 nM, 80.5 nM, 100.5 nM, 120.5 nM, 140.5 nM, 160.5 nM, 180.5 nM, 200.5 nM, 220.5 nM, 240.5 nM, 260.5 nM, 280.5 nM, 300.5 nM, 320.5 nM, 340.5 nM, 360.5 nM, 380.5 nM, 400.5 nM, 420.5 nM, 440.5 nM, 460.5 nM, 480.5 nM, 0.5 μM, 20.5 μM, 40.5 μM, 60.5 μM, 80.5 μM, 100.5 μM, 120.5 μM, 140.5 μM, 160.5 μM, 180.5 μM, 200.5 μM, 220.5 μM, 240.5 μM, 260.5 μM, 280.5 μM, 300.5 μM, 320.5 μM, 340.5 μM, 360.5 μM, 380.5 μM, 400.5 μM, 420.5 μM, 440.5 μM, 460.5 μM, 480.5 μM, 500.5 μM, 520.5 μM, 540.5 μM, 560.5 μM, 580.5 μM, 600.5 μM, 620.5 μM, 640.5 μM, 660.5 μM, 680.5 μM, 700.5 μM, 720.5 μM, 740.5 μM, 760.5 μM, 780.5 μM, 800.5 μM, 820.5 μM, 840.5 μM, 860.5 μM, 880.5 μM, 900.5 μM, 920.5 μM, 940.5 μM, 960.5 μM, 980.5 μM or 1 mM. An effective concentration of putrescine can be about 0.5 μM to 1 mM, for example, approximately 0.5 nM, 20.5 nM, 40.5 nM, 60.5 nM, 80.5 nM, 100.5 nM, 120.5 nM, 140.5 nM, 160.5 nM, 180.5 nM, 200.5 nM, 220.5 nM, 240.5 nM, 260.5 nM, 280.5 nM, 300.5 nM, 320.5 nM, 340.5 nM, 360.5 nM, 380.5 nM, 400.5 nM, 420.5 nM, 440.5 nM, 460.5 nM, 480.5 nM, 0.5 μM, 20.5 μM, 40.5 μM, 60.5 μM, 80.5 μM, 100.5 μM, 120.5 μM, 140.5 μM, 160.5 μM, 180.5 μM, 200.5 μM, 220.5 μM, 240.5 μM, 260.5 μM, 280.5 μM, 300.5 μM, 320.5 μM, 340.5 μM, 360.5 μM, 380.5 μM, 400.5 μM, 420.5 μM, 440.5 μM, 460.5 μM, 480.5 μM, 500.5 μM, 520.5 μM, 540.5 μM, 560.5 μM, 580.5 μM, 600.5 μM, 620.5 μM, 640.5 μM, 660.5 μM, 680.5 μM, 700.5 μM, 720.5 μM, 740.5 μM, 760.5 μM, 780.5 μM, 800.5 μM, 820.5 μM, 840.5 μM, 860.5 μM, 880.5 μM, 900.5 μM, 920.5 μM, 940.5 μM, 960.5 μM, 980.5 μM or 1 mM.

As used herein, the terms "CEPT," "CEPT cocktail" or "CEPT small molecule cocktail" refer to a combination of effective amounts or concentrations of Chroman 1 or a derivative thereof, Emricasan or a derivative thereof, trans-ISRIB and polyamines.

As used herein, the term "Y27632" refers to trans-4-[(1R)-1-Aminoethyl]-N-4-pyridinylcyclohexanecarboxamide dihydrochloride. An effective concentration of Y27632 can be 1-100 μM.

As used herein, the term "blebbistatin" refers to (±)-1,2,3,3a-Tetrahydro-3a-hydroxy-6-methyl-1-phenyl-4H-pyrrolo[2,3-b]quinolin-4-one. An effective concentration of blebbistatin can be 5 nM-500 μM.

As used herein, the term "thiazovivin" refers to N-Benzyl-[2-(pyrimidin-4-yl)amino]thiazole-4-carboxamide. An effective concentration of thiazovivin can be 5 nM-200 μM.

As used herein, the term "LDN-193189" refers to 4-[6-[4-(1-Piperazinyl)phenyl]pyrazolo[1,5-a]pyrimidin-3-yl] quinoline dihydrochloride. An effective concentration of LDN-193189 can be about 2 nM-40 μM.

As used herein, the term LDN-214117 refers to 1-[4-[6-Methyl-5-(3,4,5-trimethoxyphenyl)-3-pyridinyl]phenyl]piperazine. An effective concentration of LDN-214117 can be 2 nM-40 μM.

As used herein, the term DMH2 refers to 4-[6-[4-[2-(4-Morpholinyl)ethoxy]phenyl]pyrazolo[1,5-a]pyrimidin-3-yl] quinoline. An effective concentration of DMH2 can be 2 nM-40 μM.

As used herein, the term LDN-212854 refers to 5-(6-(4-(1-Piperazinyl)phenyl)pyrazolo[1,5-a]pyrimidin-3-yl)quinoline. An effective concentration of LDN 212854 can be 2 nM-40 μM.

As used herein, the term ML 347 refers to 5-[6-(4-Methoxyphenyl)pyrazolo[1,5-a]pyrimidin-3-yl]quinoline. An effective concentration of ML 347 can be 2 nM-40 μM.

As used herein, the term UK 383367 refers to 3-(Aminocarbonyl)-β-(3-cyclohexylpropyl)-N-hydroxy-1,2,4-oxadiazole-5-propanamide. An effective concentration of UK 383367 can be 2 nM-40 μM.

As used herein, the term K 02288 refers to 3-[(6-Amino-5-(3,4,5-trimethoxyphenyl)-3-pyridinyl]phenol. An effective concentration of K 02288 can be 2 nM-40 μM.

As used herein, the term "Dorsomorphin" refers to 6-[4-[2-(1-Piperidinyl)ethoxy]phenyl]-3-(4-pyridinyl)-pyrazolo [1,5-a]pyrimidine dihydrochloride. An effective concentration of Dorsomorphin can be about 2 nM-100 μM.

As used herein, the term "Noggin" refers to protein Noggin. An effective concentration of Noggin can be about 1 ng/mL-100 μg/mL.

As used herein, the term "Chordin" refers to protein Chordin. An effective concentration of Chordin can be about 1 ng/mL-100 μg/mL.

As used herein, the term "Follistatin" refers to glycoprotein Follistatin. An effective concentration of Follistatin can be about 1 ng/mL-100 μg/mL.

As used herein, the term "Gremlin" refers to protein Gremlin. An effective concentration of Gremlin can be about 1 ng/mL-100 μg/mL.

As used herein, the term "PDGF-AA" refers to protein Platelet-Derived Growth Factor-AA protein. An effective concentration of PDGF-AA can be about 1 ng/mL-20 μg/mL.

As used herein, the term "PDGF-AB" refers to protein Platelet-Derived Growth Factor-AB protein. An effective concentration of PDGF-AB can be about 1 ng/mL-20 μg/mL.

As used herein, the term "PDGF-BB" refers to protein Platelet-Derived Growth Factor-BB protein. An effective concentration of PDGF-BB can be about 1 ng/mL-20 μg/mL As used herein, the term "Jagged 1 protein" refers to Jagged 1 protein ligand able to activate Notch receptors. An effective concentration of Jagged 1 protein can be about 1 ng/mL-1000 ng/mL.

As used herein, the term "Jagged 2 protein" refers to Jagged 2 protein ligand able to activate Notch receptors. An effective concentration of Jagged 2 protein can be about 1 ng/mL-800 ng/mL.

As used herein, the term "Delta-Like protein 1 (DLL1)" refers to Delta Like 1 protein ligand able to activate Notch receptors. An effective concentration of Jagged 1 protein can be about 1 ng/mL-1000 ng/mL.

As used herein, the term "Delta-Like protein 2 (DLL2)" refers to Delta Like 2 protein ligand able to activate notch receptors. An effective concentration of Jagged 1 protein can be about 1 ng/mL-1000 ng/mL.

As used herein, the term "Delta-Like protein 3 (DLL3)" refers to Delta Like 3 protein ligand able to activate notch receptors. An effective concentration of Jagged 1 protein can be about 1 ng/mL-800 ng/mL.

As used herein, the term "Oncostatin M" refers to Oncostatin M a pleiotropic cytokine that belongs to the interleukin 6 family of cytokines. An effective concentration of Oncostatin M protein can be about 1 ng/mL-1000 ng/mL.

As used herein, the term "Ciliary-Derived Neurotrophic Factor protein" refers to Ciliary-Derived Neurotrophic Factor protein (CNTF) which is a polypeptide hormone and neurotrophic factor. An effective concentration of Ciliary-Derived Neurotrophic Factor protein (CNTF) can be about 1 ng/mL-800 ng/mL.

As used herein, the term "Leukemia-Inhibitory Factor protein" refers to Leukemia inhibitory factor, or LIF, an interleukin 6 family cytokine. An effective concentration of Leukemia-Inhibitory Factor protein can be about 1 ng/mL-1000 ng/mL.

As used herein, the term "triiodothyronine" refers to is a thyroid hormone. Triiodothyronine plays an important role in the body's control of metabolism. An effective concentration of triiodothyronine can be about 1 ng/mL-1000 ng/mL.

As used herein, the term "phorbol ester" refers to any ester of phorbol, in which two hydroxyl groups on neighboring carbon atoms are esterified to fatty acids. Phorbol and phorbol esters are members of the tigliane family of diterpenes that are defined by polycyclic compounds. An effective concentration of phorbol ester can be about 1 nM-1000 nM.

As used herein, the term "forskolin" refers to a cell-permeable diterpene that directly activates adenylyl cyclase ($IC_{50}$=41 nM), the enzyme that produces cyclic adenosine monophosphate (cAMP), which as a result raises cAMP levels in the cell. An effective concentration of forskolin can be about 1 μM-200 μM.

As used herein, the term "neuregulin-1" refers to proteins or peptides that can bind and activate ErbB2, ErbB3, ErbB4 or combinations thereof, including but not limited to all neuregulin isoforms, neuregulin EGF domain alone, polypeptide comprising neuregulin EGF-like domain, neuregulin mutants or derivatives, and any kind of neuregulin-like gene products that also activate the above receptors as described in detail below. Neuregulin also includes NRG-1, NRG-2, NRG-3 and NRG-4 proteins, peptides, fragments and compounds that mimic the activities of neuregulin. An effective concentration of neuregulin-1 can be about 1 ng/mL-1000 ng/mL.

As used herein, the term "ascorbic acid" is the name recognized by the IUPAC-IUB Commission on Biochemical Nomenclature for Vitamin C. Other names are L-ascorbic acid, L-xyloascorbic acid and L-threo-hex-2-enoic acid y lactone. The pure vitamin is $C_6H_8O_6$ and has molecular weight 176.13. Four stereoisomers of ascorbic acid are possible: L-ascorbic acid, D-araboascorbic acid (erythorbic acid), which shows vitamin C activity, L-araboascorbic acid, and D-xyloascorbic acid. Ascorbic acid intermediates or "pathway intermediates" are those biochemicals capable of being converted to ASA via enzymatic or chemical means and include, but are not limited to, gluconic acid, 2-keto-D-gluconic acid, 2,5-diketo-D-gluconic acid, 2-keto-L-gulonic acid, idonic acid, gluconic acid, sorbitol, sorbose, sorbosone, and sorbose diacetone. An effective concentration of ascorbic acid can be about 1 μM-1000 μM.

Cells, Compositions and Kits

Some embodiments of the methods of cell production described in this disclosure involve, as a starting material or an intermediate, pluripotent or precursor cells or population of pluripotent or precursor cells or that are capable of selectively (and sometimes reversibly) developing into specified cellular lineages when cultured under appropriate conditions. As used herein, the term "population" refers to cell culture of more than one cell having the same identifying characteristics. The term "cell lineage" refers to all of the stages of the development of a cell type, from the earliest precursor cell to a completely mature cell (a specialized cell). One example of a precursor cell population that can be involved in the methods of cell production described in this disclosure is a culture of pluripotent stem cells (PSCs), which may be a culture embryonic stem cells (ESCs) and induced pluripotent stem cells (iPSCs). Some embodiments of the methods of cell production described in this disclosure involve human PSCs (hPSCs) or their populations as a starting material for deriving radial glia-like cells and astrocyte-like cells. It is to be understood that embodiments of the methods of cell production described in this disclosure can involve modified PSCs, including hPSCs. Some examples of PSCs that can be used in the methods according to the embodiments of the present invention are various ESCs (e.g., WA01, WA09, WA14 from WiCell) and iPSC lines (LiPSC-GR1.1, NORM-1, NCRM-2, NCRM-5, all available from National Institutes of Health (USA).

Another example of a precursor cell population that can be involved in the method of cell production described in this disclosure is a population of radial glia-like cells, which can be produced from PSCs according to some embodiments of the methods described in this disclosure. Radial glia-like cells, as discussed in this disclosure, are cells exhibiting at least some properties of radial glia cells occurring during vertebrate embryonic development. Radial glia-like cells according to the embodiments of the present invention can express at least one marker of naturally occurring radial glial cells—Brain Lipid Binding Protein (BLBP), CD133 (Prominin 1), ASPM, BIRC5 (Survivin), FAT1, HES5, SOX21 and PAX6. For example, radial glia-like cells involved in the methods according to the embodiments of the present invention can express at least one marker of naturally occurring radial glial cells—Brain Lipid Binding Protein (BLBP), CD133 (Prominin 1), ASPM, BIRC5 (Survivin), FAT1, HES5, SOX21. In another example, radial glia-like cells involved in the methods according to the embodiments of the present invention can express all of Brain Lipid Binding Protein (BLBP), CD133 (Prominin 1), ASPM, BIRC5 (Survivin), FAT1, HES5, SOX21 and PAX6.

As used herein, "astrocyte-like cells" is defined as a cell population expressing glial fibrillary acidic protein (GFAP) which is differentiated from embryonic stem cells. Astrocyte-like cells are cells comprising at least one astrocytic phenotype which allows same to in vivo mediate an astrocytic activity, i.e., support of neurons.

As used herein, the phrase "astrocytic phenotype" refers to a structural and/or functional parameter typical (e.g., unique) to an astrocyte. The astrocytic phenotype may comprise a single or a number of features. Examples of structural astrocytic phenotypes include a cell size, a cell shape, an organelle size and an organelle number. Thus, astrocytic structural phenotypes may include a round nucleus, a "star shaped' body and expression of an astrocyte marker.

As used herein the phrase "astrocyte marker" refers to a polypeptide which is either selectively or non-selectively expressed in an astrocyte. The astrocyte marker may be expressed on the cell surface or internally. Examples of astrocyte markers include S100 beta, glial fibrillary acidic protein (GFAP), glutamine sythetase, GLAST and GLT1.

As discussed throughout the present disclosure, some embodiments of the methods of the present invention produce astrocyte-like cells or their populations. Astrocyte-like cells, as discussed in this disclosure, are cells exhibiting some properties of naturally occurring astrocyte cells. Astrocyte-like cells according to the embodiments of the present invention can express one or more markers expressed by naturally occurring astrocytes, such as S100 Calcium-Binding Protein B (S100B), Nuclear Factor 1 A-Type Protein (NFIA), CD44, HEPACAM, Glial Fibrillary Acidic Protein (GFAP) or vimentin. In one example, astrocyte-like cells according to the embodiments of the present invention can express all of S100 Calcium-Binding Protein B (S100B), Nuclear Factor 1 A-Type Protein (NFIA), CD44 protein, HEPACAM, Glial Fibrillary Acidic Protein (GFAP) or vimentin. Astrocyte-like cells according to the embodiments of the present invention can exhibit flat and/or star-shaped morphology. In one example, astrocyte-like cells according to the embodiments of the present invention can exhibit flat and/or star-shaped morphology and express all of S100 Calcium-Binding Protein B (S100B), Nuclear Factor 1 A-Type Protein (NFIA), CD44 protein, HEPACAM, Glial Fibrillary Acidic Protein (GFAP) or vimentin (VIM).

The presence or absence of the markers, as applied to the embodiments of the preset invention, means detectable presence or absence of the markers as detected by applicable methods for detecting such markers, and may mean certain detectable or undetectable levels of such markers. In other words, the presence may mean the presence above a certain detectable level, while the absence may mean the absence below a certain detectable level and not necessarily zero detectable level. It is also to be understood that astrocyte-like cells may include a variety of cells on a continuum, with varying levels of presence or absence of certain detectable markers.

Compositions according to the embodiments of the present invention include in vitro or ex vivo compositions comprising at least one radial glia-like cell or at least one astrocyte-like cells. The cells included in such compositions can be vertebrate cells (meaning the cells originating from vertebrate PSCs), including mammalian cells (meaning the cells generated from mammalian PSCs) or human cells (meaning the cells generated from mammalian PSCs). The cells included in such compositions can be modified cells. The compositions can include pluralities of cells of the same or different type. For example, a plurality of cells can include one or more of a pluripotent stem cell, a multipotent stem cell, a progenitor cell, a differentiated cell, and a modified cell. A plurality of mammalian cells can be multiple cells, a cell culture, a cell aggregate, a spheroid or a tissue. At least one cell or a plurality of cells can be cryopreserved or thawed after cryopreservation. It is understood that some of the compositions according embodiments of the present invention can further comprise a culture medium, one or more additives, a vessel containing the culture medium, such as a culture flask, a culture dish, a tube or a reactor, and can also comprise a support or a scaffold for cells.

Using the described methods, compositions comprising various mixtures of pluripotent stem cells and other multipotent or differentiated cells can be produced. Such compositions are included among the embodiments of the present invention. In some embodiments, compositions comprising at least about 5 multipotent or differentiated cells for about every 95 pluripotent cells can be produced. In other embodiments, compositions comprising at least about 95 multipotent or differentiated cells for about every 5 pluripotent cells can be produced. Additionally, compositions comprising other ratios of multipotent or differentiated cells to pluripotent cells are contemplated. For example, compositions comprising at least about 1 multipotent or differentiated cell for about every 1,000,000 pluripotent cells, at least about 1 multipotent or differentiated cell for about every 100,000 pluripotent cells, at least about 1 multipotent or differentiated cell for about every 10,000 pluripotent cells, at least about 1 multipotent or differentiated cell for about every 1000 pluripotent cells, at least about 1 multipotent or differentiated cell for about every 500 pluripotent cells, at least about 1 multipotent or differentiated cell for about every 100 pluripotent cells, at least about 1 multipotent or differentiated cell for about every 10 pluripotent cells, at least about 1 multipotent or differentiated cell for about every 5 pluripotent cells, and up to about every 1 pluripotent cell and at least about 1,000,000 multipotent or differentiated cell for about every 1 pluripotent cell are contemplated. Some embodiments of the compositions can be cell cultures or cell populations comprising from at least about 5% multipotent or differentiated cell to at least about 99% multipotent or differentiated cells. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 99% of the human cells are multipotent or differentiated cell. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or greater than 99% of the human cells are multipotent or differentiated cells.

The progression of pluripotent cells to multipotent cells to further differentiated cells (for example, a progression from PSCs to radial glia-like cells, or a progression of radial glia-like cells to astrocyte-like cells) can be monitored by detecting the markers characteristic of the specific cell type. Identification of cell types related to the embodiments of the present invention can also be performed by detecting the markers characteristic of the specific cell type. For example, expression of certain markers can be detected. Expression of certain markers can be determined by detecting the presence or absence of the marker in cells, cell culture or cell population. Expression of certain markers can also be determined by measuring the level at which the marker is present in cells, cell culture or cell population. In some embodiments of the present invention, the expression of one or markers characteristic of radial glia-like cells, such as BLBP, CD133 (Prominin 1), ASPM, BIRC5 (Survivin), FAT1, HESS, SOX21 or PAX6, can be determined. In some embodiments, the expression of one or more markers characteristic of astrocyte-like cells, such as S100B, NFIA, CD44, HEPACAM, GFAP or vimentin, can be determined. Quantitative, qualitative or semi-quantitative techniques can be used to measure marker expression. For example, marker expression can be detected and/or quantitated through the use of techniques detecting nucleic acids, such as PCR-based detection or RNA (for example, real-time reverse-transcriptase PCR), RNA sequencing (RNA-seq), or RNA detection by nucleic acid array-based techniques. In another example, immunochemistry can be used to detect and/or quantitate marker proteins. For example, the expression of a marker gene product can be detected by using antibodies specific for the marker gene product of interest using Western blotting, immunocytochemical characterization, flow cytometry analysis, etc. Various techniques of marker detection can be used in in conjunction to effectively and accurately characterize and identify cell types and determine both the amount and relative proportions of such markers in a subject cell type. The expression of certain markers can be determined by measuring the level at which the marker is present in the cells of the cell culture or cell population as compared to a standardized or normalized control marker. Identification and characterization of cells, cell cultures or cell population can be based on expression of a certain marker or different expression levels and patterns of more than one marker (including the presence or absence, the high or low expression, of one or more the markers). Also, certain markers can have transient expression, when the marker is exhibits higher expression during one or more stages of the processes described in this disclosure and lower expression during other stage or stages.

Kits for cell, tissue or organ culture are included among embodiments of the present invention. A kit is a set of components, comprising at least some components for culturing cells, which can include single cells and groups of cells. A kit can contain one or more additives discussed in the corresponding section of this disclosure. A kit may further contain one or more of the following: culture media configured to support at least one cell in vitro or ex vivo or one or more of culture media components; a vessel for holding the culture medium; a culture vessel, such as a flask, a dish, a plate (including a multi-well plater) or a reactor; or a support or scaffold for cell or tissue culture. A kit may contain one or more mammalian cells, such as human cells. Cells included in the kit can be one or more of: PSCs (including embryonic stem cells and/or induced pluripotent stem cells), radial glia-like cells or astrocyte-like cells. One or more cells can be provided in a frozen or non-frozen form (which can be a thawed form).

Cryopreservation

Methods, compositions and kits that involve cryopreservation, including processes, tools and/or compositions related to cryopreservation, thawing and culturing of previously cryopreserved cells, cell populations or cell cultures are included among the embodiments of the present invention. Some compositions related to the preservation can include a cryopreservation medium used for the cryopreservation of cells or cell populations described in this disclosure, such as radial glia-like cells and astrocyte-like cells.

Some compositions can include a cryopreservation medium and one or more cells described in this disclosure. For example, an embodiment of a composition can include one or more radial glia-like cells and a cryopreservation medium. In another example, a composition can include one or more astrocyte-like cells and a cryopreservation medium. The cryopreservation medium can be a liquid medium in which the cells are found prior to freezing and/or while in frozen state. Some examples of cryopreservation media are PSC Cryopreservation Kit (Thermo Fisher Scientific), FreezIS (Irving Scientific), NutriFreez (Biological Industries USA), CryoStor, HypoThermosol, mFreSR, mFreSR-S, STEMdiff Neural Progenitor Freezing Medium (all from Stem Cell Technologies). Cryopreservation medium can contain one or more cryoprotectants, meaning compounds protecting cells from freezing damage. Cryoprotectants can be permeating or non-permeating. An example of a suitable permeating cryoprotectant, which is able to permeate cell membranes, is dimethyl sulfoxide (DMSO). Some examples of suitable non-permeating cryoprotectants are sucrose, glycerol, dextran, trehalose, percoll, polyethylene glycol, polyvinyl pyrrolidone, serum albumin, ficol, maltose and polyvinylalcohol (PVA). The cryopreservation medium can further contain one or more additives described in the section "Additives" of this disclosure. For example, the cryopreservation medium can comprise one or more of Chroman-1 or its derivatives, Emricasan or its derivatives, trans-ISRIB or polyamines, at their respective effective combination. A combination of all four of the above additives can be referred to as "CEPT."

Methods involving cryopreservation of cells, cell populations or cell cultures are included among the embodiments of the present invention. Such methods may include a step of contacting one or more cells, such as radial glia-like cells or astrocyte-like cells with a cryopreservation medium. This may involve adding the cryopreservation medium to the one or more cells, or vice versa, and mixing the cells with the medium. In some embodiments, between 0.5 mL and 5 mL of cryopreservation medium may be added per one million cells, for example about 1 mL per million cells. However, it is envisaged that in certain embodiments, higher or lower amounts of cryopreservation medium can be used. In some embodiments, the cryopreservation medium may be added to the cells in step-wise increments of increasing concentration, which may reduce the risk of cellular osmotic shock associated with single-step addition. The temperature of the cryopreservation medium when added to the cells may range from about 15° C. to about 40° C. For example, the temperature of the cryopreservation medium added to the cells can be about 37° C. The contacting step of the present method may result in suspension of the cells in the cryopreservation medium, which can be referred to as "mixture." The cells before the contacting step or the cell suspension after the contacting step may be provided in a container or a vessel. A container may have a volume between 1 mL and 50 mL, for example, it may be a tube of 15 mL.

Methods involving cryopreservation of cells may include a step of freezing a composition comprising one or more cells, such as radial glia-like cells or astrocyte-like cells, and a cryopreservation medium, thereby obtaining a frozen or cryopreserved composition. A mixture of the cells and the cryopreservation medium can be equilibrated prior to freezing the mixture. During equilibration, water can be removed from the cells and replaced by the medium comprising the cryoprotectant, which enters into the cells after incubation of the cells with the cryopreservation medium. The equilibration time is limited to avoid damage to the cells. For example, the mixture can be equilibrated for a time period of between 10 seconds and 5 minutes, between 20 seconds and 1.5 minutes, or between 30 seconds to 1 minute. Before freezing, the mixture can be transferred to a freezing container or vessel, or remain in the same container in which the mixture already resided. Water can be removed from the cells and replaced by the medium comprising the cryoprotectant, which enters into the cells after incubation of the cells with the cryopreservation medium. The containers used for freezing typically provide for the stacking of tubes and can ensure that, by placing the container in a freezer, a fixed rate of cooling is achieved.

The freezing results in the cells in a cryogenic or cryopreserved state (which may simply be described as "frozen"), in which they can remain for periods of days, weeks, months or years, for retrieval when the cells are required. When needed, the cryopreserved cells are retrieved and thawed. Accordingly, methods involving cryopreservation can include a step of thawing a cryopreserved composition, more particularly under conditions that maintain cell viability. For example, a container containing the cryopreserved cells can be thawed in a bath of water, at a temperature of 42° C. or less, such as between 10° C. and 40° C., for example, at about 37° C. To improve the post-thaw cell viability, a thawing rate between about 10° C. and about 40° C. per minute, such as about 20° C. and about 40° C. per minute, for example, approximately 30° C. per minute may be used.

The described methods and/or method steps may lead to good viability of cryopreserved cells after thawing. As used herein, the term "viability" refers to the number of living cells based on the presence of DNA and an intact cell membrane system. Viability can be measured by various tests, such as a Trypan blue internalization test or by measuring propidium iodide uptake. The viability of the thawed cells after cryopreservation, such as thawed radial glia-like cells or thawed astrocyte cells can be at least 50%, at least 55%, at least 60%, at least 65%, at least 70%, at least 75%, at least 80%, at least 85%, at least 90%, or at least 95%. The cells may display a limited amount of necrosis and apoptosis after thawing. In particular embodiments, necrosis and/or apoptosis is observed in less than 25% of the cells, more particularly less than 15%, most particularly less than 10% of the cells. The methods described herein may further ensure that radial glia-like cells maintain their ability to differentiate into astrocyte-like cells. After thawing, the cryopreserved cells may be used for further culturing, differentiation (in the case of radial glia-like cells), therapeutic purposes, such as regenerative medicine, or other uses.

Exemplary embodiments of the present invention include methods of producing in culture radial glia-like cells. For example, in some of the embodiments disclosed herein are the methods of producing, in culture, radial glia-like cells, the method comprising:

(a) plating vertebrate pluripotent stem cells on a substrate-coated surface of a culture vessel at a density of 1,000-100,000 cells/$cm^2$;

(b) incubating the plated vertebrate pluripotent stem cells in a first culture medium;

(c) replacing the first culture medium with a second culture medium comprising:

(i) an effective amount or concentration of one or more inhibitors of BM P pathway, (ii) an effective amount or concentration of one or more activators of Notch pathway, (iii) one or more cytokines of interleukin-6 family; and (d) culturing the plated vertebrate pluripotent stem cells in the second culture medium;

thereby producing radial glia-like cells.

Some methods of producing in culture radial glia-like cells according to the embodiments of the present invention comprise a step of culturing vertebrate pluripotent stem cells in a second culture medium comprising an effective amount or concentration of one or more inhibitors of the BMP pathway, an effective amount or concentration of one or more activators of Notch pathway, an effective amount or concentration of one or more cytokines of interleukin-6 family, and an effective amount or concentration of one or more Platelet-Derived Growth Factor protein; and, culturing the plated vertebrate pluripotent stem cells in the second culture medium for approximately 168-360 hours, thereby generating radial glia-like cells. The vertebrate pluripotent stem cells can be induced pluripotent stem cells or embryonic pluripotent stem cells. The vertebrate pluripotent stem cells can be human pluripotent stem cells.

In some embodiments of the methods disclosed herein, the substrate comprises vitronectin, laminin 521, Matrigel, and/or Geltrex.

In some embodiments of the methods disclosed herein, plating vertebrate pluripotent stem cells, comprises plating at the cell density of 2,000-90,000 cells/$cm^2$; 3,000-80,000 cells/$cm^2$; 4,000-70,000 cells/$cm^2$; 5,000-50,000 cells/$cm^2$, and/or 10,000-30,000 cells/$cm^2$.

In some embodiments of the methods disclosed herein, incubating the plated vertebrate pluripotent stem cells in the first culture medium comprises incubating for 12-48 hours.

In some embodiments of the methods disclosed herein, culturing the plated vertebrate pluripotent stem cells in the second culture medium comprises culturing for at least 5-20 days.

In some embodiments of the methods disclosed herein, the first culture medium is a first defined culture medium, wherein the first defined culture medium is E8, E8 Flex, StemFlex, mTeSR, StemFit, or mouse embryonic fibroblast (MEF)-conditioned medium. In some embodiments of the methods disclosed herein, the first culture medium comprises an effective concentration of Chroman 1 or a derivative thereof, an effective concentration of Emricasan or a derivative thereof, an effective concentration of trans-ISRIB, and an effective concentration of polyamines comprising putrescine, spermine, and spermidine. In some embodiments of the methods disclosed herein, the effective concentration of Chroman 1 or the derivative thereof is about 4 nM to about 80 μM, the effective concentration of Emricasan or the derivative thereof is about 100 nM to about 80 μM, the effective concentration of trans-ISRIB is about 50 nM to about 80 μM, and wherein putrescine, spermine, and spermidine is each at a concentration of about 0.5 nM to 1 mM. In some embodiments of the methods disclosed herein, the first culture medium further comprises at least one inhibitor of Rho-associated protein kinase (ROCK). In some embodiments of the methods disclosed herein, the one or more ROCK inhibitors comprise one or more of Chroman 1 or a derivative thereof, Y27632, blebbistatin, or thiazovivin.

In some embodiments of the methods disclosed herein, during the culturing in the second culture medium, the cells being cultured detectably express one or more radial glia cell markers at approximately 4-10 days after start of the culturing in the second culture medium. In some embodiments of the methods disclosed herein, for example, the radial glia-like cells detectably express one or more of Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HES5), SRY-Box Transcription Factor 21 (SOX21), and PAX6 protein. Radial glia-like cells are multipotent stem cells capable of differentiating into neuron-like cells, oligodendrocyte-like cells, and/or astrocyte-like cells. In some embodiments of the methods disclosed herein, during the culturing in the second culture medium, the cells being cultured detectably express one or more astrocyte markers at approximately 5-20 days after start of the culturing. In some embodiments of the methods disclosed herein, the one or more astrocyte markers comprise S100 Calcium-Binding Protein B (S100B). In some embodiments of the methods disclosed herein, during the culturing in the second culture medium, cells being cultured detectably express one or more neural stem cell markers at approximately 2-10 days after start of the culturing. In some embodiments of the methods disclosed herein, the one or more neural stem cell markers can comprise PAX6.

In some embodiments of the methods disclosed herein, the radial glia-like cells are multipotent stem cells capable of differentiating into neuron-like cells, oligodendrocyte-like cells, and/or astrocyte-like cells.

In some embodiments of the methods disclosed herein, the vertebrate pluripotent stem cells are induced pluripotent stem cells or embryonic pluripotent stem cells. In some embodiments of the methods disclosed herein, the vertebrate pluripotent stem cells are human pluripotent stem cells.

In some embodiments of the methods disclosed herein, the second culture medium can be a second defined culture medium, for example, but not limited to, DMEM-F12, E6, Neurobasal medium, or minimal essential medium (MEM). In some embodiments of the methods disclosed herein, the second defined culture medium can comprise N2 supplement and/or B27 supplement without vitamin A. In some embodiments of the methods disclosed herein, the one or more inhibitors of the BMP pathway included in the second culture medium can comprise one or more of LDN-193189, LDN-214117, LDN-212854, DMH2, ML 347, UK 383367, K 02288, Dorsomorphin, Noggin, Chordin, Follistatin, or Gremlin. For example, in some embodiments of the methods disclosed herein, the effective amount or concentration of the one or more inhibitors of the BMP pathway can comprise 2 nM-40 μM LDN-193189. In some embodiments of the methods disclosed herein, the second culture medium further comprises an effective amount or concentration of one or more Platelet-Derived Growth Factor protein. In some embodiments of the methods disclosed herein, the one or more Platelet-Derived Growth Factor protein included in the second culture medium can be Platelet-Derived Growth Factor-AA (PDGF-AA), Platelet-Derived Growth Factor-BB (PDGF-BB), or Platelet-Derived Growth Factor-AB (PDGF-AB). In some embodiments of the methods disclosed herein, the effective amount or concentration of the one or more Platelet-Derived Growth Factor protein is about 1 ng/mL-800 ng/mL. In some embodiments of the methods disclosed herein, the effective amount or concentration of the one or more activators of Notch pathway included in the second culture medium can comprise one or more of Jagged 1 protein, Jagged 2 protein, and Delta-Like protein 1 (DLL1), Delta-Like protein 2 (DLL2), or Delta-Like protein 3 (DLL3). For example, in some embodiments of the methods disclosed herein, the one or more activators of Notch pathway in the second culture medium comprise one or both of 1 ng/mL-800 ng/mL Jagged 1 protein and 1 ng/mL-800 ng/mL Delta-Like protein 1 (DLL1). In some embodiments of the methods disclosed herein, the one or more cytokines of interleukin-6 family in the second culture medium comprise one or more of Oncostatin M protein, Ciliary-Derived Neurotrophic Factor protein (CNTF) and Leukemia-Inhibitory Factor protein (LIF). For example, in some embodiments of the methods disclosed herein, each of the one or more Oncostatin M protein, Ciliary-Derived Neurotrophic Factor protein (CNTF) and Leukemia-Inhibitory Factor protein (LIF) is present in the second culture medium in a concentration of 1 ng/mL-800 ng/mL. In some embodiments of the methods described in the present disclosure, the second culture medium can comprise an effective concentration of Chroman 1 or a derivative thereof, an effective concentration of Emricasan or a derivative thereof, an effective concentration of trans-ISRIB and an effective concentration of polyamines comprising putrescine, spermine and spermidine. In some embodiments of the methods disclosed herein, an effective concentration of Chroman 1 or the derivative thereof can be about 4 nM to about 80 μM, the effective concentration of Emricasan or the derivative thereof can be about 100 nM to about 80 μM, the effective concentration of trans-ISRIB can be about 50 nM to about 80 μM, and each of putrescine, spermine and spermidine can be present at a concentration of about 0.5 nM to 1 mM. In some embodiments of the methods disclosed herein, the step of culturing in the second culture medium can comprise changing the second culture medium approximately every 20-28 hours. In some embodiments of the methods disclosed herein, the step of culturing in the second culture medium can comprise one or more steps of passaging cells being cultured when they become confluent. For example, in some embodiments of the methods disclosed herein, the one or more steps of passaging can be performed at 1:3 to 1:5 ratio of confluent cell culture to fresh medium. The step of culturing in the second culture medium can comprise 3-7 of the passaging steps.

Exemplary embodiments of the present invention include methods of producing in culture of the astrocyte-like cells from the radial glia-like cells produced according to the methods according to the embodiments of the instant invention.

In one embodiment, a method of producing in culture of the astrocyte-like cells include, performing at least one of the methods disclosed herein and, after the step of generating the radial glia-like cells, culturing the radial glia-like cells for approximately 5-30 days in a third culture medium, an effective amount or concentration of one or more activators of Notch pathway, and an effective amount or concentration of one or more cytokines of Interleukin-6 (IL-6) family, thereby generating the culture of the astrocyte-like cells. In some embodiments of the methods disclosed herein, the third culture medium can be a third defined culture medium, such as, but not limited to, DMEM-F12, Neurobasal medium, minimal essential medium (MEM), or BrainPhys neuronal medium. In some embodiments of the methods disclosed herein, the third defined culture medium can comprise N2 supplement and/or complete B27 supplement.

In some embodiments of the methods disclosed herein, the one or more activators of Notch pathway included in the third culture medium can comprise one or more of Jagged 1 protein, Jagged 2 protein, and Delta-Like protein 1 (DLL1), Delta-Like protein 2 (DLL2), or Delta-Like protein31 (DLL3). For example, in some embodiments of the methods disclosed herein, the effective amount or concentration of the one or more activators of Notch pathway in the third culture medium can comprise one or both of 1 ng/mL-800 ng/mL Jagged 1 protein and 1 ng/mL-800 ng/mL Delta-Like protein 1 (DLL1). In some embodiments of the methods disclosed herein, the one or more cytokines of interleukin-6 family in the third culture medium comprise one or more of Oncostatin M protein, Ciliary-Derived Neurotrophic Factor protein (CNTF) and Leukemia-Inhibitory Factor protein (LIF). For example, in some embodiments of the methods disclosed herein, the effective amount or concentration of each of Oncostatin M protein, Ciliary-Derived Neurotrophic Factor (CNTF) protein and Leukemia-Inhibitory Factor (LIF) protein can be present in the third culture medium in a concentration of 1-800 ng/mL.

In some embodiments of the methods disclosed herein, the third culture medium can comprise an effective concentration of Chroman 1 or a derivative thereof, an effective concentration of Emricasan or a derivative thereof, an effective concentration of trans-ISRIB and an effective concentration of polyamines comprising putrescine, spermine and spermidine. In some embodiments of the methods disclosed herein, an effective concentration of Chroman 1 or the derivative thereof can be about 4 nM to about 80 μM, the effective concentration of Emricasan or the derivative thereof can be about 100 nM to about 80 μM, the effective concentration of trans-ISRIB can be about 50 nM to about 80 μM, and each of putrescine, spermine and spermidine can be present at a concentration of about 0.5 nM to 1 mM. In some embodiments of the methods disclosed herein, the step of culturing in the third culture medium can comprise changing the third culture medium approximately every 24-72 hours. In some embodiments of the methods disclosed herein, the step of culturing in the third culture medium can comprise one or more steps of passaging cells being cultured when they become confluent. In some embodiments of the methods disclosed herein, the one or more passaging steps can be performed at 1:2 ratio of confluent cell culture to fresh medium. In some embodiments of the methods disclosed herein, the step of culturing in the third culture medium can comprise 1-3 passaging steps. In some embodiments of the methods disclosed herein, during the step of culturing in a third culture medium detectable neuron-like cells are present at 10% or less of total cells in culture.

In some embodiments of the methods disclosed herein, the entire astrocyte differentiation procedure was executed as monolayer. In some embodiments, the entire astrocyte differentiation procedure was executed to include a sphere formation stage. During these procedures, the sphere formation step at Day 14 helped to mature cells and reduces cell passaging steps. Specifically, single cell dissociation was performed at day 14 and cells were maintained for 24 h in Astro-2 medium with CEPT in suspension to form spheres (100.000 cells/well of the 96-well plate with U bottom). One day later, spheres were then transferred to a vessel with low-cell attachment surface in Astro-2 medium. Media change was performed every other day. After one week in Astro-2 medium, Astro-3 containing DMEM/F12 media supplemented with N2 B27 complete, chemically defined lipid concentrate (2%), LIF (10 ng/ml), and CNTF (10 ng/ml) or enriched Astro-3 medium were introduced. In some embodiments of the methods disclosed herein, the enriched Astro-3 contained DMEM/F12 media supplemented with N2 B27 complete, chemically defined lipid concentrate (2%), LIF (10 ng/ml), and CNTF (10 ng/ml), Jagged 1 (10 ng/ml), DLL-1 (10 ng/ml), triiodothyronine (also known as T3 is a thyroid hormone) (40 ng/ml), phorbol ester (200 nM), forskolin 2 μM, neuregulin-1 (20 ng/ml), and ascorbic acid (200 μM). Spheres were cultured in Astro-3 or enriched Astro-3 medium for another week with media change every other day. At day 28, spheres were single-cell dissociated by Accutase treatment and astrocytes were maintained as monolayer culture in Astro-3 or enriched Astro-3 media until day 50.

The astrocyte-like cells produced by the methods according to the embodiments of the present invention detectably express one or more of astrocyte markers. In some embodiments of the methods disclosed herein, the one or more astrocyte markers can comprise S100 Calcium-Binding Protein B (S100B), Nuclear Factor 1 A-Type Protein (NFIA), Glial Fibrillary Acidic Protein (GFAP) and vimentin (VIM). In some embodiments of the methods disclosed herein, the astrocyte-like cells produced by the methods according to the embodiments of the present invention can exhibit flat and/or star-shaped.

In some embodiments of the methods disclosed herein, the third culture medium further comprises a chemically defined lipid concentrate at a concentration of approximately 2%, comprising one or more of arachidonic acid, cholesterol, DL-alpha-tocopherol acetate, linoleic acid, linolenic acid, myristic acid, oleic acid, palmitic acid, palmitoleic acid, and stearic acid or fetal bovine serum at a concentration of approximately 2%.

As discussed throughout the present disclosure, some embodiments of the methods of the present invention produce astrocyte-like cells exhibiting star-shaped and/or sphere morphology. For example, in another embodiment of the present invention are exemplary methods of culturing the astrocyte-like cells, which comprise performing at least one of the methods disclosed herein, and further culturing the astrocyte-like cells in a fourth culture medium and an effective amount or concentration of one or more cytokines of interleukin-6 family, thereby enhancing maturation of astrocyte-like cells. In some embodiments of the methods disclosed herein, the fourth culture medium can be a fourth defined culture medium, such as, but not limited to, DMEM-F12, E6, Neurobasal medium, or minimal essential medium (MEM). In some embodiments of the methods disclosed herein, the fourth defined culture medium can comprise N2 supplement and/or B27 supplement. In some embodiments of the methods disclosed herein, the one or more cytokines of interleukin-6 family comprise one or both of Ciliary-Derived Neurotrophic Factor protein (CNTF) and Leukemia-Inhibitory Factor protein (LIF). For example, in some embodiments of the methods disclosed herein, the effective amount of concentration of each of the one or both of Ciliary-Derived Neurotrophic Factor protein (CNTF) and Leukemia-Inhibitory Factor protein (LIF) is present in a concentration of 1-800 ng/mL. In some embodiments of the methods disclosed herein, the fourth medium optionally is an enriched fourth defined culture medium, comprising an effective amount or concentration of one or more activators of Notch pathway and/or one or more thyroid hormone, phorbol ester, forskolin, neuregulin, and ascorbic acid. In some embodiments of the methods disclosed herein, the thyroid hormone is triiodothyronine and the one or more activators of Notch pathway in the fourth culture medium comprise one or more of Jagged 1 protein and Delta-Like protein 1 (DLL1). In some embodiments of the methods disclosed herein, the one or more activators of Notch pathway is about 1 ng/mL to about 800 ng/mL Jagged 1 protein and 1 ng/mL to about 800 ng/mL Delta-Like protein 1 (DLL1), and the concentration of thyroid hormone is about 1 ng/Ml to about 1000 ng/mL, the concentration of phorbol ester is about 1 nM to about 1000 nM, the concentration of forskoline is about 1 μM to about 200 μM, the concentration of neuregulin is about 1 ng/mL to about 1000 ng/mL, and the concentration of ascorbic acid is about 1 μM to about 1000 μM.

In some embodiments of the methods disclosed herein, the fourth culture medium can comprise an effective concentration of Chroman 1 or a derivative thereof, an effective concentration of Emricasan or a derivative thereof, an effective concentration of trans-ISRIB and an effective concentration of polyamines comprising putrescine, spermine and spermidine. In some embodiments of the methods disclosed herein, an effective concentration of Chroman 1 or the derivative thereof can be about 4 nM to about 80 μM, the effective concentration of Emricasan or the derivative thereof can be about 100 nM to about 80 μM, the effective concentration of trans-ISRIB can be about 50 nM to about 80 μM, and each of putrescine, spermine and spermidine can be present at a concentration of about 0.5 nM to 1 mM. In some embodiments of the methods disclosed herein, the culturing in the fourth culture medium is performed for at least approximately 40-60 hours. In some embodiments of the methods disclosed herein, the step of culturing in the fourth culture medium can comprise changing the fourth culture medium approximately every 24-96 hours. In some embodiments of the methods disclosed herein, during the culturing in the fourth culture medium the astrocyte-like cells detectably express one or more of Hepatic and Glial Cell Adhesion Molecule (HEPACAM), glial fibrillary acidic protein (GFAP), CD44 protein, and vimentin (VIM). As discussed above, during the culturing in the fourth culture medium the astrocyte-like cells exhibit star-shaped morphology and/or sphere morphology.

In some embodiments of the methods disclosed herein, one or more steps of the method are performed by an automated system. In some embodiments of the methods disclosed herein, the fourth culture medium further comprises a chemically defined lipid concentrate at a concentration of approximately 2%, comprising one or more of arachidonic acid, cholesterol, DL-alpha-tocopherol acetate, linoleic acid, linolenic acid, myristic acid, oleic acid, palmitic acid, palmitoleic acid, and stearic acid or fetal bovine serum at a concentration of approximately 2%.

In another embodiment, a composition comprising at least one cultured radial glia-like cell detectably expressing one or more of Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HESS), SRY-Box Transcription Factor 21 (SOX21), and PAX6 protein. In some embodiments of the compositions disclosed herein, at least one cultured radial glia-like cells or was cryopreserved, for example, in a cryopreservation medium comprising Chroman 1 and/or a derivative thereof, Emricasan and/or the derivative thereof, trans-ISRIB and polyamines comprising putrescine, spermine and spermidine. In some embodiments of the compositions disclosed herein, in the cryopreservation medium, Chroman 1 and/or the derivative thereof can be at a concentration of about 4 nM to about 80 μM, Emricasan and/or the derivative thereof can be at a concentration of about 100 nM to about 80 μM, trans-ISRIB can be at a concentration of about 50 nM to about 80 μM, and each of putrescine, spermine and spermidine can be at a concentration of about 0.5 μM to 1 mM.

In some embodiment of the compositions disclosed herein, composition, comprising at least one cultured radial glia-like cell detectably expressing at least one marker, wherein the at least one marker is Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HESS), SRY-Box Transcription Factor 21 (SOX21), or PAX6 protein. In some embodiment of the compositions disclosed herein, the at least one cultured radial glia-like cell is or was cryopreserved. In some embodiment of the compositions disclosed herein, the at least one cultured radial glia-like cell is or was cryopreserved in a cryopreservation medium comprising Chroman 1 and/or a derivative thereof, Emricasan and/or the derivative thereof, trans-ISRIB and polyamines comprising putrescine, spermine and spermidine. In some embodiment of the compositions disclosed herein, in the cryopreservation medium, Chroman 1 and/or the derivative thereof is or was at a concentration of about 4 nM to about 80 μM, wherein Emricasan and/or the derivative thereof is or was at a concentration of about 100 nM to about 80 μM, wherein trans-ISRIB is or was at a concentration of about 50 nM to about 80 μM, and wherein each of putrescine, spermine and spermidine is or was at a concentration of about 0.5 μM to 1 mM.

In another embodiment, a composition, comprising at least one cultured radial glia-like cell produced by the methods disclosed herein and expressing at least one marker, wherein the at least one marker is Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HESS), SRY-Box Transcription Factor 21 (SOX21), or PAX6 protein.

In another embodiment, a cell culture comprising at least one cultured radial glia-like cell detectably expressing at least one marker, wherein the at least one marker is Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HES5), SRY-Box Transcription Factor 21 (SOX21), and PAX6 protein. In some embodiments of the cell cultures disclosed herein, the cell culture can be grown from previously cryopreserved cells, for example, from the cells that were cryopreserved in a cryopreservation medium comprising Chroman 1 and/or a derivative thereof, Emricasan and/or the derivative thereof, trans-ISRIB and polyamines comprising putrescine, spermine and spermidine. In some embodiments of the cell cultures disclosed herein, the previously cryopreserved cells can be vertebrate pluripotent stem cells, such as induced pluripotent stem cells or embryonic pluripotent stem cells. In some embodiments of the cell cultures disclosed herein, the vertebrate pluripotent stem cells can be human pluripotent stem cells. In some embodiments of the cell cultures disclosed herein, the previously cryopreserved cells can also be cultured radial glia-like cells detectably expressing Brain Lipid Binding Protein (BLBP), Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HESS), SRY-Box Transcription Factor 21 (SOX21), and PAX6 protein.

In another embodiment, a cell culture, comprising at least one cultured radial glia-like cell produced by the methods disclosed herein and expressing at least one marker, wherein the at least one marker is Brain Lipid Binding Protein (BLBP), CD133 (Prominin 1), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HESS), SRY-Box Transcription Factor 21 (SOX21), or PAX6 protein.

In another embodiment, a composition, comprising at least one cultured astrocyte-like cell exhibiting flat, star-shaped, and/or sphere morphology and detectably expressing at least one marker, wherein the at least one marker is S100 Calcium-Binding Protein B (S100B), Nuclear Factor 1 A-Type Protein (NFIA), Hepatic and Glial Cell Adhesion Molecule (HEPACAM), glial fibrillary acidic protein (GFAP), CD44 protein, or vimentin (VIM). In some embodiments of the compositions disclosed herein, the at least one cultured astrocyte-like cell is or was cryopreserved, for example, in a cryopreservation medium comprising Chroman 1 and/or a derivative thereof, Emricasan and/or the derivative thereof, trans-ISRIB and polyamines comprising putrescine, spermine and spermidine. In some embodiments of the compositions disclosed herein, in the cryopreservation medium, Chroman 1 and/or the derivative thereof is or was at a concentration of about 4 nM to about 80 μM, wherein Emricasan and/or the derivative thereof is or was at a concentration of about 100 nM to about 80 μM, wherein trans-ISRIB is or was at a concentration of about 50 nM to about 80 μM, and wherein each of putrescine, spermine and spermidine is or was at a concentration of about 0.5 μM to 1 mM.

In another embodiment, a composition, comprising at least one cultured astrocyte-like cell exhibiting flat, star-shaped, and/or sphere morphology produced by the methods disclosed herein and expressing at least one marker, wherein the at least one marker is S100 Calcium-Binding Protein B (S100B), Nuclear Factor 1 A-Type Protein (NFIA), Hepatic and Glial Cell Adhesion Molecule (HEPACAM), glial fibrillary acidic protein (GFAP), CD44 protein, or vimentin (VIM).

In another embodiment, a cell culture comprising at least one cultured astrocyte-like cell exhibiting flat, star-shaped, and/or sphere morphology and detectably expressing at least one marker, wherein the at least one marker is S100 Calcium-Binding Protein B (S100B), Nuclear Factor 1 A-Type Protein (NFIA), Hepatic and Glial Cell Adhesion Molecule (HEPACAM), glial fibrillary acidic protein (GFAP), CD44 protein, or vimentin (VIM). In some embodiments of the cell cultures disclosed herein, detectable neuron-like cells can be present at 10% or less of total cells in culture. In some embodiments of the cell cultures disclosed herein, the cell culture can be grown from previously cryopreserved cells, for example, from the cells that were cryopreserved in a cryopreservation medium comprising Chroman 1 and/or a derivative thereof, Emricasan and/or the derivative thereof, trans-ISRIB and polyamines comprising putrescine, spermine and spermidine. In some embodiments of the cell cultures disclosed herein, the previously cryopreserved cells can be vertebrate pluripotent stem cells, such as induced pluripotent stem cells or embryonic pluripotent stem cells. In some embodiments of the cell cultures disclosed herein, the vertebrate pluripotent stem cells can be human pluripotent stem cells. In some embodiments of the cell cultures disclosed herein, the previously cryopreserved cells can also be cultured radial glia-like cells detectably expressing Brain Lipid Binding Protein (BLBP), CD133 (Prominin 1), abnormal spindle-like microcephaly-associated protein (ASPM), baculoviral inhibitor of apoptosis repeat-containing 5

(BIRC5 or Survivin), FAT Atypical Cadherin 1 (FAT1), Hes family bHLH transcription factor 5 (HES5), SRY-Box Transcription Factor 21 (SOX21), and PAX6 protein. In some embodiments of the cell cultures disclosed herein, the previously cryopreserved cells are astrocyte-like cell exhibiting flat, star-shaped, and/or sphere morphology and detectably expressing one or more of S100 Calcium-Binding Protein B (S100B), Nuclear Factor 1 A-Type Protein (NFIA), CD44, HEPACAM, Glial Fibrillary Acidic Protein (GFAP), and vimentin (VIM).

In another embodiment, a cell culture, comprising at least one cultured astrocyte-like cell exhibiting flat, star-shaped, and/or sphere morphology produced by the methods disclosed herein and detectably expressing at least one marker, wherein the at least one marker is S100 Calcium-Binding Protein B (S100B), Nuclear Factor 1 A-Type Protein (NFIA), Hepatic and Glial Cell Adhesion Molecule (HEPACAM), glial fibrillary acidic protein (GFAP), CD44 protein, or vimentin (VIM).

The invention will be further described in the following examples, which do not limit the scope of the invention described in the claims.

EXAMPLES

The Examples that follow are illustrative of specific embodiments of the invention, and various uses thereof. They are set forth for explanatory purposes only, and are not to be taken as limiting the invention.

Example 1: Differentiation of Human Pluripotent Stem Cells into Radial Glia-Like Cells and Astrocyte-Like Cells The procedure for differentiation of human pluripotent stem cells into radial glia-like cells and astrocyte-like cells is schematically illustrated in FIGS. 1 and 2. Human pluripotent stem cells (hPSCs), including embryonic stem cells (ESCs) and induced pluripotent stem cells (iPSCs), were maintained and expanded in defined E8 medium. Human ESC lines were purchased from WiCell (Madison, Wisconsin) and iPSCs were generated by NIH. hPSCs were grown as attached monolayer cultures. At the start of the differentiation procedure ("Day −1"), a defined number of hPSCs—about 10.000 cells/$cm^2$—was plated on vitronectin-coated surfaces in culture vessels and allowed to recover for one day in E8 medium supplemented with CEPT to ensure consistent cytoprotection and optimal cell survival after cell dissociation. To initiate cell differentiation at "Day 0," the supplemented E8 medium was exchanged for Astro 1 Medium (see FIG. 2), which was changed daily for the next 15 days. The cells where passaged when they became confluent (1:3 ratio), which typically occurred 4-5 times during the 15-day differentiation period. At "Day 15," the culture medium was switched to Astro 2 Medium (see FIG. 2). Between "Day 15" and "Day 30," the cells were cultured in Astro 2 Medium with daily medium changes and passaged once around Day 23 (1:2 ratio), as cells decreased their proliferative activity at that time point. At "Day 30," switch to Astro 3 Medium (see FIG. 2) was performed for cell maturation, with the medium changes conducted every 3 days. During the culture procedures described above, the cells were passaged by Accutase exposure for 7 minutes at every passage. Exemplary images of the cells at different time points in the above differentiation procedure are shown in FIG. 1B.

Figure 3B:
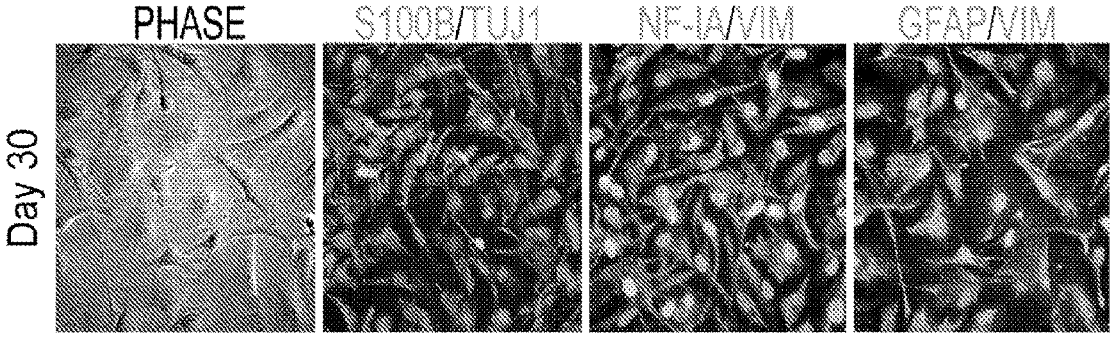
Figure 3C:
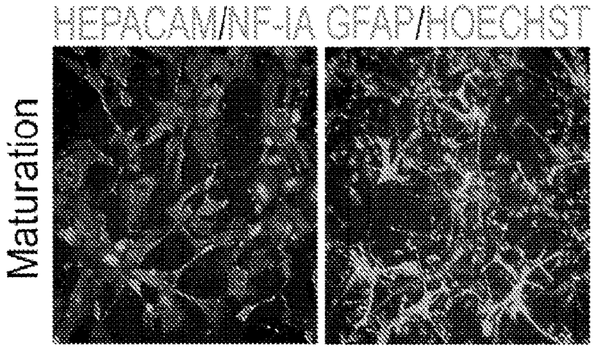

Example 2: Immunochemical Characterization of Radial Glia-Like Cells and Astrocyte-Like Cells Derived from Human iPSCs The cells produced according to the procedure described in Example 1 exhibited highly efficient differentiation into astrocyte-like cells, as illustrated by the figures discussed below. FIG. 3 shows representative images of the cells from different time points of the differentiation procedure discussed in Example 1. In FIG. 3, the images labeled "PHASE" are phase-contrast microscopy images. The images labeled with the name of the specific proteins are microphotographs of cells immunochemically stained with the antibodies (both monoclonal and polyclonal) specific for the indicated proteins, which are discussed below. The procedure was performed on human iPSCs. The images show highly efficient and controlled differentiation of human iPSCs into specific cell types. As illustrated in FIG. 3A, at "Day 5," differentiating cells expressed the neural stem cell marker Paired Box Protein Pax-6 (PAX6), followed by the radial glia marker Brain Lipid Binding Protein (BLBP) at "Day 7." At "Day 15," the astrocyte marker S100 Calcium-Binding Protein B (S100B) was widely expressed. As illustrated in FIG. 3B, at "Day 30," the culture was substantially composed of large cells with flat morphologies expressing the typical astrocyte markers S100B, Nuclear factor 1 A-type (NFIA), CD44, HEPACAM, glial fibrillary acidic protein (GFAP), and vimentin (VIM). Only a small proportion of the cells in the culture was detected by an antibody to neuronal maker beta-III Tubulin (TUJ1). As illustrated in FIG. 3C, the astrocyte-like cells generated by the differentiation procedure were cryopreserved at "Day 30" or cultured for additional 20 days and passaged two times, which led to further cell maturation indicated by star-shaped morphologies and the expression of Hepatic and Glial Cell Adhesion Molecule (HEPACAM), CD44, glial fibrillary acidic protein (GFAP), and NFIA.

Figure 4:
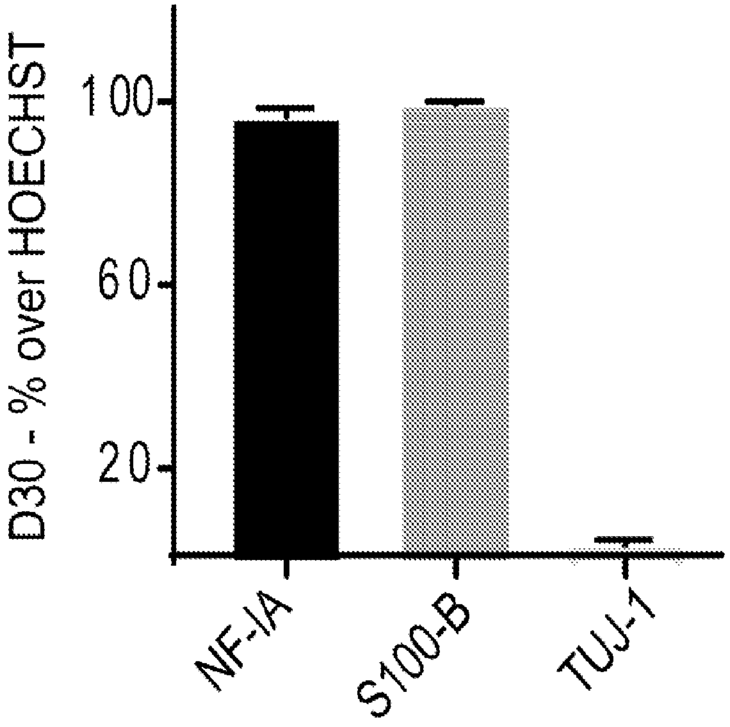
FIG. 4 shows a bar graph illustrating the percentage of cells expressing the astrocytic markers NFIA and S100-beta and the neuronal marker TUJ1 (beta-III Tubulin) at "Day 30" of the differentiation procedure.

Quantitative analysis of the cell cultures produced from hPSCs according to the procedure described in Example 1 demonstrates highly efficient differentiation in such cultures, as illustrated by FIG. 4. At "Day 30," the cells were stained for the astrocyte markers NFIA and S100B and the neuronal marker TUJ1. The vast majority of the cells in the culture were found to be astrocyte-like cells expressing NFIA and S100B, whereas neuron-like cells were produced only sporadically.

Figure 5A:
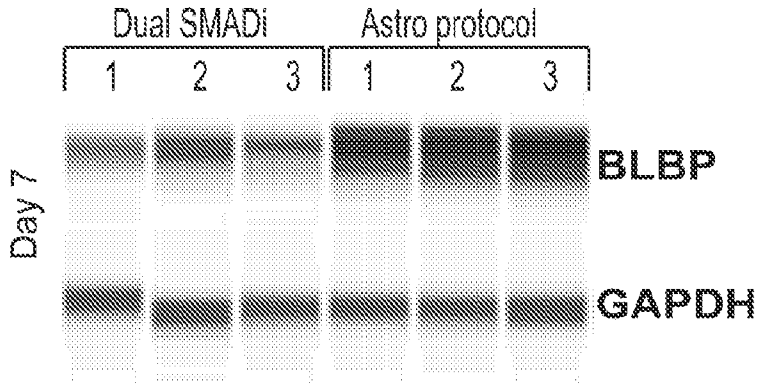
FIGS. 5A-B show an image of a Western blot generated from differentiating radial glial cells at "Day 7" of the differentiation procedure (FIG. 5A) and demonstration of their multipotency (FIG. 5B).
Figure 5B:
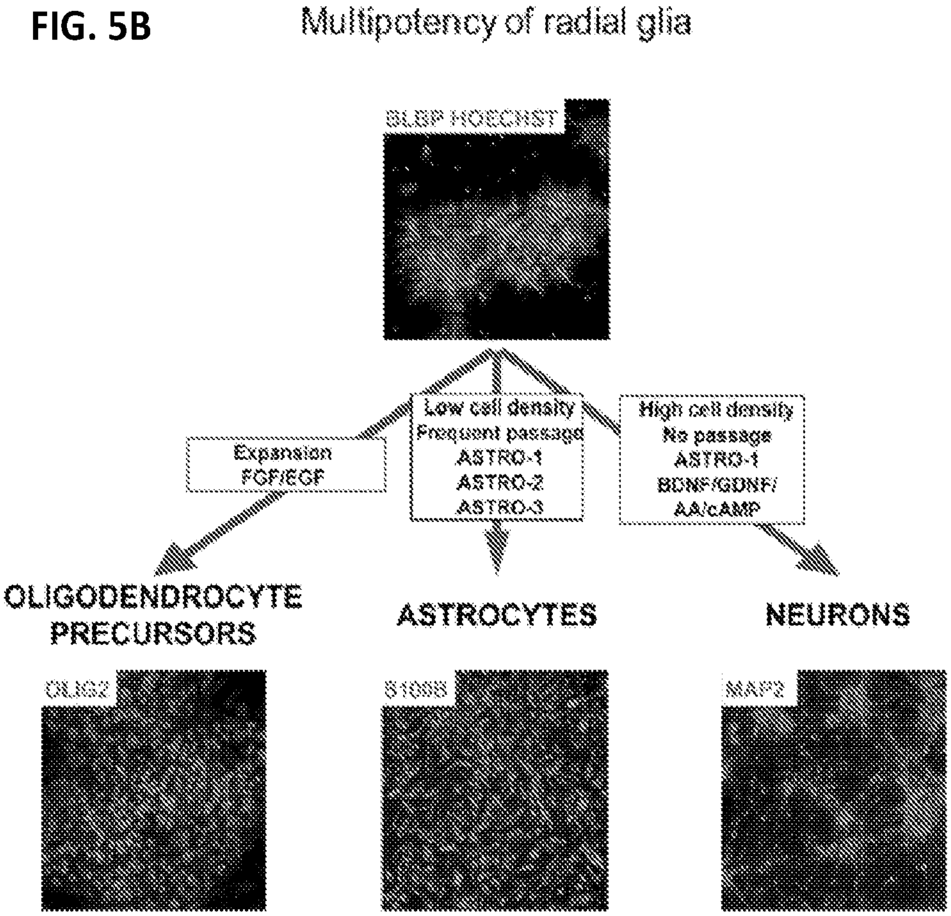

Western blot analysis of differentiating cells produced from hPSCs according to the procedure described in Example 1 demonstrated the superiority of the currently described procedure, as compared to the previously described procedure relying on dual-SMAD inhibition strategy (Chambers et al., "Highly efficient neural conversion of human ES and iPS cells by dual inhibition of SMAD signaling." Nat. Biotechnol. 27(3):275-280 (2009) and Tchieu et al., "NFIA is a gliogenic switch enabling rapid derivation of functional human astrocytes from pluripotent stem cells" Nat. Biotechnol. 37:267-275 (2019)). The results of the Western blot analysis are illustrated in FIG. 5A. For the comparison of the two procedures, hPSCs were exposed to Dual-SMADi or the Astro 1 medium for 7 days and then analysed for expression of the radial glial marker BLBP. The "house-keeping" protein Glyceraldehyde-3-Phosphate Dehydrogenase (GAPDH) was used as a control indicating that similar amounts of proteins were loaded on the lanes of the gel used to produce the Western blot. Three replicate experiments showed that Astro 1 medium resulted in much stronger expression of BLPB in the cultured cells than the Dual-SMAD inhibition strategy. Multipotency of radial glia like cells was confirmed by differentiation of BLBP positive cells to OLIG2-positive precursors of oligodendrocytes, S100B-positive astrocytes and MAP2-positive neurons as illustrated in FIG. 5B. For differentiation to OLIG2 precursors of oligodendrocytes radial glia-like cells were expanded over 3 passages in DMEM/F12 medium supplemented with N2 and B27 (without vitamin A), and addition of basic fibroblast growth factor (bFGF) and epidermal growth factor (EGF). For differentiation to MAP2 positive neurons, radial glia cells were maintained for 5 days in high cell density condition in ASTRO1 medium, and sub-cultured at high density in DMEM media supplemented with N2 and B27 (with vitamin A) with addition of brain-derived neurotrophic factor (BDNF), glial-derived neurotrophic factor (GDNF), Ascorbic acid (AA), and cyclic adenosine-monophosphate (cAMP) for additional 15 days. Differentiation to astrocytes was performed using the methods and embodiments of the present invention.

Example 3: Time-Course Gene Expression Profiling

Figure 6:
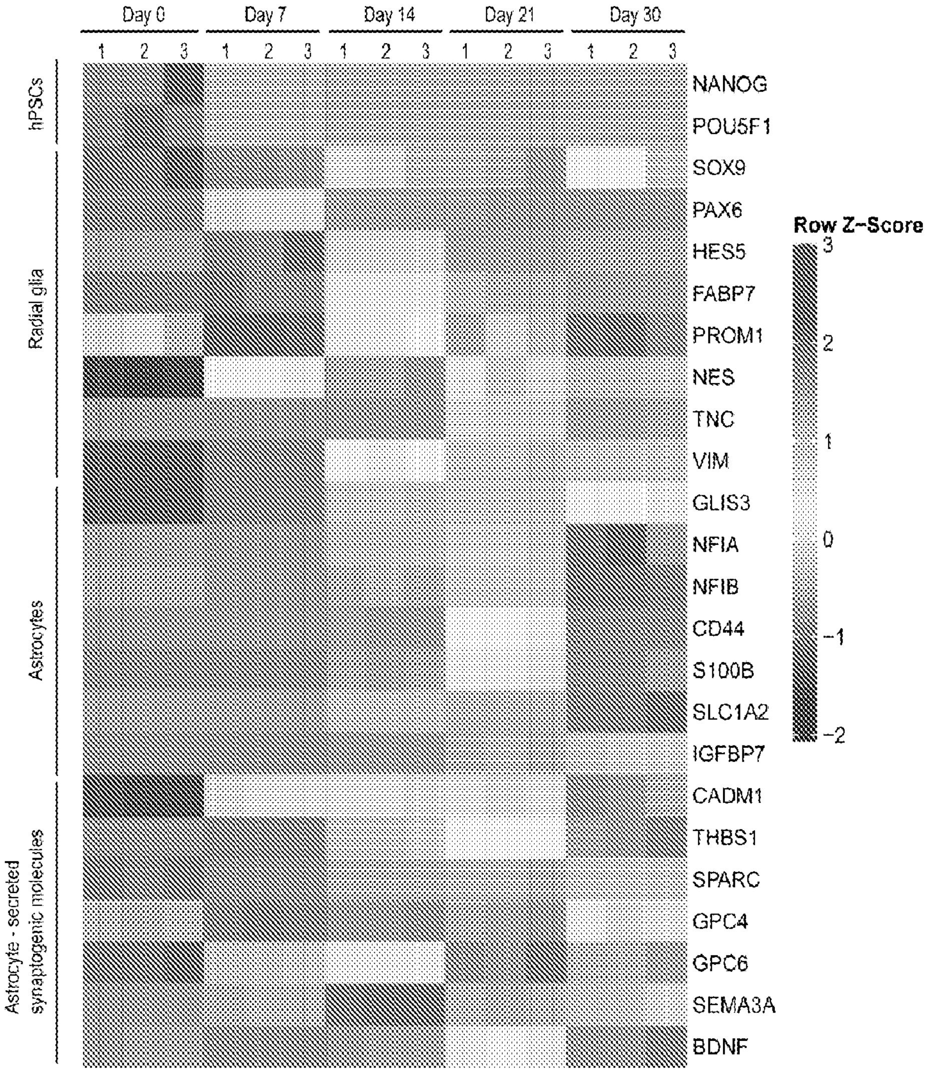
FIG. 6 shows the results of time-course gene expression profiling by RNA-seq of the cells differentiated by the differentiation procedure.

The cells produced according to the procedure described in Example 1 were characterized by time-course gene expression profiling accomplished by RNA-sequencing ("RNA-seq") analysis, as illustrated by the figures discussed below. Time-course gene expression profiling by RNA-seq of differentiation of hPSCs is illustrated in FIG. 6. Systematic analysis of gene expression at "Days 0-30" demonstrated step-wise and controlled differentiation of hPSCs into radial glia-like cells and astrocyte-like cells. Natural astrocytes are known to support function and survival neuronal cells by secreting important neurotrophic and synaptogenesis-promoting proteins. As shown in the bottom part of FIG. 6, transcription of several important astrocyte-secreted proteins was induced in the cell culture at "Days 21-30," for example, BDNF, SEMA3A and THBS1.

Figure 7:
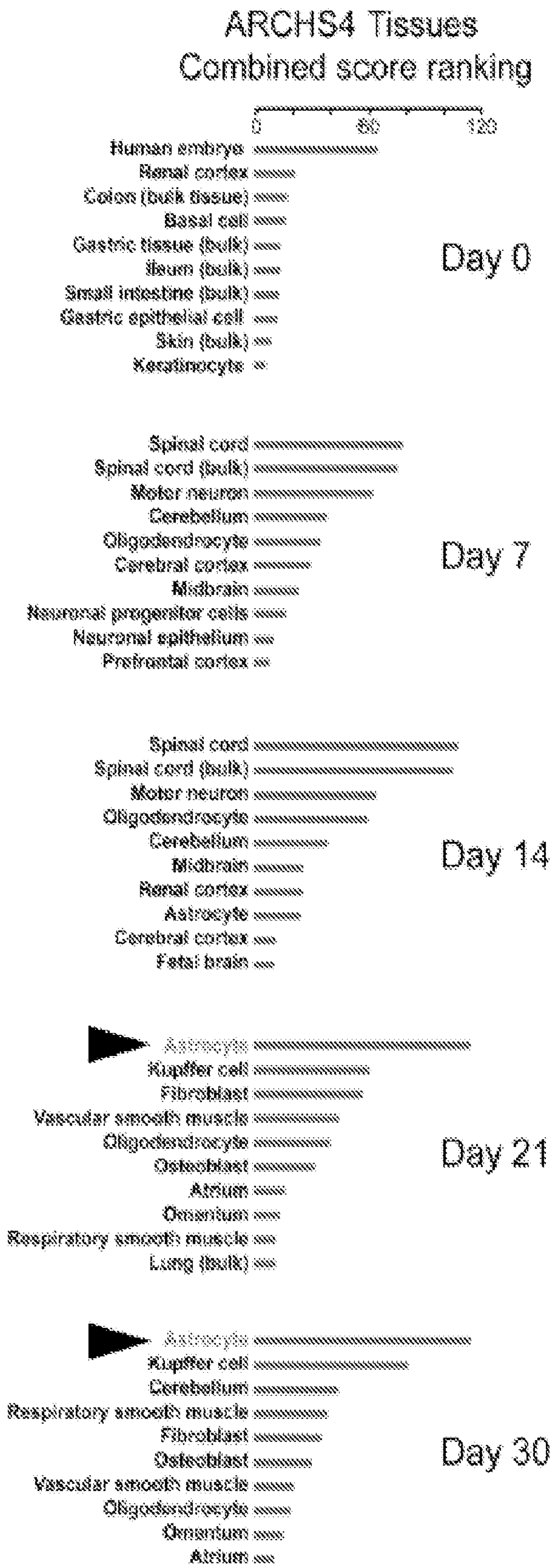
FIG. 7 shows the results of the comparison of the time-course gene expression profiling by RNA-seq of the cells produced by the differentiation procedure with the information available in ARCHS4 human tissue RNA-seq database.

The results of time-course gene expression profiling by RNA-seq of the cells produced according to the procedure described in Example 1 were compared to the results available in public databases. FIG. 7 illustrates the results of the comparison. For gene ontology analysis, web-based tool EnrichR available online through Mount Sinai Center for Bioinformatics, Icahn School of Medicine at Mount Sinai (New York, N.Y., USA) was used to compare the top 200 genes upregulated at each time point indicated in FIG. 7 ("Day 0," "Day 7," "Day 14," "Day 21" and "Day 30") and compared to the ARCHS$^4$ human tissue RNA-seq database, also available through Mount Sinai Center for Bioinformatics, Icahn School of Medicine at Mount Sinai. The top ten matches for the gene upregulation profile at each time point were plotted in FIG. 7. "Astrocyte" was a top hit for the cultured cells produced according to the procedure described in Example 1 at both "Day 21" and "Day 30," confirming the astrocyte-like identity of cells generated.

Figure 8:
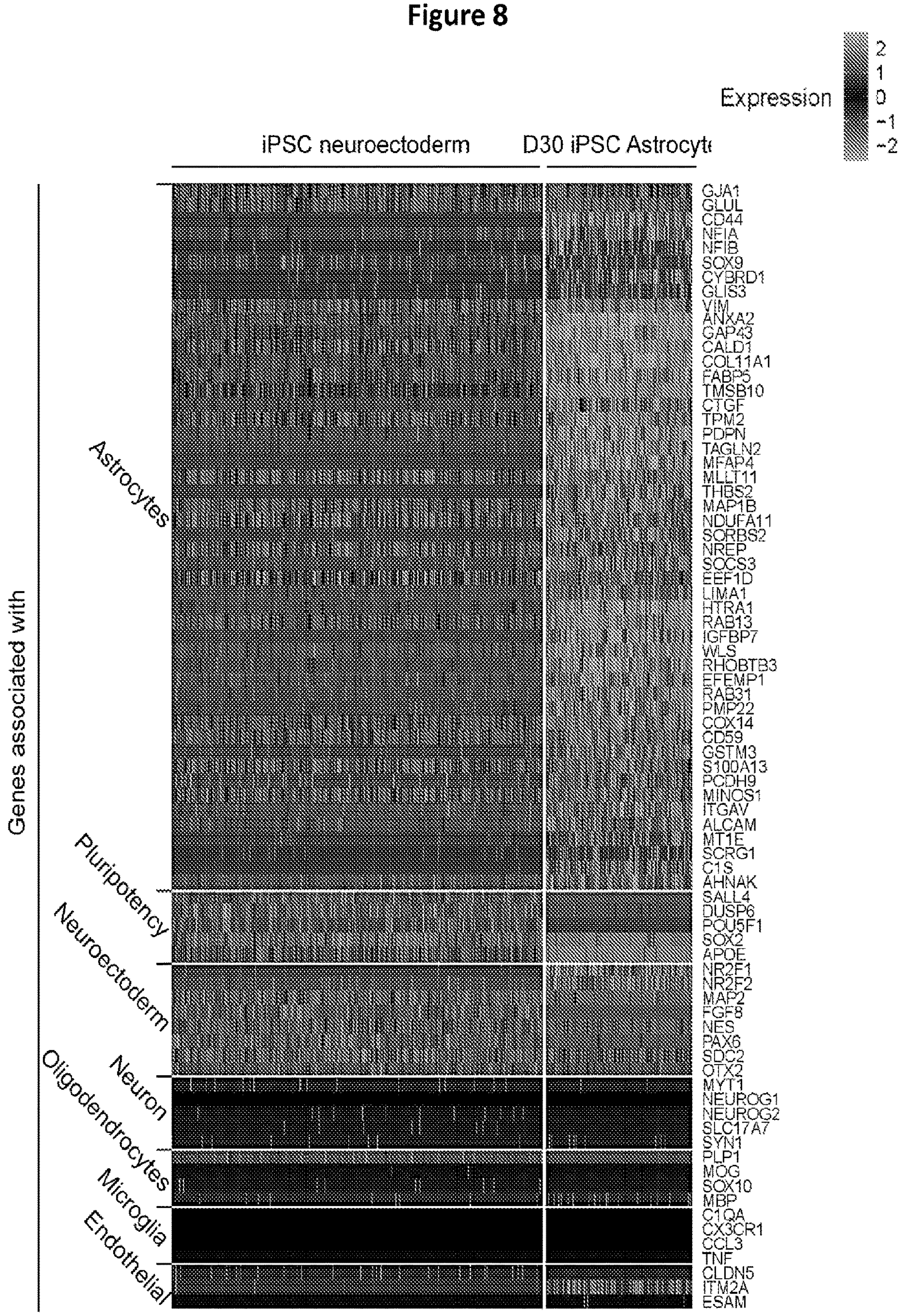
FIG. 8 shows the results of single cell RNA-seq of the cells produced by the differentiation procedure and comparison of the results to other cell types indicated (pluripotent stem cells, neuroectoderm, neuronal cells, oligodendrocytes, microglia, and endothelial cells).

Comparative single-cell analysis and gene expression profiling of the cells produced from iPSCs by the procedure described in Example 1 was performed, with the results illustrated in FIG. 8. Single cell RNA-seq and comparison of the results to other cell types indicated in FIG. 8 (pluripotent stem cells, neuroectoderm, neuronal cells, oligodendrocytes, microglia, endothelial cells) confirmed that, at "Day-30," iPSC-derived cells displayed a gene expression signature characteristic of human astrocytes.

Figure 9A:
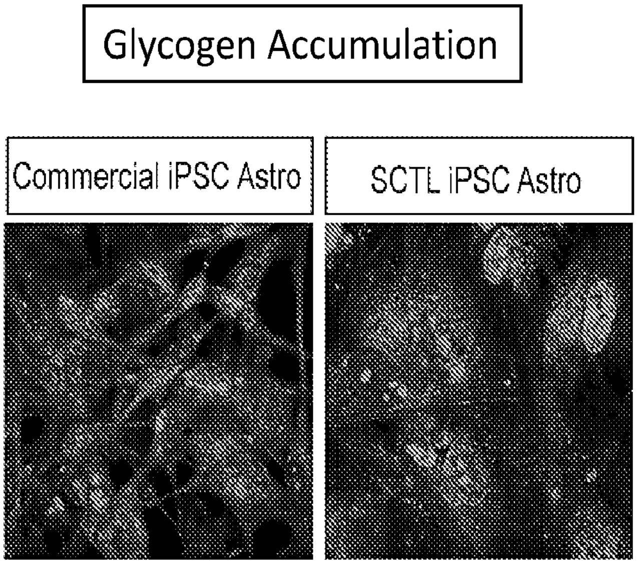
FIGS. 9A-B show functional analysis of astrocyte cells derived from iPSCs according to the differentiation procedure.
Figure 9B:
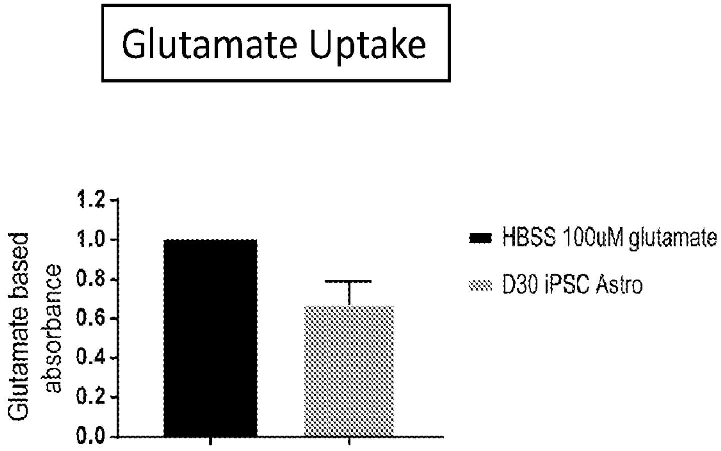

Example 4: Functional Characterization of Astrocyte-Like Cells Derived from iPSCs Functional analysis of astrocyte cells derived from iPSCs according to the procedure described in Example 1 was performed, with the results illustrated in FIGS. 9-11 and discussed below. FIG. 9A shows exemplary microscopic images illustrating comparable glycogen accumulation capacity of the iPSC-derived astrocyte-like cells derived according to the procedure described in Example 1 ("SCTL iPSC Astro") and commercially available iPSC-derived astrocyte-like cells ("Commercial iPSC Astro," sourced from Fujifilm Cellular Dynamics International). FIG. 9B shows a bar graph illustrating the basal level of glutamate in the medium and reduction of glutamate levels in the medium after 3-hour incubation with astrocytes. Glutamate concentration was determined by an enzymatic assay that generated in a colorimetric product in the amounts proportional to glutamate levels. The data illustrated in FIG. 9B showed that the iPSC-derived astrocyte-like cells derived according to the procedure described in Example 1 are capable of glutamate uptake, which is consistent with the functional role of natural astrocytes in the human brain.

Figure 10A:
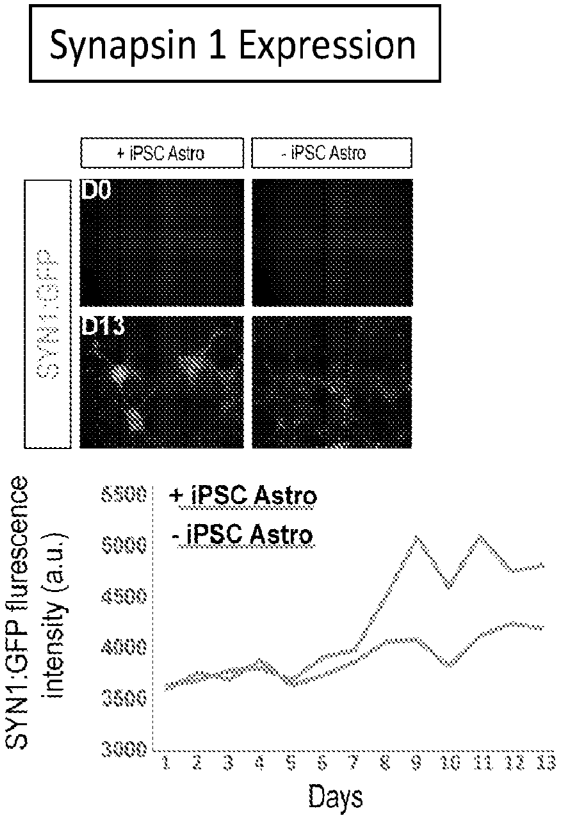
FIGS. 10A-B show the experimental results illustrating that the iPSC-derived astrocyte-like cells derived according to the differentiation procedure promoted neuronal maturation and synaptic activity.
Figure 10B:
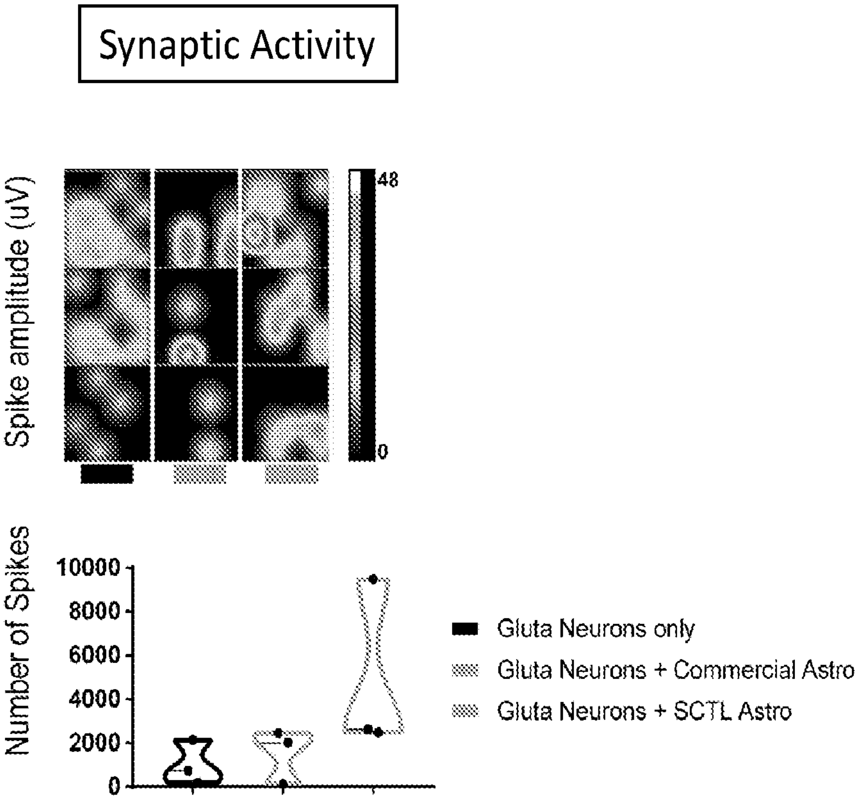

FIG. 10 illustrates the experimental results showing that the iPSC-derived astrocyte-like cells derived according to the procedure described in Example 1 promoted neuronal maturation and synaptic activity. To generate the data illustrated in FIG. 10A, neuronal cells were derived from a human ESC reporter cell line (SYN1:GFP; green fluorescent protein expressed under the control of the synapsin 1 promoter) and cultured for 13 days with and without the iPSC-derived astrocyte-like cells derived according to the procedure described in Example 1. The neurons showed higher levels of synapsin 1 expression when co-cultured with the iPSC-derived astrocyte-like cells, which demonstrated the ability of the iPSC-derived astrocyte-like cells to promote synaptic maturation. The data illustrated in FIG. 10B illustrates the results of the multi-electrode array experiments (Axion Biosystems) demonstrating that glutamatergic neurons sourced from Fujifilm Cellular Dynamics International showed increased number of spikes and functional activity when co-cultured with iPSC-derived astrocyte-like cells for 72 hours.

Figure 11:
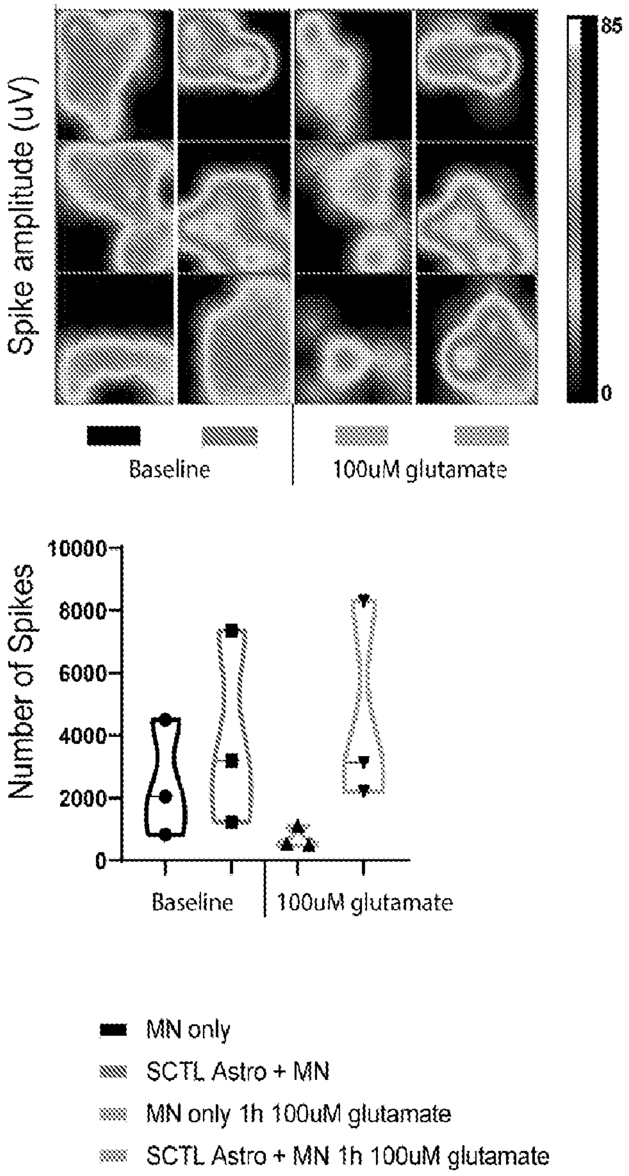
FIG. 11 shows cytoprotective effects of astrocyte-like cells on motor neuron activity upon exposure to glutamate. Motor neurons were purchased from Fujifilm Cellular Dynamics International and cultured with or without astrocyte-like cells produced by the differentiation procedure in Example 1.

FIG. 11 illustrates neuroprotective effects of the iPSC-derived astrocyte-like cells derived according to the procedure described in Example 1. Multi-electrode array experiments were performed using the Maestro APEX system (Axion Biosystems). The bars in the graph shown in the bottom panel of FIG. 11 display representative data points. It is well-known that high concentrations of glutamate in the extracellular space can damage and kill neuronal cells (excitotoxicity). In fact, excitotoxicity is considered an important contributing factor for various neurodegenerative diseases, such as amyotrophic lateral sclerosis, also known as Lou Gehrig's disease. To model this aspect of neurodegenerative diseases, motor neurons sourced from Fujifilm Cellular Dynamics International were co-cultured with and without the iPSC-derived astrocyte-like cells for 7 days (baseline) until they have achieved electrical activity measured by the number of spikes. At day 7 treatment with 100 μM glutamate was administered for 1 hour, and the number of spikes was measured again (100 μM glutamate). The activity of motor neurons cultured without astrocytes was reduced upon treatment with 100 μM glutamate. Multi-electrode array experiments demonstrated that the iPSC-derived astrocyte-like cells were capable of protecting motor neurons from the toxic effects of glutamate.

Example 5: Automated Procedure

Figure 12A:
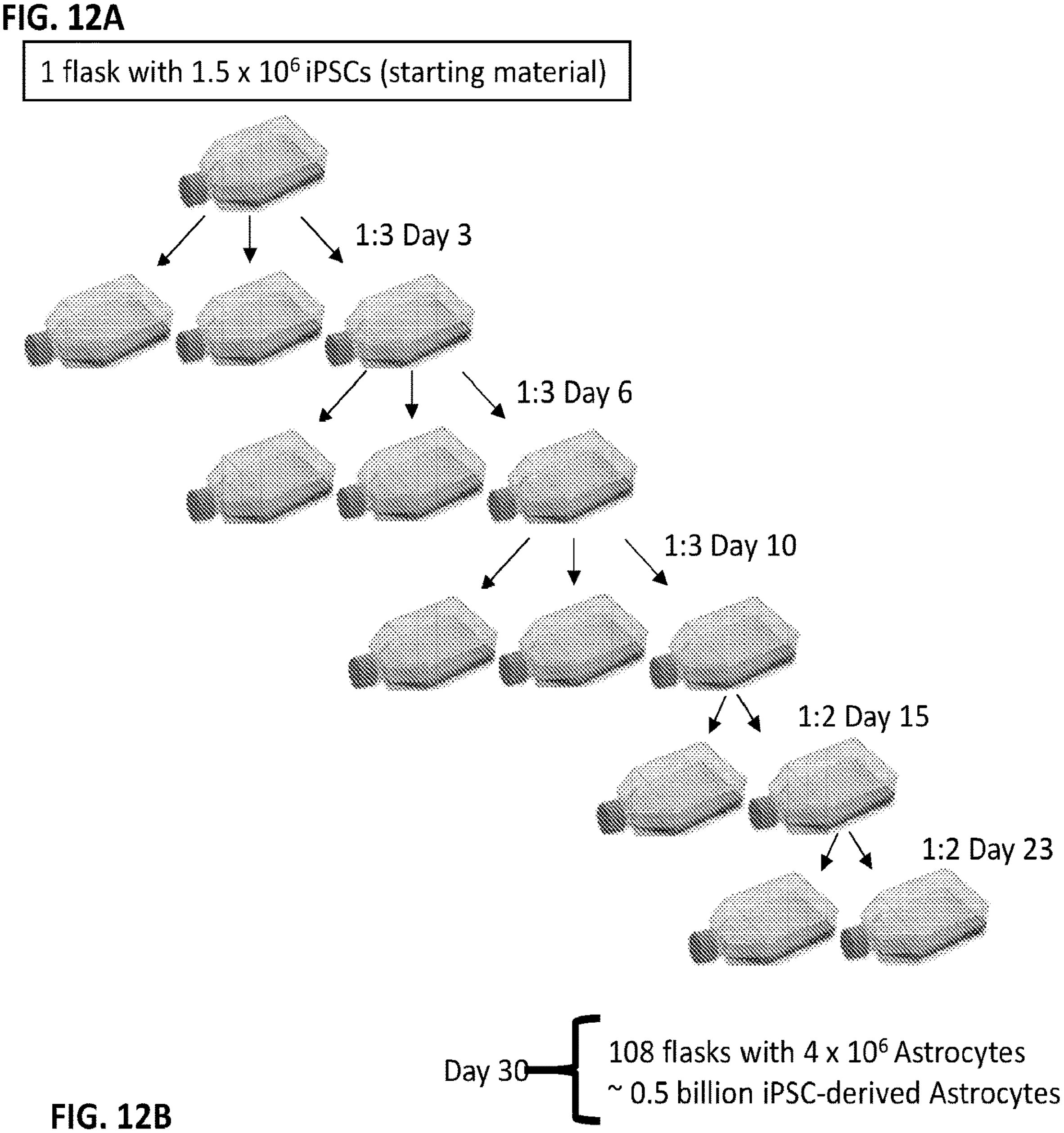
FIGS. 12A-B show an automated procedure by using the CompacT SelecT® system (Sartorius, Wilmington, USA) based on the procedure described in Example 1.
Figure 12B:
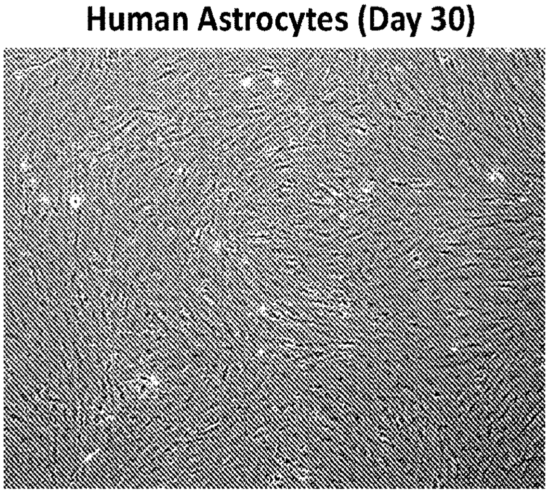
Figure 14:
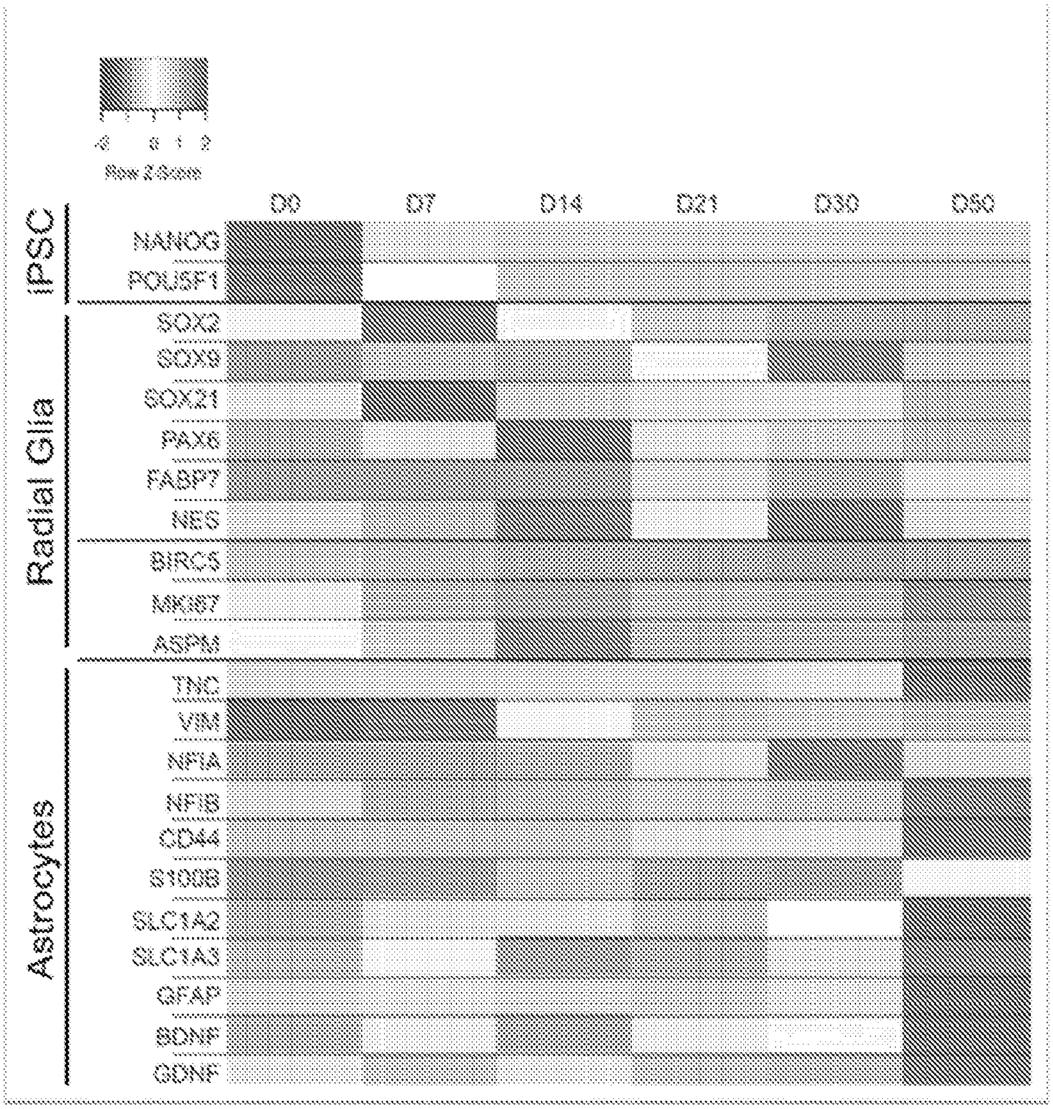
FIG. 14 shows results of time-course gene expression profiling by RNA sequencing demonstrating stepwise differentiation into radial glia and astrocytes. Heat-map (RNA-seq) illustrating genes expressed by pluripotent stem cells, radial glial cells, and astrocytes (day 0-50).
Figure 15:
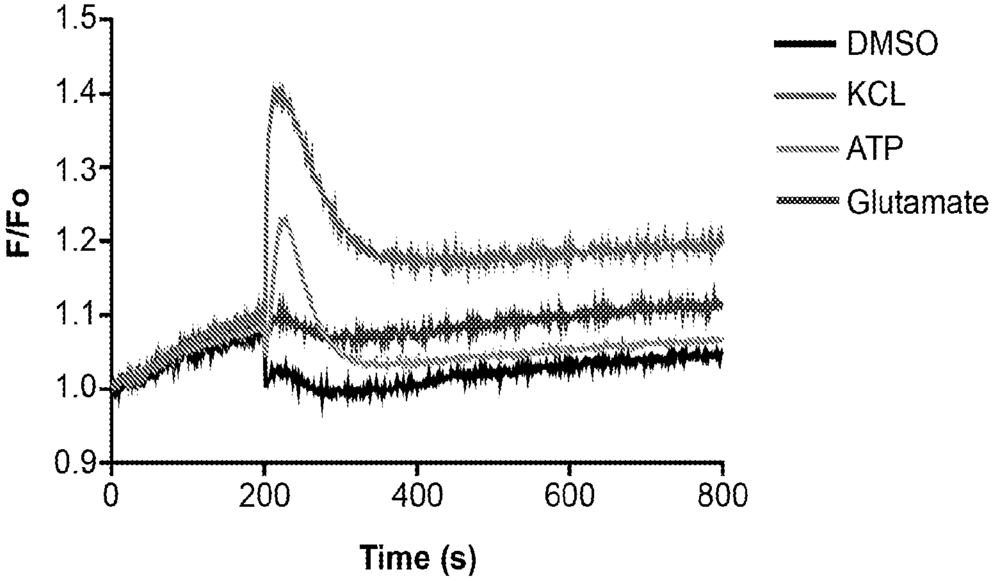
FIG. 15 shows iPSC-astrocytes display calcium transients in response to appropriate stimuli. iPSC-derived astrocytes show typical physiological response and increase of intracellular calcium levels in response KCL, ATP and L-glutamate. DMSO was used as control treatment.

The procedure described in Example 1 was used as a basis for an automated procedure by using the CompacT SelecT® system (Sartorius, Wilmington, USA) illustrated in FIG. 12. Highly efficient, standardized and scalable production of astrocyte-like cells from iPSCs was achieved using the automated procedure. FIG. 12A schematically illustrates the automated protocol. FIG. 12B shows a representative microscopic image of the cell culture at "Day 30" of the automated procedure.

Example 6: Sphere Formation to Enhance Astrocyte Maturation

The procedure for sphere formation was used to enhance astrocyte maturation as schematically illustrated in FIGS. 13A-C. The entire astrocyte differentiation procedure was executed as monolayer or to include a sphere formation stage as described below. The sphere formation step at Day 14 resulted in mature cells and reduced cell passaging steps. Single cell dissociation was performed at day 14 and cells were maintained for 24 h in Astro-2 medium with CEPT in suspension to form spheres (100.000 cells/well of the 96-well plate with U bottom). One day later, spheres were then transferred to a vessel with low-cell attachment surface in Astro-2 medium. Media change was performed every other day. After one week in Astro-2 medium, Astro-3 containing DMEM/F12 media supplemented with N2 B27 complete, chemically defined lipid concentrate (2%), LIF (10 ng/ml), and CNTF (10 ng/ml) or enriched Astro-3 medium were introduced. The enriched Astro-3 contained DMEM/F12 media supplemented with N2 B27 complete, chemically defined lipid concentrate (2%), LIF (10 ng/ml), and CNTF (10 ng/ml), Jagged 1 (10 ng/ml), DLL-1 (10 ng/ml), triiodothyronine (also known as T3 is a thyroid hormone) (40 ng/ml), phorbol ester (200 nM), forskolin 2 μM, neuregulin-1 (20 ng/ml), and ascorbic acid (200 μM). Spheres were cultured in Astro-3 or enriched Astro-3 medium for another week with media change every other day. At day 28, spheres were single-cell dissociated by Accutase treatment and astrocytes were maintained as monolayer culture in Astro-3 or enriched Astro-3 media until day 50.

Having described the invention in detail and by reference to specific embodiments thereof, it will be apparent that modifications and variations are possible without departing from the scope of the invention defined in the appended claims. More specifically, although some aspects of the instant invention are identified herein as particularly advantageous, it is contemplated that the instant invention is not necessarily limited to these particular aspects of the invention.

What is claimed is:

1. A method of producing, in culture, radial glia-like cells, the method comprising:
- (a) plating vertebrate pluripotent stem cells on a substrate-coated surface of a culture vessel at a density of 1,000-100,000 cells/$cm^2$;
- (b) incubating the plated vertebrate pluripotent stem cells in a first culture medium
- (c) replacing the first culture medium with a second culture medium comprising:
  - (i) an effective amount or concentration of one or more inhibitors of BMP pathway, wherein the one or more inhibitors of the BMP pathway comprise one or more LDN-193189, LDN-214117, LDN-212854, DMH2, ML 347, UK 3833687, K 02288, Dorsomorphin, Noggin, Chordin, Follistatin, or Gremlin,
  - (ii) an effective amount or concentration of one or more activators of Notch pathway wherein the effective amount or concentration of the one or more activators of Notch pathway in the second culture medium comprise one or more of Jagged 1 protein, Jagged 2 protein, and Delta-Like protein 1 (DLL1), Delta-Like protein 2 (DLL2), or Delta-Like protein 3 (DLL3), and
  - (iii) one or more cytokines of interleukin-6 family; and
- (d) culturing the plated vertebrate pluripotent stem cells in the second culture medium; wherein the resulting radial glia-like cells detectably express one or more of Brain Lipid Binding Protein (BLBP), abnormal spindle-like microcephaly-associated protein (ASPM), baculoviral inhibitor of apoptosis repeat-containing 5 (BIRC5 or Survivin), FAT Atypical Cadherin 1 (FAT1), Hes family bHLH transcription factor 5 (HES5), and SRY-Box Transcription Factor 21 (SOX21).

2. The method of claim 1, wherein the substrate comprises vitronectin, laminin 521, and/or a soluble basement membrane extract from the Engelbreth-Holm-Swarm (EHS) mouse tumor.

3. The method of claim 1, wherein plating vertebrate pluripotent stem cells comprises plating at the cell density of 2,000-90,000 cells/$cm^2$; 3,000-80,000 cells/$cm^2$; 4,000-70,000 cells/$cm^2$; 5,000-50,000 cells/$cm^2$, and/or 10,000-30,000 cells/$cm^2$.

4. The method of claim 1, wherein:
- (a) incubating the plated vertebrate pluripotent stem cells in the first culture medium comprises incubating for 12-48 hours; and
- (b) culturing the plated vertebrate pluripotent stem cells in the second culture medium comprises culturing for at least 5-20 days.

5. The method of claim 1, wherein:
- (a) the first culture medium is a first defined culture medium, wherein the first defined culture medium is a xeno-free, feeder-free, serum-free, and animal-origin-free medium suitable for maintenance and expansion of human pluripotent stem cells (hPSCs), or mouse embryonic fibroblast (MEF)-conditioned medium;
- (b) the first culture medium comprises an effective concentration of Chroman 1, an effective concentration of Emricasan, an effective concentration of trans-ISRIB, and an effective concentration of polyamines comprising putrescine, spermine, and spermidine, wherein the effective concentration of Chroman 1 is about 4 nM to about 80 μM, the effective concentration of Emricasan is about 100 nM to about 80 μM, the effective concentration of trans-ISRIB is about 50 nM to about 80 μM, and wherein putrescine, spermine, and spermidine is each at a concentration of about 0.5 nM to 1 mM; and
- (c) the first culture medium further comprises at least one inhibitor of Rho-associated protein kinase (ROCK), wherein the one or more ROCK inhibitors comprise one or more of Chroman 1, Y27632, blebbistatin, or thiazovivin.

6. The method of claim 1, wherein, during the culturing in the second culture medium, the cells being cultured detectably express:
- (a) one or more radial glia cell markers at approximately 4-10 days after start of the culturing in the second culture medium;
- (b) one or more astrocyte markers at approximately 5-20 days after start of the culturing; and/or
- (c) one or more neural stem cell markers at approximately 2-10 days after start of the culturing.

7. The method of claim 1, wherein the produced radial glia-like cells further detectably express one or more of CD133 (Prominin 1) and PAX6 protein.

8. The method of claim 1, wherein the second culture medium is a second defined culture medium, wherein the second defined culture medium is DMEM-F12, a defined, feeder-free stem cell culture medium, a serum-free basal cell culture medium, or minimal essential medium (MEM).

9. The method of claim 8, wherein the second defined culture medium comprises N2 supplement and/or B27 supplement without vitamin A; or wherein the one or more inhibitors of the BMP pathway comprise one or more of LDN-193189, LDN-214117, LDN-212854, DMH2, ML 347, UK 383367, K 02288, Dorsomorphin, Noggin, Chordin, Follistatin, or Gremlin; or wherein the effective amount or concentration of the one or more inhibitors of the BMP pathway comprise 2 nM-40 μM LDN-193189; or wherein the second culture medium further comprises an effective amount or concentration of one or more Platelet-Derived Growth Factor protein; or wherein the one or more Platelet-Derived Growth Factor protein is Platelet-Derived Growth Factor-AA (PDGF-AA), Platelet-Derived Growth Factor-BB (PDGF-BB), or Platelet-Derived Growth Factor-AB (PDGF-AB); or wherein the effective amount or concentration of the one or more Platelet-Derived Growth Factor protein is 1 ng/ml-800 ng/ml; or wherein the effective amount or concentration of the one or more activators of Notch pathway in the second culture medium comprise one or more of Jagged 1 protein, Jagged 2 protein, and Delta-Like protein 1 (DLL1), Delta-Like protein 2 (DLL2), or Delta-Like protein 3 (DLL3); or wherein the one or more activators of Notch pathway in the second culture medium comprise one or both of 1 ng/ml-800 ng/ml Jagged 1 protein and 1 ng/ml-800 ng/mL Delta-Like protein 1 (DLL1).

10. The method of claim 1, wherein the second culture medium further comprises an effective amount or concentration of one or more Platelet-Derived Growth Factor protein.

11. The method of claim 10, wherein the one or more Platelet-Derived Growth Factor protein is Platelet-Derived Growth Factor-AA (PDGF-AA), Platelet-Derived Growth Factor-BB (PDGF-BB), or Platelet-Derived Growth Factor - AB (PDGF-AB); and wherein the effective amount or concentration of the one or more Platelet-Derived Growth Factor protein is 1 ng/ml-800 ng/ml.

12. The method of claim 1, wherein the one or more cytokines of interleukin-6 family in the second culture medium comprise one or more of Oncostatin M protein, Ciliary-Derived Neurotrophic Factor protein (CNTF) and Leukemia-Inhibitory Factor protein (LIF).

13. The method of claim 12, wherein each of the one or more Oncostatin M protein, Ciliary-Derived Neurotrophic Factor protein (CNTF) and Leukemia-Inhibitory Factor protein (LIF) is present in the second culture medium in a concentration of 1 ng/ml-800 ng/mL.

14. The method of claim 1, wherein the culturing in the second culture medium comprises changing the second culture medium approximately every 20- 28 hours.

15. The method of claim 1, wherein the culturing in the second culture medium comprises one or more steps of passaging the cells being cultured when they become confluent.

16. The method of claim 15, wherein the one or more steps of passaging the cells are performed at 1:3 to 1:5 ratio of confluent cell culture to fresh medium; and wherein the culturing in the second culture medium comprises 3-7 of the passaging steps.

17. The method of claim 1, wherein the effective amount or concentration of the one or more inhibitors of the BMP pathway comprise 2 nM-40 μM LDN-193189.

18. The method of claim 1, wherein the one or more activators of Notch pathway in the second culture medium comprise one or both of 1 ng/ml-800 ng/ml Jagged 1 protein and 1 ng/ml-800 ng/ml Delta-Like protein 1 (DLL1).

* * * * *